US010125188B2

(12) United States Patent
Gurnett-Bander et al.

(10) Patent No.: US 10,125,188 B2
(45) Date of Patent: Nov. 13, 2018

(54) HUMAN ANTIBODIES TO RESPIRATORY SYNCYTIAL VIRUS F PROTEIN AND METHODS OF USE THEREOF

(71) Applicant: Regeneron Pharmaceuticals, Inc., Tarrytown, NY (US)

(72) Inventors: Anne Gurnett-Bander, Carmel, NY (US); David Perez-Caballero, Briarwood, NY (US); Sumathi Sivapalasingam, Brooklyn, NY (US); Xunbao Duan, Ambler, PA (US); Douglas MacDonald, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 19 days.

(21) Appl. No.: 15/229,567

(22) Filed: Aug. 5, 2016

(65) Prior Publication Data

US 2017/0029488 A1    Feb. 2, 2017

Related U.S. Application Data

(63) Continuation of application No. 14/207,797, filed on Mar. 13, 2014, now Pat. No. 9,447,173.

(60) Provisional application No. 61/911,093, filed on Dec. 3, 2013, provisional application No. 61/782,215, filed on Mar. 14, 2013.

(51) Int. Cl.
| | |
|---|---|
| *C07K 16/10* | (2006.01) |
| *A61K 45/06* | (2006.01) |
| *G01N 33/569* | (2006.01) |
| *A61K 39/42* | (2006.01) |
| *A61K 39/00* | (2006.01) |

(52) U.S. Cl.
CPC .......... *C07K 16/1027* (2013.01); *A61K 39/42* (2013.01); *A61K 45/06* (2013.01); *G01N 33/56983* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2317/94* (2013.01); *C12N 2760/18521* (2013.01); *G01N 2333/135* (2013.01)

(58) Field of Classification Search
None
See application file for complete search history.

(56) References Cited

U.S. PATENT DOCUMENTS

| | | | |
|---|---|---|---|
| 5,762,905 A | 6/1998 | Butron et al. | |
| 5,811,524 A | 9/1998 | Brams et al. | |
| 5,824,307 A | 10/1998 | Johnson | |
| 5,840,298 A | 11/1998 | Brams et al. | |
| 6,413,771 B1 | 7/2002 | Brams et al. | |
| 6,537,809 B2 | 3/2003 | Brams et al. | |
| 6,656,467 B2 | 12/2003 | Young et al. | |
| 6,750,008 B1 | 6/2004 | Jeffs et al. | |
| 7,635,568 B2 | 12/2009 | Young et al. | |
| 7,740,851 B2 | 6/2010 | Young et al. | |
| 8,221,759 B2 | 7/2012 | Pilkington et al. | |
| 8,562,996 B2 | 10/2013 | Spits et al. | |
| 9,447,173 B2 | 9/2016 | Gurnett-Bander et al. | |
| 2003/0091584 A1 | 5/2003 | Young et al. | |
| 2006/0083741 A1 | 4/2006 | Hoffman | |
| 2010/0040606 A1 | 2/2010 | Lantto et al. | |
| 2010/0266614 A1 | 10/2010 | Young et al. | |
| 2011/0076268 A1 | 3/2011 | Williamson et al. | |
| 2011/0097358 A1 | 4/2011 | Galarza et al. | |
| 2012/0164176 A1 | 6/2012 | Swanson et al. | |
| 2013/0034564 A1 | 2/2013 | Kauvar et al. | |
| 2014/0037648 A1 | 2/2014 | Corti | |
| 2014/0044719 A1 | 2/2014 | Williamson et al. | |

FOREIGN PATENT DOCUMENTS

| | | |
|---|---|---|
| EP | 0854730 A1 | 7/2011 |
| EP | 2341075 A1 | 7/2011 |
| WO | 96/05229 A1 | 2/1996 |
| WO | 00/069462 A1 | 11/2000 |
| WO | WO 01/051673 A1 | 7/2001 |
| WO | 11/020079 A1 | 2/2011 |
| WO | WO 14/121021 A1 | 8/2014 |

(Continued)

OTHER PUBLICATIONS

Johnson et al., The Journal of Infectious Diseases, vol. 180, Issue 1, Jul. 1, 1999, pp. 35-40.*
Paul, Fundamental Immunology, 3 rd Edition, 1993, pp. 292-295.*
Rudikoff et al (Proc. Natl. Acad. Sci. USA, 79:1979-1983, Mar. 1982.*
Coleman P. M. (Research in Immunology, 145:33-36, 1994.*
Weisshaar et al., DNA Cell Biol. Aug. 2015;34(8):505-10.*
Arbiza et al., "Characterization of two antigenic sites recognized by neutralizing monoclonal antibodies directed against the fusion glycoprotein of human respiratory syncytial virus," Journal of General Virology, 73:2225-2234, (1992).

(Continued)

*Primary Examiner* — Shanon A. Foley
*Assistant Examiner* — Myron G Hill
(74) *Attorney, Agent, or Firm* — Schwabe, Williamson & Wyatt PC; Veronica Mallon

(57) ABSTRACT

The present invention provides fully human antibodies that bind to respiratory syncytial virus F protein, compositions comprising the antibodies and methods of use. The antibodies of the invention are useful for preventing fusion of the virus with the cell membrane and preventing cell to cell spread of the virus, thereby providing a means of preventing the infection, or treating a patient suffering from the infection and ameliorating one or more symptoms or complications associated with the viral infection. The antibodies may also be useful for diagnosis of an infection by RSV.

26 Claims, 2 Drawing Sheets

Specification includes a Sequence Listing.

(56) References Cited

FOREIGN PATENT DOCUMENTS

WO     WO 14/159822 A2     10/2014
WO     WO 15/010792 A1     1/2015

OTHER PUBLICATIONS

Chintha et al., "A novel, highly potent, fully human anti-RSV-F monoclonal antibody for RSV prevention," Regeneron Pharmaceuticals, 9th International Respiratory Syncytial Virus Symposium, Poster No. 64, 1 Page, (2014).
Geevarghese et al., "Antibodies for prevention and treatment of respiratory syncytial virus infections in children," Antiviral Therapy, 17:201-211, (2012).
Lanari et al., "Clinical and Pharmacological Aspects of Immunoprophylaxis for Respiratory Syncytial Virus Infection in High-Risk Infants," Current Drug Metabolism, 14:216-225, (2013).
McLellan et al., "Structural basis of respiratory syncytial virus neutralization by motavizumab," Nature Structural & Molecular Biology, 17(2):248-250, (2010).
Murray et al., "Preventing severe respiratory syncytial virus disease: passive, active immunisation and new antivirals," Arch Dis Child, 99:469-473, (2014).
Rodriguez et al., "Respiratory syncytial virus: How, why and what to do," Journal of Infection, 68:S115-S118, (2014).
Swanson et al., "Structural basis for immunization with postfusion respiratory syncytial virus fusion F glycoprotein (RSV F) to elicit high neutralizing antibody titers," PNAS, 108(23):9619-9624, (2011).
Wu et al., "Characterization of the epitope for anti-human respiratory syncytial virus F protein monoclonal antibody 101F using synthetic peptides and genetic approaches," Journal of General Virology, 88:2719-2723, (2007).
Wu et al., "Development of Motavizumab, an Ultra-potent Antibody for the Prevention of Respiratory Syncytial Virus Infection in the Upper and Lower Respiratory Tract," J. Mol. Biol., 368(3):652-665, (2007).
U.S. Appl. No. 14/207,797, Final Office Action dated Feb. 19, 2016.
U.S. Appl. No. 14/207,797, Non-Final Office Action dated Jun. 29, 2015.
U.S. Appl. No. 14/207,797, Notice of Allowance dated May 5, 2016.
U.S. Appl. No. 14/207,797, Requirement for Restriction/Election dated Mar. 31, 2015.
WIPO Application No. PCT/US2014/025259, PCT International Preliminary Report on Patentability dated Sep. 24, 2015.
WIPO Application No. PCT/US2014/025259, PCT International Search Report and Written Opinion of the International Searching Authority dated Nov. 26, 2014.
GenBank: Accession No. 3KPE_A, "Chain A. Solution Structure of the Respiratory Suncytial Virus (Rsv)six-Helix Bundle Complexed With Tmc353121, a Small-Molecule Inhibitor of Rsv" Oct. 9, 2012.
GenBank: Accession No. 6093794, "Sequence 127 from U.S. Pat. No. 6,258,782" Oct. 17, 2001.
GenBank: Accession No. AAA54016, "Sequence 1 from patent WO 8905823" Dec. 2, 1994.
GenBank: Accession No. AAB38516, "fusion protein [Human respiratory syncytial virus]" Dec. 12, 1996.
GenBank: Accession No. AAB38520, "fusion protein [Human respiratory syncytial virus]" Dec. 12, 1996.
GenBank: Accession No. AAE18953, "Sequence 2 from U.S. Pat. No. 5,843,913" Sep. 29, 1999.
GenBank: Accession No. AAE32209, "Sequence 6 from U.S. Pat. No. 5,968,776" Aug. 31, 2000.
GenBank: Accession No. AAE46892, "Sequence 131 from U.S. Pat. No. 6,093,794" Feb. 14, 2001.
GenBank: Accession No. AAE46896, "Sequence 135 from U.S. Pat. No. 6,093,794" Feb. 14, 2001.
GenBank: Accession No. AAE76174, "Sequence 66 from U.S. Pat. No. 6,258,782" Oct. 17, 2001.
GenBank: Accession No. AAE76235, "Sequence 127 from U.S. Pat. No. 6,258,782" Oct. 17, 2001.
GenBank: Accession No. AAN98411, "Sequence 219 from U.S. Pat. No. 6,479,055" Dec. 20, 2002.
GenBank: Accession No. AAR63347, "Sequence 1816 from U.S. Pat. No. 6,623,741" Dec. 18, 2003.
GenBank: Accession No. AAR63395, "Sequence 1865 from U.S. Pat. No. 6,623,741" Dec. 18, 2003.
GenBank: Accession No. AAR63396, "Sequence 1866 from U.S. Pat. No. 6,623,741" Dec. 18, 2003.
GenBank: Accession No. AAR63412, "Sequence 1882 from U.S. Pat. No. 6,623,741" Dec. 18, 2003.
GenBank: Accession No. AAX23994, "usion protein [Human respiratory syncytial virus]" Jul. 5, 2005.
GenBank: Accession No. ABY14799, "Sequence 117 from U.S. Pat. No. 7,306,906" Dec. 14, 2007.
GenBank: Accession No. ACW43285, "High Affinity Antibodies to Human IL-6 Receptor", U.S. Pat. No. 7,582,298 Sep. 1, 2009.
GenBank: Accession No. ADL82794, "Sequence 29 from U.S. Pat. No. 7,700,720" Aug. 13, 2010.
GenBank: Accession No. AFG79656, "Sequence 3 from U.S. Pat. No. 8,137,921" Apr. 3, 2012.
GenBank: Accession No. AFG80011, "Sequence 69 from U.S. Pat. No. 7,582,298" Sep. 24, 2009.
GenBank: Accession No. CA158726, "unnamed protein product, partial [synthetic construct]" Feb. 23, 2005.
GenBank: Accession No. CAR98254, "Sequence 14 from U.S. Pat. No. 8,137,933" Apr. 3, 2012.
GenBank: Accession No. CBX54293, "unnamed protein product [synthetic construct]" Nov. 2, 2010.

* cited by examiner

SEQUENCE LISTING

<160> NUMBER OF SEQ ID NOS: 364

<210> SEQ ID NO 1
<211> LENGTH: 366
<212> TYPE: DNA
<213> ORGANISM: Artificial Sequence
<220> FEATURE:

-continued

<223> OTHER INFORMATION: Synthetic

<400> SEQUENCE: 1

```
caggtgcagc tggtgcagtc tgggctgag gtgaagaagc ctgggtcctc ggtgaaggtc      60
tcctgcaagg cttctggagg caccctcagt aataacgctt tcagctgggt gcgacaggcc    120
cctggacaag ggcttgagtg gttgggaggg ttcaacccga tctttgatac tgcaaactac    180
gcgcaaaagt tccagggcag aatcacgatc accctggacg catccacggg cacagtctac    240
atggaactga gcagcctgag atctgaggac acgggcgtgt attactgcgc gggaactggg    300
gcccattttg agttctgggg ccagggaacc ctggtcaccg tctcctcagc ctccaccaag    360
ggccca                                                                366
```

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Leu Ser Asn Asn
            20                  25                  30
Ala Phe Ser Trp Val Arg Gln Ala Pro Gly Gln Gly Leu Glu Trp Leu
        35                  40                  45
Gly Gly Phe Asn Pro Ile Phe Asp Thr Ala Asn Tyr Ala Gln Lys Phe
    50                  55                  60
Gln Gly Arg Ile Thr Ile Thr Leu Asp Ala Ser Thr Gly Thr Val Tyr
65                  70                  75                  80
Met Glu Leu Ser Ser Leu Arg Ser Glu Asp Thr Gly Val Tyr Tyr Cys
                85                  90                  95
Ala Gly Thr Gly Ala His Phe Glu Phe Trp Gly Gln Gly Thr Leu Val
            100                 105                 110
Thr Val Ser Ser Ala Ser Thr Lys Gly Pro
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggaggcaccc tcagtaataa cgct                                             24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Gly Thr Leu Ser Asn Asn Ala
 1               5
```

<210> SEQ ID NO 5

```
<211> LENGTH: 24
<212> TYPE: DNA
<213> ORGANISM: Artificial Sequence
<220> FEATURE:
<223> OTHER INFORMATION: Synthetic

<400> SEQUENCE: 5
ttcaacccga tctttgatac tgca                                              24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asn Pro Ile Phe Asp Thr Ala
  1               5

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
gcgggaactg gggcccattt tgagttc                                           27

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Ala Gly Thr Gly Ala His Phe Glu Phe
  1               5

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc      60
atcacttgcc ggacaagtca gagcattagc acctatttaa attggtatca gcagaaacca     120
ggaaaagccc ctaagttcct gatctatgct gcatccacct acaaagtggg gtcccatca     180 aggttcagtg gcagtggatc tcggacagat ttcactctca ccatcagcag tctgcaacct     240
gaagattttg caacttacta ctgtcaacag agtgtcagtg tcccgtacac ttttggccag     300
gggaccaagc tggagatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10
```

-continued

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Thr Tyr
            20                  25                  30

Leu Asn Trp Tyr Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Ser Val Ser Val Pro Tyr
                85                  90                  95

Thr Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcacctat                                              18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Thr Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                         9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagagtg tcagtgtccc gtacact         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ser Val Ser Val Pro Tyr Thr
1               5

<210> SEQ ID NO 17
<211> LENGTH: 366
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctggagggtc cctgagactc       60
tcctgtgcag cgtctggatt caccttcaat agttatggca tgcactgggt ccgccaggct      120
ccaggcaagg ggctggagtg gtgacattc atatggtctg atggaagtaa taaatattat       180
ttagactccg tgaagggccg attcaccatc tccagagaca attccaagaa cacactgtat      240
ctgcaaatga acagcctgag agccgaggac acggctgtat attactgtgc gagaagtgga      300
ctagcctcct attattata cggtatggac gtctggggcc aagggaccac ggtcaccgtc      360
tcctca                                                                  366

<210> SEQ ID NO 18
<211> LENGTH: 122
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Tyr
            20                  25                  30

Gly Met His Trp Val Arg Gln Ala Pro Gly Lys Gly Leu Glu Trp Val
        35                  40                  45

Thr Phe Ile Trp Ser Asp Gly Ser Asn Lys Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Leu Ala Ser Tyr Tyr Tyr Gly Met Asp Val Trp
            100                 105                 110

Gly Gln Gly Thr Thr Val Thr Val Ser Ser
        115                 120

<210> SEQ ID NO 19
<211> LENGTH: 24

<212> TYPE: DNA
<213> ORGANISM: Artificial Sequence
<220> FEATURE:
<223> OTHER INFORMATION: Synthetic

<400> SEQUENCE: 19
ggattcacct tcaatagtta tggc                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Asn Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atatggtctg atggaagtaa taaa                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Trp Ser Asp Gly Ser Asn Lys
1               5

<210> SEQ ID NO 23
<211> LENGTH: 45
<212> TYPE: DNA
<213> ORGANISM: Artificial Sequence
<220> FEATURE:
<223> OTHER INFORMATION: Synthetic

<400> SEQUENCE: 23
gcgagaagtg gactagcctc ctattattat tacggtatgg acgtc                   45

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ala Arg Ser Gly Leu Ala Ser Tyr Tyr Tyr Tyr Gly Met Asp Val
1               5                   10                  15

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatggt gcatccagtt tgcaaagtgg ggtcccgtca   180
aggttcagcg gcagtggatc tgggacagaa ttcactctca caatcagcag cctgcagcct   240
gaagattttg ccacttattc ctgtctacag cataatagtt acccgtggac gttcggccaa   300
gggaccaagg tggaaatcaa a                                             321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Ser Cys Leu Gln His Asn Ser Tyr Pro Trp
                 85                  90                  95

Thr Phe Gly Gln Gly Thr Lys Val Glu Ile Lys
                100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagggcatta gaaatgat                                                  18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Gly Ile Arg Asn Asp
  1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

```
<400> SEQUENCE: 29 ggtgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Gly Ala Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacagcata atagttaccc gtggacg                                         27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His Asn Ser Tyr Pro Trp Thr
 1               5

<210> SEQ ID NO 33
<211> LENGTH: 366
<212> TYPE: DNA
<213> ORGANISM: Artificial Sequence
<220> FEATURE:
<223> OTHER INFORMATION: Synthetic

<400> SEQUENCE: 33
caggtgcagc tggtggagtc tgggggaggc gtggtccagc ctggggaggtc cctgagactc     60 tcctgtgcag cgtcgggatt caccttcagt agttatggca tgcactgggt ccgccaggct    120
ccaggcaagg ggctggagtg gtggtatttt ctatggtatg atggaagtaa taaacactat    180
gcagactccg tgaagggccg attcaccatc tccagagaca attccaagaa cacattgtat    240
ttgcaaatga atagtctgag agccgaggac acggctgtat attactgtgc gagaagtgga    300
ctagcctcct attattatta cagtatggac gtctggggcc aagggaccac ggtcaccgtc    360
tcctca                                                              366

<210> SEQ ID NO 34
<211> LENGTH: 122
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Val Phe Leu Trp Tyr Asp Gly Ser Asn Lys His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Leu Ala Ser Tyr Tyr Tyr Ser Met Asp Val Trp
             100                 105                 110

Gly Gln Gly Thr Thr Val Thr Val Ser Ser
         115                 120
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct tcagtagtta tggc                                        24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

```
Gly Phe Thr Phe Ser Ser Tyr Gly
 1               5
```

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
ctatggtatg atggaagtaa taaa                                        24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Leu Trp Tyr Asp Gly Ser Asn Lys
 1               5
```

<210> SEQ ID NO 39
<211> LENGTH: 45
<212> TYPE: DNA
<213> ORGANISM: Artificial Sequence
<220> FEATURE:
<223> OTHER INFORMATION: Synthetic

<400> SEQUENCE: 39
gcgagaagtg gactagcctc ctattattat tacagtatgg acgtc                     45

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

Ala Arg Ser Gly Leu Ala Ser Tyr Tyr Tyr Ser Met Asp Val
1               5                   10                  15

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctcc ctgtctgcat ctgtaggaga cagagtcacc     60
atcacttgcc gggcaagtca gggcattaga aatgatttag cctggtatca gcagaaacca    120
gggaaagccc ctaagcgcct gatctatggt gcatccagtt tacacagtgg ggtcccatca    180
aggttcagcg gcagtggatc tgggacagaa ttcactctca caatcagcag cctgcagcct    240
gaagattttg caacttattc ctgtctacag cataatagtt acccgtggac gttcggccaa    300
gggaccaagg tggaaatcaa a                                              321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Ala Trp Tyr Gln Gln Lys Pro Gly Lys Ala Pro Lys Arg Leu Ile
        35                  40                  45

Tyr Gly Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Ser Cys Leu Gln His Asn Ser Tyr Pro Trp
                85                  90                  95

Thr Phe Gly Gln Gly Thr Lys Val Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

```
cagggcatta gaaatgat                                              18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Gly Ile Arg Asn Asp
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ggtgcatcc                                                         9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Gly Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
ctacagcata atagttaccc gtggacg                                    27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Gln His Asn Ser Tyr Pro Trp Thr
 1               5

<210> SEQ ID NO 49
<211> LENGTH: 354
<212> TYPE: DNA
<213> ORGANISM: Artificial Sequence
<220> FEATURE:
<223> OTHER INFORMATION: Synthetic

<400> SEQUENCE: 49
caggtgcagc tggtgcagtc tggggctgag gtgaagaagc ctggggcctc agtgaaggtc    60
tcctgcaagg cttctggata caccctcacc ggctattatc tacactgggt gcgacaggcc   120
```

```
cctggacaag ggcttgagtg gatgggatgg atcaaccctc ccagtggtgg cacaaactat      180
gcacagaagt tcagggcag ggtcaccatg accagggaca cgtccatcag tgcagccttc       240
atggagctga gtaggctgag atctgacgac acggccgtgt atcactgtgc gagagaattt      300
tggccccacg gtatggacgt ctggggccaa gggaccacgg tcaccgtctc ctca            354
```

<210> SEQ ID NO 50
<211> LENGTH: 118
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Gly Tyr
            20                  25                  30

Tyr Leu His Trp Val Arg Gln Ala Pro Gly Gln Gly Leu Glu Trp Met
        35                  40                  45

Gly Trp Ile Asn Pro Thr Ser Gly Gly Thr Asn Tyr Ala Gln Lys Phe
    50                  55                  60

Gln Gly Arg Val Thr Met Thr Arg Asp Thr Ser Ile Ser Ala Ala Phe
65                  70                  75                  80

Met Glu Leu Ser Arg Leu Arg Ser Asp Asp Thr Ala Val Tyr His Cys
                85                  90                  95

Ala Arg Glu Phe Trp Pro His Gly Met Asp Val Trp Gly Gln Gly Thr
            100                 105                 110

Thr Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggatacaccc tcaccggcta ttat                                             24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Tyr Thr Leu Thr Gly Tyr Tyr
1               5
```

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53

```
atcaacccta ccagtggtgg caca                                             24
```

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Asn Pro Thr Ser Gly Gly Thr
 1               5

<210> SEQ ID NO 55
<211> LENGTH: 33
<212> TYPE: DNA
<213> ORGANISM: Artificial Sequence
<220> FEATURE:
<223> OTHER INFORMATION: Synthetic

<400> SEQUENCE: 55
gcgagagaat tttggcccca cggtatggac gtc                                  33

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Ala Arg Glu Phe Trp Pro His Gly Met Asp Val
 1               5                  10

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccatcctcc ctgtctgcat ctgtaggaga cagagtcacc      60
atcacttgcc gggcaagtca ggccattaga aatgatttag ctggtatca gcagaaacca     120 gggaaagccc ctaagctcct gatctatgct tcatccagtt tacaaagtgg ggtcccttca    180
aggttcagcg gcagtggatc tggcacagat ttcactctca ccatcagcag cctgcagcct    240
gaagattttg caacttatta ctgtcttgca gattacaaat acacgtggac gttcggccaa    300
gggaccaagg tggaaatcaa a                                              321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Leu Leu Ile
        35                  40                  45

```
Tyr Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Ala Asp Tyr Lys Tyr Thr Trp
                 85                  90                  95

Thr Phe Gly Gln Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggccatta gaaatgat                                              18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ala Ile Arg Asn Asp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gcttcatcc                                                         9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ser Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
cttgcagatt acaaatacac gtggacg                                    27

<210> SEQ ID NO 64
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 64

Leu Ala Asp Tyr Lys Tyr Thr Trp Thr
 1               5

<210> SEQ ID NO 65
<211> LENGTH: 378
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtacacc cggggggggtc cctgagactc      60 tcctgtgaag cctctggatt cacacttagc agccatgtca tgagctgggt ccgccaggtt     120
ccaggcaagg ggctggagtg ggtctcacgt atcagtggtc ctggtggtag tacaaagtat     180
gcggactccg tgcagggccg gttcaccacc tccagagaca actccaagaa caccctgtat     240
ctacaaatga acagcctgat agccgaggac tcggccgcat attactgtgc gaaagggggg     300
ggatatagtg gctacgattg ggactttat  tacggtatgg acgtctgggg ccaagggacc     360
acggtcaccg tctcctca                                                   378

<210> SEQ ID NO 66
<211> LENGTH: 126
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val His Pro Gly Gly
 1               5                  10                  15

Ser Leu Arg Leu Ser Cys Glu Ala Ser Gly Phe Thr Leu Ser Ser His
            20                  25                  30

Val Met Ser Trp Val Arg Gln Val Pro Gly Lys Gly Leu Glu Trp Val
        35                  40                  45

Ser Arg Ile Ser Gly Pro Gly Gly Ser Thr Lys Tyr Ala Asp Ser Val
    50                  55                  60

Gln Gly Arg Phe Thr Thr Ser Arg Asp Asn Ser Lys Asn Thr Leu Tyr
65                  70                  75                  80

Leu Gln Met Asn Ser Leu Ile Ala Glu Asp Ser Ala Ala Tyr Tyr Cys
                85                  90                  95

Ala Lys Gly Gly Gly Tyr Ser Gly Tyr Asp Trp Asp Phe Tyr Tyr Gly
            100                 105                 110

Met Asp Val Trp Gly Gln Gly Thr Thr Val Thr Val Ser Ser
        115                 120                 125

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacac ttagcagcca tgtc                                             24
```

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Leu Ser Ser His Val
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
atcagtggtc ctggtggtag taca                                            24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ser Gly Pro Gly Gly Ser Thr
 1               5

<210> SEQ ID NO 71
<211> LENGTH: 57
<212> TYPE: DNA
<213> ORGANISM: Artificial Sequence
<220> FEATURE:
<223> OTHER INFORMATION: Synthetic

<400> SEQUENCE: 71
gcgaaagggg ggggatatag tggctacgat tgggactttt attacggtat ggacgtc       57

<210> SEQ ID NO 72
<211> LENGTH: 19
<212> TYPE: PRT
<213> ORGANISM: Artificial Sequence
<220> FEATURE:
<223> OTHER INFORMATION: Synthetic

<400> SEQUENCE: 72

Ala Lys Gly Gly Gly Tyr Ser Gly Tyr Asp Trp Asp Phe Tyr Tyr Gly
 1               5                  10                  15

Met Asp Val

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcttcc gtgtctgcat ctgtaggaga cagagtcacc     60
atcacttgtc gggcgagtca gggtattagc agctggttag cctggtatca gcagaaacca   120

```
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag actaacagtt ccctctcac tttcggcgga     300 gggaccaaag tggatatcaa a                                               321
```

```
<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Asp Ile Lys
            100                 105

```
<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagggtatta gcagctgg                                                   18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76
```

Gln Gly Ile Ser Ser Trp
1               5

```
<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                              9

<210> SEQ ID NO 78
<211> LENGTH: 3
```

<212> TYPE: PRT
<213> ORGANISM: Artificial Sequence
<220> FEATURE:
<223> OTHER INFORMATION: Synthetic

<400> SEQUENCE: 78

Ala Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagacta acagtttccc tctcact                              27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Thr Asn Ser Phe Pro Leu Thr
 1               5

<210> SEQ ID NO 81
<211> LENGTH: 366
<212> TYPE: DNA
<213> ORGANISM: Artificial Sequence
<220> FEATURE:
<223> OTHER INFORMATION: Synthetic

<400> SEQUENCE: 81
caggtgcagc tggtgcagtc tggggctgag gtgaagaagt ctggggcctc ggtgaaggtc      60
tcctgcaagg cttctggagg caccttcagc agctatgcta tcagctgggt gcgacaggcc    120
ccgggacaag gcttgagtg gatgggaggg atcatcccta tctttggtac aggaaattac    180
gcacagaagt tccagggcag agtcacgatt accacggacg aatccacgag cacagcctat    240
atggagctga gcagcctgag atctgaggac acggccgtgt attattgtgc gagagatagc    300
agctcgtccc cgaggtacta cggtatggac gtctggggcc acgggaccac ggtcaccgtc    360
tcctca                                                              366

<210> SEQ ID NO 82
<211> LENGTH: 122
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Gln Ser Gly Ala Glu Val Lys Lys Ser Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Gly Asn Tyr Ala Gln Lys Phe

```
                50                  55                  60
Gln Gly Arg Val Thr Ile Thr Thr Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Ser Ser Pro Arg Tyr Tyr Gly Met Asp Val Trp
            100                 105                 110

Gly His Gly Thr Thr Val Thr Val Ser Ser
        115                 120
```

```
<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggaggcacct tcagcagcta tgct                                    24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84
```

```
Gly Gly Thr Phe Ser Ser Tyr Ala
 1               5
```

```
<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
atcatcccta tctttggtac agga                                    24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86
```

```
Ile Ile Pro Ile Phe Gly Thr Gly
 1               5
```

```
<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
gcgagagata gcagctcgtc cccgaggtac tacggtatgg acgtc              45

<210> SEQ ID NO 88
<211> LENGTH: 15
```

<212> TYPE: PRT
<213> ORGANISM: Artificial Sequence
<220> FEATURE:
<223> OTHER INFORMATION: Synthetic

<400> SEQUENCE: 88

Ala Arg Asp Ser Ser Ser Pro Arg Tyr Tyr Gly Met Asp Val
1               5                   10                  15

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gaaattgtgt tgacacagtc tccagccacc ctgtctttgt ctccagggga aagagccacc    60
ctctcctgca gggccagtca gagtgttacc agctacttag cctggtacca acagaaacct   120
ggccaggctc ccaggctcct catctatgat gtatccaaga gggccactgg catcccagcc   180
aggttcagtg gcagtgggtc tgggacagac ttcactctca ccatcagcag cctagagcct   240
gaagattttg caacttatta ttgtcagcag cgtagcaact ggcctcccac cttcggccaa   300
gggacacgac tggagattaa a                                              321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ser Tyr
            20                  25                  30

Leu Ala Trp Tyr Gln Gln Lys Pro Gly Gln Ala Pro Arg Leu Leu Ile
        35                  40                  45

Tyr Asp Val Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Arg Ser Asn Trp Pro Pro
                85                  90                  95

Thr Phe Gly Gln Gly Thr Arg Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagtgtta ccagctac                                                   18

<210> SEQ ID NO 92
<211> LENGTH: 6
<212> TYPE: PRT

```
<213> ORGANISM: Artificial Sequence
<220> FEATURE:
<223> OTHER INFORMATION: Synthetic

<400> SEQUENCE: 92

Gln Ser Val Thr Ser Tyr
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gatgtatcc                                                                  9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Asp Val Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
cagcagcgta gcaactggcc tcccacc                                             27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Arg Ser Asn Trp Pro Pro Thr
 1               5

<210> SEQ ID NO 97
<211> LENGTH: 375
<212> TYPE: DNA
<213> ORGANISM: Artificial Sequence
<220> FEATURE:
<223> OTHER INFORMATION: Synthetic

<400> SEQUENCE: 97
gaggtgcagc tggtggagtc tgggggaggc ttggtccagc ctgggggtc cctgagactc           60 tcctgtgaag cctctggatt cacctttagt acctattgga tgagttgggt ccgccaggct         120
ccagggaagg ggctagagtg ggtggccaac ataaaacaag atggaagtgt gaaatacttt         180
gtggactctg tgaagggccg attcaccgtc tccagagaca cgccaagaa ctccctgtat         240 ctgcaaatga acagcctgag agccgaggac acggctctgt atcactgtgc gagagagagg         300
```

```
cacagaggga gctactacgg ctactacgac ggtatggacg tctggggcca agggaccacg    360
gtcaccgtct cctca                                                     375
```

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Gly Leu Val Gln Pro Gly Gly
  1               5                  10                  15

Ser Leu Arg Leu Ser Cys Glu Ala Ser Gly Phe Thr Phe Ser Thr Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Val Lys Tyr Phe Val Asp Ser Val
     50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Glu Arg His Arg Gly Ser Tyr Tyr Gly Tyr Tyr Asp Gly Met
            100                 105                 110

Asp Val Trp Gly Gln Gly Thr Thr Val Thr Val Ser Ser
        115                 120                 125
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct ttagtaccta ttgg                                           24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Ser Thr Tyr Trp
  1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101

```
ataaaacaag atggaagtgt gaaa                                           24
```

<210> SEQ ID NO 102
<211> LENGTH: 8
<212> TYPE: PRT

```
<213> ORGANISM: Artificial Sequence
<220> FEATURE:
<223> OTHER INFORMATION: Synthetic

<400> SEQUENCE: 102

Ile Lys Gln Asp Gly Ser Val Lys
 1               5

<210> SEQ ID NO 103
<211> LENGTH: 54
<212> TYPE: DNA
<213> ORGANISM: Artificial Sequence
<220> FEATURE:
<223> OTHER INFORMATION: Synthetic

<400> SEQUENCE: 103
gcgagagaga ggcacagagg gagctactac ggctactacg acggtatgga cgtc          54

<210> SEQ ID NO 104
<211> LENGTH: 18
<212> TYPE: PRT
<213> ORGANISM: Artificial Sequence
<220> FEATURE:
<223> OTHER INFORMATION: Synthetic

<400> SEQUENCE: 104

Ala Arg Glu Arg His Arg Gly Ser Tyr Tyr Gly Tyr Tyr Asp Gly Met
 1               5                  10                  15

Asp Val

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc     60
atcacttgcc gggcaagtca aacattgac atctatttaa attggtatca ggagaggcca    120
gggaaagccc ctaatctcct gatctatgct gcatccagtt tgcaaagtgg ggtcccatca   180
aggttcagtg gcagtggatc tgggacagat tcactctca ccatcagtag tctgcaacct    240
gaagattttg caacttacta ctgtcaacag agttacaata ccccgttcac tttcggcggc   300
gggaccaagg tggagatcaa a                                             321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Asp Ile Tyr
                20                  25                  30

Leu Asn Trp Tyr Gln Glu Arg Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Phe
                85                  90                  95

Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caaaacattg acatctat                                                 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asn Ile Asp Ile Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                            9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagagtt acaatacccc gttcact                                       27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Asn Thr Pro Phe Thr
 1               5

<210> SEQ ID NO 113
<211> LENGTH: 369
<212> TYPE: DNA
<213> ORGANISM: Artificial Sequence
<220> FEATURE:
<223> OTHER INFORMATION: Synthetic

<400> SEQUENCE: 113
gaagtgcagc tggtggagtc tgggggaggc ttggtacagc ctggcaggtc cctgagactc     60
tcctgtgcag cctctggatt cacctttgat gattatgcca tgcactgggt ccggcaaact    120
ccagggaagg gcctggagtg gatctcaggt attagttgga gtagtggtac catagtctat    180
gcagactctg tgaagggccg cttcaccatc tccagagaca acgccaagaa ctccctgtat    240
ctgcaaatga acagtctgag aggtgaggac acggccttgt atcactgtgc aaaagatggg    300
tataggtgga agtcctactc gtacggtttg gacgtctggg gccaagggac cacggtcacc    360
gtctcctca                                                           369

<210> SEQ ID NO 114
<211> LENGTH: 123
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Ile
        35                  40                  45

Ser Gly Ile Ser Trp Ser Ser Gly Thr Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Leu Tyr His Cys
                85                  90                  95

Ala Lys Asp Gly Tyr Arg Trp Lys Ser Tyr Ser Tyr Gly Leu Asp Val
            100                 105                 110

Trp Gly Gln Gly Thr Thr Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttgatgatta tgcc                                           24

<210> SEQ ID NO 116
<211> LENGTH: 8

<212> TYPE: PRT
<213> ORGANISM: Artificial Sequence
<220> FEATURE:
<223> OTHER INFORMATION: Synthetic

<400> SEQUENCE: 116

Gly Phe Thr Phe Asp Asp Tyr Ala
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attagttgga gtagtggtac cata                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Trp Ser Ser Gly Thr Ile
1               5

<210> SEQ ID NO 119
<211> LENGTH: 48
<212> TYPE: DNA
<213> ORGANISM: Artificial Sequence
<220> FEATURE:
<223> OTHER INFORMATION: Synthetic

<400> SEQUENCE: 119
gcaaaagatg ggtataggtg aagtcctac tcgtacggtt tggacgtc                 48

<210> SEQ ID NO 120
<211> LENGTH: 16
<212> TYPE: PRT
<213> ORGANISM: Artificial Sequence
<220> FEATURE:
<223> OTHER INFORMATION: Synthetic

<400> SEQUENCE: 120

Ala Lys Asp Gly Tyr Arg Trp Lys Ser Tyr Ser Tyr Gly Leu Asp Val
1               5                   10                  15

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gaaatagtga tgacgcagtc tccagccacc ctctctttgt ctccagggga aagagccacc    60
ctctcctgca ggcccagtca gagtgttatc aataacttag cctggtacca gcagaaacct   120
ggccaggctc ccagactcct catctttggt gcatcctcca gggccactgg tatcccagcc   180
agattcagtg gcagtgggtc tgggacagag tttactctca ccatcagcag cctgcagtct   240
gaagattttg cactttatta ctgtcagcag tataataact ggccgctcac cttcggcgga   300
gggaccaagg tggagatcaa a                                                      321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Glu Ile Val Met Thr Gln Ser Pro Ala Thr Leu Ser Leu Ser Pro Gly
 1               5                  10                  15

Glu Arg Ala Thr Leu Ser Cys Arg Pro Ser Gln Ser Val Ile Asn Asn
            20                  25                  30

Leu Ala Trp Tyr Gln Gln Lys Pro Gly Gln Ala Pro Arg Leu Leu Ile
        35                  40                  45

Phe Gly Ala Ser Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagtgtta tcaataac                                                           18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Val Ile Asn Asn
 1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 ggtgcatcc                                                                      9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Gly Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
cagcagtata ataactggcc gctcacc                                             27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Asn Asn Trp Pro Leu Thr
 1               5

<210> SEQ ID NO 129
<211> LENGTH: 369
<212> TYPE: DNA
<213> ORGANISM: Artificial Sequence
<220> FEATURE:
<223> OTHER INFORMATION: Synthetic

<400> SEQUENCE: 129
gaagtgcagc tggtggagtc tgggggagac ttggtacagc ctggcaggtc cctgagactc          60
tcctgtgtag cctctggatt cacctttgat gattatgcca tgcactgggt ccggcaagct         120
ccagggaagg gcctggagtg gtctcaggt gttagttgga gtggtagtac cgtaggctat          180
gcggactctg tgaagggccg attcaccgtc tccagagaca acgcccagaa atccctgtat         240
ctacaaatga acagtctgag agctgaggac acggccttgt attactgtgt aaaagacgcg         300
tataaatgga actactacta ctacggtttg acgtctgggg ccaagggac cacggtcacc          360 gtctcctca                                                                369

<210> SEQ ID NO 130
<211> LENGTH: 123
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Asp Leu Val Gln Pro Gly Arg
 1               5                  10                  15

Ser Leu Arg Leu Ser Cys Val Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Val Ser Trp Ser Gly Ser Thr Val Gly Tyr Ala Asp Ser Val
        50                  55                  60

Lys Gly Arg Phe Thr Val Ser Arg Asp Asn Ala Gln Lys Ser Leu Tyr
65                  70                  75                  80

```
Leu Gln Met Asn Ser Leu Arg Ala Glu Asp Thr Ala Leu Tyr Tyr Cys
            85                  90                  95

Val Lys Asp Ala Tyr Lys Trp Asn Tyr Tyr Tyr Gly Leu Asp Val
100                 105                 110

Trp Gly Gln Gly Thr Thr Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ttgatgatta tgcc         24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Phe Thr Phe Asp Asp Tyr Ala
1               5
```

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
gttagttgga gtggtagtac cgta         24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

```
Val Ser Trp Ser Gly Ser Thr Val
1               5
```

<210> SEQ ID NO 135
<211> LENGTH: 48
<212> TYPE: DNA
<213> ORGANISM: Artificial Sequence
<220> FEATURE:
<223> OTHER INFORMATION: Synthetic

<400> SEQUENCE: 135
gtaaaagacg cgtataaatg gaactactac tactacggtt tggacgtc         48

<210> SEQ ID NO 136
<211> LENGTH: 16
<212> TYPE: PRT
<213> ORGANISM: Artificial Sequence
<220> FEATURE:
<223> OTHER INFORMATION: Synthetic

<400> SEQUENCE: 136

Val Lys Asp Ala Tyr Lys Trp Asn Tyr Tyr Tyr Gly Leu Asp Val
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137

```
gaaatagtga tgacgcagtc tccagccacc ctgtctgtgt ctccagggga aagagccacc    60
ctctcctgca gggccagtca gactattctc agcaacttag cctggtacct acagaaacct   120
ggccaggctc ccaggctcct catctatggt gcatccacca gggccactgg tctcccagcc   180
aggttcagtg gcagtgggtc tgggacagag ttcactctca ccatcagcag cctgcagtct   240
gaagattttg cagtttatta ctgtcagcag tataataact ggcctctcac tttcggcgga   300
gggaccaagg tggagatcaa a                                            321
```

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Ile Leu Ser Asn
            20                  25                  30

Leu Ala Trp Tyr Leu Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagactattc tcagcaac                                                 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Thr Ile Leu Ser Asn
  1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 ggtgcatcc                                                                    9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

```
Gly Ala Ser
  1
```

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
cagcagtata ataactggcc tctcact                                                27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

```
Gln Gln Tyr Asn Asn Trp Pro Leu Thr
  1               5
```

<210> SEQ ID NO 145
<211> LENGTH: 369
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ttggtacagc ctggggggtc cctgagactc      60
tcctgtggag cctctggatt cacctttagg gactttgaca tgaattgggt ccgtcaggct     120
ccagggaggg gctggagtg gtctcaggt attggtggta gtggtggtaa cacatattac      180
gcagactccg tgaagggccg gttcaccata tccaggcaca attccaaaaa cacgctgttt     240
ctgcaaatga gcagcctgag agccgaggac acggccgttt attactgtgt gaaagatccc     300
tatggtgact ataggaacta ctacggtatg gacgtctggg gccaagggac cacggtcacc     360
gtctcctca                                                             369

<210> SEQ ID NO 146
<211> LENGTH: 123
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Arg Asp Phe
            20                  25                  30

Asp Met Asn Trp Val Arg Gln Ala Pro Gly Arg Gly Leu Glu Trp Val
        35                  40                  45

Ser Gly Ile Gly Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Ala Glu Asp Thr Ala Val Tyr Tyr Cys
                85                  90                  95

Val Lys Asp Pro Tyr Gly Asp Tyr Arg Asn Tyr Tyr Gly Met Asp Val
            100                 105                 110

Trp Gly Gln Gly Thr Thr Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct ttagggactt tgac                                          24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Arg Asp Phe Asp
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attggtggta gtggtggtaa caca                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Gly Gly Ser Gly Gly Asn Thr
1               5

<210> SEQ ID NO 151
<211> LENGTH: 48
<212> TYPE: DNA
<213> ORGANISM: Artificial Sequence
<220> FEATURE:
<223> OTHER INFORMATION: Synthetic

<400> SEQUENCE: 151
gtgaaagatc cctatggtga ctataggaac tactacggta tggacgtc         48

<210> SEQ ID NO 152
<211> LENGTH: 16
<212> TYPE: PRT
<213> ORGANISM: Artificial Sequence
<220> FEATURE:
<223> OTHER INFORMATION: Synthetic

<400> SEQUENCE: 152

Val Lys Asp Pro Tyr Gly Asp Tyr Arg Asn Tyr Tyr Gly Met Asp Val
1               5                   10                  15

<210> SEQ ID NO 153
<211> LENGTH: 333
<212> TYPE: DNA
<213> ORGANISM: Artificial Sequence
<220> FEATURE:
<223> OTHER INFORMATION: Synthetic

<400> SEQUENCE: 153
gatattgtga tgactcagtc tccactctcc ctgcccgtca cccctggaga gccggcctcc      60
atctcctgca ggtctagtca gagcctccta catagtaatg gatacaacta tttggattgg    120
tacctgcaga agccagggca gtctccacaa ctcctgatct atttgggttc taatcgggcc    180
tccggggtcc ctgacaggtt cagggggcagt ggatcagaca aggactttac actgaaaatc    240
agcagagtgg gggctgagga tgttggggtt tattactgca tgcaagctct acaaactatc    300
accttcggcc aagggacacg actggagatt aaa                                  333

<210> SEQ ID NO 154
<211> LENGTH: 111
<212> TYPE: PRT
<213> ORGANISM: Artificial Sequence
<220> FEATURE:
<223> OTHER INFORMATION: Synthetic

<400> SEQUENCE: 154

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Arg Gly Ser Gly Ser Asp Lys Asp Phe Thr Leu Lys Ile
65                  70                  75                  80

Ser Arg Val Gly Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys
            100                 105                 110

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
cagagcctcc tacatagtaa tggatacaac tat        33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Leu His Ser Asn Gly Tyr Asn Tyr
1               5                   10

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ttgggttct        9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Leu Gly Ser
1

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159
atgcaagctc tacaaactat cacc        24

<210> SEQ ID NO 160
<211> LENGTH: 8
<212> TYPE: PRT
<213> ORGANISM: Artificial Sequence
<220> FEATURE:
<223> OTHER INFORMATION: Synthetic

<400> SEQUENCE: 160

Met Gln Ala Leu Gln Thr Ile Thr
1               5

```
<210> SEQ ID NO 161
<211> LENGTH: 369
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttgggacagc ctgggggtc cctgagactc      60 tcctgtggag cctctggatt catgtttaga aactatgcca tgagttgggt ccgccaggct     120
ccagggaagg ggctggagtg ggtctcaact attcttgata gtggtgataa cacatattac     180
gcagactccg tgaagggccg gttcaccatc tccaggaca attccaagaa cacactgtat      240
ctgcaaatga acagcctgag agccgaggac acggccgttt attactgtgc gaaagatccc     300
tatggtgact acagggacta ctacggtatg gacgtctggg gccaagggac cacggtcacc     360
gtctcctca                                                              369

<210> SEQ ID NO 162
<211> LENGTH: 123
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Gly Gln Pro Gly Gly
 1               5                  10                  15

Ser Leu Arg Leu Ser Cys Gly Ala Ser Gly Phe Met Phe Arg Asn Tyr
            20                  25                  30

Ala Met Ser Trp Val Arg Gln Ala Pro Gly Lys Gly Leu Glu Trp Val
        35                  40                  45

Ser Thr Ile Leu Asp Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Tyr Gly Asp Tyr Arg Asp Tyr Tyr Gly Met Asp Val
            100                 105                 110

Trp Gly Gln Gly Thr Thr Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcatgt ttagaaacta tgcc                                              24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164
```

Gly Phe Met Phe Arg Asn Tyr Ala
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attcttgata gtggtgataa caca                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Leu Asp Ser Gly Asp Asn Thr
1               5

<210> SEQ ID NO 167
<211> LENGTH: 48
<212> TYPE: DNA
<213> ORGANISM: Artificial Sequence
<220> FEATURE:
<223> OTHER INFORMATION: Synthetic

<400> SEQUENCE: 167
gcgaaagatc cctatggtga ctacagggac tactacggta tggacgtc                48

<210> SEQ ID NO 168
<211> LENGTH: 16
<212> TYPE: PRT
<213> ORGANISM: Artificial Sequence
<220> FEATURE:
<223> OTHER INFORMATION: Synthetic

<400> SEQUENCE: 168

Ala Lys Asp Pro Tyr Gly Asp Tyr Arg Asp Tyr Tyr Gly Met Asp Val
1               5                   10                  15

<210> SEQ ID NO 169
<211> LENGTH: 333
<212> TYPE: DNA
<213> ORGANISM: Artificial Sequence
<220> FEATURE:
<223> OTHER INFORMATION: Synthetic

<400> SEQUENCE: 169
gatattgtga tgactcagtc tccactctcc ctgcccgtca cccctggaga gccggcctcc    60
atctcctgca ggtctagtca gagcctccta catagtaatg gatacaacta tttggattgg   120
tacctgcaga agccagggca gtctccgcaa ctcctgatct atttgggttc taatcgggcc   180
tccggggtcc ctgacaggtt caggggcagt ggatcaggca agactttac actgaaaatc    240 agcagagtgg aggctgagga tgttggactt tattactgca tgcaagctct acaaactatc   300
accttcggcc aagggacacg actggagatt aaa                                333

<210> SEQ ID NO 170
<211> LENGTH: 111
<212> TYPE: PRT

<213> ORGANISM: Artificial Sequence
<220> FEATURE:
<223> OTHER INFORMATION: Synthetic

<400> SEQUENCE: 170

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Arg Gly Ser Gly Ser Gly Lys Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Ile Thr Phe Gly Gly Gly Thr Arg Leu Glu Ile Lys
            100                 105                 110
```

<210> SEQ ID NO 171
<211> LENGTH: 33
<212> TYPE: DNA
<213> ORGANISM: Artificial Sequence
<220> FEATURE:
<223> OTHER INFORMATION: Synthetic

<400> SEQUENCE: 171
cagagcctcc tacatagtaa tggatacaac tat                                33

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172

```
Gln Ser Leu Leu His Ser Asn Gly Tyr Asn Tyr
 1               5                  10
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 ttgggttct                                                            9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

```
Leu Gly Ser
 1
```

<210> SEQ ID NO 175

```
<211> LENGTH: 24
<212> TYPE: DNA
<213> ORGANISM: Artificial Sequence
<220> FEATURE:
<223> OTHER INFORMATION: Synthetic

<400> SEQUENCE: 175
atgcaagctc tacaaactat cacc                                              24

<210> SEQ ID NO 176
<211> LENGTH: 8
<212> TYPE: PRT
<213> ORGANISM: Artificial Sequence
<220> FEATURE:
<223> OTHER INFORMATION: Synthetic

<400> SEQUENCE: 176

Met Gln Ala Leu Gln Thr Ile Thr
 1               5

<210> SEQ ID NO 177
<211> LENGTH: 384
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtgaagc cttcggagac cctgtccctc       60
acctgcactg tctctggtgg ctccatcagt ggttactact ggacctggat ccggcagccc      120
ccagggaagg gactggagtg gattggatat atctattaca gtggggccac caactacaac      180
ccctccctca gagtcgagt caccatatca ttagacacgt ccaagaacca gttctccctg      240
aaactgagct ctgtgaccgc tgcggacacg gccgtgtatt attgtgcgag agatgggaat      300
tacgatattt tgactggtta ttataactac cactattacg gcatggacgt ctggggccaa      360
gggaccacgg tcaccgtctc ctca                                             384

<210> SEQ ID NO 178
<211> LENGTH: 128
<212> TYPE: PRT
<213> ORGANISM: Artificial Sequence
<220> FEATURE:
<223> OTHER INFORMATION: Synthetic

<400> SEQUENCE: 178

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Gly Tyr
                20                  25                  30

Tyr Trp Thr Trp Ile Arg Gln Pro Pro Gly Lys Gly Leu Glu Trp Ile
            35                  40                  45

Gly Tyr Ile Tyr Tyr Ser Gly Ala Thr Asn Tyr Asn Pro Ser Leu Lys
        50                  55                  60

Ser Arg Val Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asn Tyr Asp Ile Leu Thr Gly Tyr Tyr Asn Tyr His Tyr
            100                 105                 110

Tyr Gly Met Asp Val Trp Gly Gln Gly Thr Thr Val Thr Val Ser Ser
```

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggtggctcca tcagtggtta ctac                                          24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Gly Ser Ile Ser Gly Tyr Tyr
1               5

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
atctattaca gtggggccac c                                             21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Ile Tyr Tyr Ser Gly Ala Thr
1               5

<210> SEQ ID NO 183
<211> LENGTH: 66
<212> TYPE: DNA
<213> ORGANISM: Artificial Sequence
<220> FEATURE:
<223> OTHER INFORMATION: Synthetic

<400> SEQUENCE: 183
gcgagagatg ggaattacga tattttgact ggttattata actaccacta ttacggcatg   60
gacgtc                                                              66

<210> SEQ ID NO 184
<211> LENGTH: 22
<212> TYPE: PRT
<213> ORGANISM: Artificial Sequence
<220> FEATURE:
<223> OTHER INFORMATION: Synthetic

<400> SEQUENCE: 184

Ala Arg Asp Gly Asn Tyr Asp Ile Leu Thr Gly Tyr Tyr Asn Tyr His
1               5                   10                  15

Tyr Tyr Gly Met Asp Val
            20

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcctca ctgtctgcat ctgtaggaga cagagtcacc      60
atcacttgtc gggcgagtca ggacattggt aattatttag cctggtttca gcagaaacca     120
gggaaagccc ctgagtccct gatctatgct gcatccattt acaaagtggg gtcccatca      180 aagttcagcg gcagtggatc tgggacagat ttcactctca ccatcagcag cctgcagcct     240
gaagattttg caacttatta ctgccaacag tataatactt tcccgtggac gttcggccaa     300
gggaccaagg tggaaatcaa a                                               321

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Ile Gly Asn Tyr
            20                  25                  30

Leu Ala Trp Phe Gln Gln Lys Pro Gly Lys Ala Pro Glu Ser Leu Ile
        35                  40                  45

Tyr Ala Ala Ser Ile Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Phe Pro Trp
                85                  90                  95

Thr Phe Gly Gln Gly Thr Lys Val Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
caggacattg gtaattat                                                   18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asp Ile Gly Asn Tyr

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc                                                                   9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacagtata atactttccc gtggacg                                              27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Thr Phe Pro Trp Thr
 1               5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
caggtgcagc tggtggagtc tgggggaggc ttggtcaagc ctggagggtc cctgaggctc        60
tcctgtgcag cctctggatt caccttcagt gactactaca tgacctggat ccgtcaggct       120
ccagggaggg gctggagtg gtttcatac attagtgata ctggcagtca cttatactac        180
gcagactctg tgaggggccg attcaccatc tccagggaca acgccaaaaa ctcactgtat       240
ctgcaaatga acaacctgag agccgaggac acggccgtat attactgtgc gcagatcag        300 gatggggaaa tggaactacg tttctttgac tactggggcc agggaaccct ggtcaccgtc       360
tcctca                                                                  366

<210> SEQ ID NO 194
<211> LENGTH: 122

<212> TYPE: PRT
<213> ORGANISM: Artificial Sequence
<220> FEATURE:
<223> OTHER INFORMATION: Synthetic

<400> SEQUENCE: 194

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Arg Gly Leu Glu Trp Val
        35                  40                  45

Ser Tyr Ile Ser Asp Thr Gly Ser His Leu Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr Tyr Cys
                85                  90                  95

Ala Arg Asp Gln Asp Gly Glu Met Glu Leu Arg Phe Phe Asp Tyr Trp
            100                 105                 110

Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct tcagtgacta ctac                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Ser Asp Tyr Tyr
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attagtgata ctggcagtca ctta                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Asp Thr Gly Ser His Leu

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgcgagatc aggatgggga aatggaacta cgtttctttg actac                45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Arg Asp Gln Asp Gly Glu Met Glu Leu Arg Phe Phe Asp Tyr
1               5                   10                  15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gaaatagtgt tgacgcagtc tccagccact ctgtctttgt ctccagggga aagaggcacc    60
ctctcctgca gggccagtca gagtattaac aactacttag cctggtacca gcagaaacct   120
ggccaggctc ccaggctcct catctttgat gcatccaaca gggccactgg catcccagcc   180
aggttcagtg gcagtgggtc tgggacagac ttcactctca ccatcagcag aatagagcct   240
gaagattttg cagtttatta ctgtcagcag cgtaccaact ggccgctcac tttcggcgga   300
gggaccaagg tggagatcaa a                                             321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Glu Ile Val Leu Thr Gln Ser Pro Ala Thr Leu Ser Leu Ser Pro Gly
1               5                   10                  15

Glu Arg Gly Thr Leu Ser Cys Arg Ala Ser Gln Ser Ile Asn Asn Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Ile Glu Pro
65                  70                  75                  80

Glu Asp Phe Ala Val Tyr Tyr Cys Gln Gln Arg Thr Asn Trp Pro Leu
                85                  90                  95

Thr Phe Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatta acaactac                                                 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Asn Asn Tyr
 1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gatgcatcc                                                            9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Asp Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
cagcagcgta ccaactggcc gctcact                                       27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Arg Thr Asn Trp Pro Leu Thr
 1               5

<210> SEQ ID NO 209
<211> LENGTH: 381

<212> TYPE: DNA
<213> ORGANISM: Artificial Sequence
<220> FEATURE:
<223> OTHER INFORMATION: Synthetic

<400> SEQUENCE: 209

```
caggtgcagc tgcaggagtc gggcccagga ctggtgaagc cttcggagac cctgtccctc    60
acctgcactg tctctggtgg cttcatcagt aattactact ggagctggat ccggcagccc   120
ccagggaagg gactggagtg gattggatat atctattata gtgggagcac caagtacaac   180
ccctccctca agagtcgagt caccatatca gtagacacgt ccaagaacca gttctccctg   240
aagctgagct ctgtgagcgc tgcggacacg gccgtgtatt actgtgcgag agatgggtt   300
gtagcagcag ctggtccccc ttaccactac cactacggtt tggacgtctg gggccaaggg   360
accacggtca ccgtctcctc a                                             381
```

<210> SEQ ID NO 210
<211> LENGTH: 127
<212> TYPE: PRT
<213> ORGANISM: Artificial Sequence
<220> FEATURE:
<223> OTHER INFORMATION: Synthetic

<400> SEQUENCE: 210

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Phe Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Ser Ala Ala Asp Thr Ala Val Tyr Tyr Cys Ala
                85                  90                  95

Arg Asp Gly Val Val Ala Ala Gly Pro Pro Tyr His Tyr His Tyr
            100                 105                 110

Gly Leu Asp Val Trp Gly Gln Gly Thr Thr Val Thr Val Ser Ser
        115                 120                 125
```

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

```
ggtggcttca tcagtaatta ctac                                           24
```

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

```
Gly Gly Phe Ile Ser Asn Tyr Tyr
 1               5
```

<210> SEQ ID NO 213
<211> LENGTH: 21
<212> TYPE: DNA
<213> ORGANISM: Artificial Sequence
<220> FEATURE:
<223> OTHER INFORMATION: Synthetic

<400> SEQUENCE: 213
atctattata gtgggagcac c                                           21

<210> SEQ ID NO 214
<211> LENGTH: 7
<212> TYPE: PRT
<213> ORGANISM: Artificial Sequence
<220> FEATURE:
<223> OTHER INFORMATION: Synthetic

<400> SEQUENCE: 214

Ile Tyr Tyr Ser Gly Ser Thr
 1               5

<210> SEQ ID NO 215
<211> LENGTH: 63
<212> TYPE: DNA
<213> ORGANISM: Artificial Sequence
<220> FEATURE:
<223> OTHER INFORMATION: Synthetic

<400> SEQUENCE: 215
gcgagagatg gggttgtagc agcagctggt cccccttacc actaccacta cggtttggac    60
gtc                                                               63

<210> SEQ ID NO 216
<211> LENGTH: 21
<212> TYPE: PRT
<213> ORGANISM: Artificial Sequence
<220> FEATURE:
<223> OTHER INFORMATION: Synthetic

<400> SEQUENCE: 216

Ala Arg Asp Gly Val Val Ala Ala Ala Gly Pro Pro Tyr His Tyr His
 1               5                  10                  15

Tyr Gly Leu Asp Val
            20

<210> SEQ ID NO 217
<211> LENGTH: 339
<212> TYPE: DNA
<213> ORGANISM: Artificial Sequence
<220> FEATURE:
<223> OTHER INFORMATION: Synthetic

<400> SEQUENCE: 217
gacatcgtga tgacccagtc tccagactcc ctggctgtgt ctctgggcga gagggccacc    60
atcaactgca gtccagcca gaatctttta tacacctcca gcaataagaa ctccttagct   120
tggtaccagc agaaaccagg acagcctcct gagctgctca tttactgggc atctacccgg   180
gaatccgggg tccctgaccg attcagtggc agcgggtctg ggacagattt cattctcacc   240
atcagcagcc tgcaggctga agatgtggca gtttattact gtcagcaata ttatagtagt   300
ccgtggacgt tcggccaagg gaccaaggtg gaaatcaaa                         339

```
<210> SEQ ID NO 218
<211> LENGTH: 113
<212> TYPE: PRT
<213> ORGANISM: Artificial Sequence
<220> FEATURE:
<223> OTHER INFORMATION: Synthetic

<400> SEQUENCE: 218
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Leu Leu Tyr Thr
            20                  25                  30

Ser Ser Asn Lys Asn Ser Leu Ala Trp Tyr Gln Gln Lys Pro Gly Gln
        35                  40                  45

Pro Pro Glu Leu Leu Ile Tyr Trp Ala Ser Thr Arg Glu Ser Gly Val
    50                  55                  60

Pro Asp Arg Phe Ser Gly Ser Gly Ser Gly Thr Asp Phe Ile Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Trp Thr Phe Gly Gln Gly Thr Lys Val Glu Ile
            100                 105                 110

Lys

```
<210> SEQ ID NO 219
<211> LENGTH: 36
<212> TYPE: DNA
<213> ORGANISM: Artificial Sequence
<220> FEATURE:
<223> OTHER INFORMATION: Synthetic

<400> SEQUENCE: 219
```
cagaatcttt tatacacctc cagcaataag aactcc                                  36

```
<210> SEQ ID NO 220
<211> LENGTH: 12
<212> TYPE: PRT
<213> ORGANISM: Artificial Sequence
<220> FEATURE:
<223> OTHER INFORMATION: Synthetic

<400> SEQUENCE: 220
```

Gln Asn Leu Leu Tyr Thr Ser Ser Asn Lys Asn Ser
1               5                   10

```
<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221
``` tgggcatct                                                                 9

```
<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222
```

Trp Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcaatatt atagtagtcc gtggacg                                          27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Tyr Ser Ser Pro Trp Thr
1               5

<210> SEQ ID NO 225
<211> LENGTH: 372
<212> TYPE: DNA
<213> ORGANISM: Artificial Sequence
<220> FEATURE:
<223> OTHER INFORMATION: Synthetic

<400> SEQUENCE: 225
caggtgcagc tggtggagtc tgggggaggc ttggtcaagc ctggagggtc cctgagactc        60
tcctgtgcag cctctggatt caccttcagt gactactaca tgacctggat ccgccaggtt       120
ccagggaagg gactggagtg ggtttcatat atcagtagta ctgggaataa cagatattac       180
ggagactctg tgaagggccg attcgccatc tcaaggagca cgccaagaa cttactgttt        240 ctgcaaatga acagcctgaa agccgaggac acggccgttt attactgtgc aagagagaat       300
aattggaatc cttacttctt ctactatggt atggacgtct ggggccaagg gaccacggtc       360
accgtctcct ca                                                          372

<210> SEQ ID NO 226
<211> LENGTH: 124
<212> TYPE: PRT
<213> ORGANISM: Artificial Sequence
<220> FEATURE:
<223> OTHER INFORMATION: Synthetic

<400> SEQUENCE: 226

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Val Pro Gly Lys Gly Leu Glu Trp Val
        35                  40                  45

Ser Tyr Ile Ser Ser Thr Gly Asn Asn Arg Tyr Tyr Gly Asp Ser Val
    50                  55                  60

Lys Gly Arg Phe Ala Ile Ser Arg Asp Asn Ala Lys Asn Leu Leu Phe
65                  70                  75                  80

Leu Gln Met Asn Ser Leu Lys Ala Glu Asp Thr Ala Val Tyr Tyr Cys
                85                  90                  95

Ala Arg Glu Asn Asn Trp Asn Pro Tyr Phe Phe Tyr Tyr Gly Met Asp
            100                 105                 110

Val Trp Gly Gln Gly Thr Thr Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct tcagtgacta ctac                                          24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Asp Tyr Tyr
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
atcagtagta ctgggaataa caga                                          24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Ser Thr Gly Asn Asn Arg
1               5

<210> SEQ ID NO 231
<211> LENGTH: 51
<212> TYPE: DNA
<213> ORGANISM: Artificial Sequence
<220> FEATURE:
<223> OTHER INFORMATION: Synthetic

<400> SEQUENCE: 231
gcaagagaga ataattggaa tccttacttc ttctactatg gtatggacgt c             51

<210> SEQ ID NO 232
<211> LENGTH: 17
<212> TYPE: PRT
<213> ORGANISM: Artificial Sequence
<220> FEATURE:
<223> OTHER INFORMATION: Synthetic

<400> SEQUENCE: 232

Ala Arg Glu Asn Asn Trp Asn Pro Tyr Phe Phe Tyr Tyr Gly Met Asp
1               5                   10                  15

Val

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccatcttcc gtgtctgcat ctgtaggaga cagagtcacc      60
atcacttgtc gggcgagtca gggtattagc atctggttag cctggtatca gcagaaacca     120
gggaaagccc ctaaactcct gatctctgct gcgtccactt tgcaaagtgg ggtcccatca     180
aggttcagcg gcagtggatc tgggacagat ttcactctca ccatcagcag cctgcagcct    240
gaagattttg caacttacta ttgtcaacag gctaacagtt tcccgttgac gttcggccaa    300
gggaccaagg tggaaatcaa a                                              321

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ile Trp
            20                  25                  30

Leu Ala Trp Tyr Gln Gln Lys Pro Gly Lys Ala Pro Lys Leu Leu Ile
        35                  40                  45

Ser Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggtatta gcatctgg                                                   18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Ser Ile Trp
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcgtcc                                                              9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
caacaggcta acagtttccc gttgacg                                         27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Ala Asn Ser Phe Pro Leu Thr
1               5

<210> SEQ ID NO 241
<211> LENGTH: 351
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatattatg aaggaagtaa tgattactat     180
gtagactccg tgaagggccg attcaccatc tccagagaca attccaaaaa cacgctatat     240
ctgcaaatga acagcctgag agccgaggac acggctgtgt attactgtgc gagaagggac     300
tggaactcct ttgactattg gggccagggc accctggtca ccgtctcctc a              351

<210> SEQ ID NO 242
<211> LENGTH: 117

-continued

<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Tyr Tyr Glu Gly Ser Asn Asp Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Asp Trp Asn Ser Phe Asp Tyr Trp Gly Gln Gly Thr Leu
            100                 105                 110

Val Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtagcta tggc                                      24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ser Tyr Gly
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatattatg aaggaagtaa tgat                                      24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Tyr Tyr Glu Gly Ser Asn Asp

```
<210> SEQ ID NO 247
<211> LENGTH: 30
<212> TYPE: DNA
<213> ORGANISM: Artificial Sequence
<220> FEATURE:
<223> OTHER INFORMATION: Synthetic

<400> SEQUENCE: 247
gcgagaaggg actggaactc ctttgactat                                        30

<210> SEQ ID NO 248
<211> LENGTH: 10
<212> TYPE: PRT
<213> ORGANISM: Artificial Sequence
<220> FEATURE:
<223> OTHER INFORMATION: Synthetic

<400> SEQUENCE: 248

Ala Arg Arg Asp Trp Asn Ser Phe Asp Tyr
 1               5                  10

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gatattgtga tgactcagtc tccactctcc ctgtccgtca cccctggaga gccggcctcc        60
atctcctgca ggtccagtca gaacctccta aatagaaatg gattcaacta tttggattgg      120
tatttgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggttgagga tgttggggtt tattattgca tgcaagctat acaaactccg      300 tacactttg gccaggggac caagctggag atcaaa                                 336

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Leu Ser Leu Ser Val Thr Pro Gly
 1               5                  10                  15

Glu Pro Ala Ser Ile Ser Cys Arg Ser Ser Gln Asn Leu Leu Asn Arg
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Val Glu Asp Val Gly Val Tyr Tyr Cys Met Gln Ala
                85                  90                  95

Ile Gln Thr Pro Tyr Thr Phe Gly Gln Gly Thr Lys Leu Glu Ile Lys
            100                 105                 110
```

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cagaacctcc taaatagaaa tggattcaac tat                33

<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

Gln Asn Leu Leu Asn Arg Asn Gly Phe Asn Tyr
 1               5                  10

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ttgggttct                9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Leu Gly Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
atgcaagcta tacaaactcc gtacact                27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Ala Ile Gln Thr Pro Tyr Thr
 1               5

<210> SEQ ID NO 257
<211> LENGTH: 369

```
<212> TYPE: DNA
<213> ORGANISM: Artificial Sequence
<220> FEATURE:
<223> OTHER INFORMATION: Synthetic

<400> SEQUENCE: 257
gaagtgcagc tggtggagtc tgggggagac ttggtacagc ctggcaggtc cctgagactc      60
tcctgtgtag cctctggatt cacctttgat gattatgcca tgcactgggt ccggcaagct     120
ccagggaagg gcctggagtg ggtctcaggt gttagttgga gtggtagtac cgtaggctat     180
gcggactctg tgaagggccg attcaccgtc tccagagaca acgcccagaa atccctgtat     240
ctacaaatga acagtctgag agctgaggac acggccttgt attactgtgt aaaagacgcg     300
tataaataca actactacta ctacggtttg gacgtctggg gccaagggac cacggtcacc     360
gtctcctca                                                             369

<210> SEQ ID NO 258
<211> LENGTH: 123
<212> TYPE: PRT
<213> ORGANISM: Artificial Sequence
<220> FEATURE:
<223> OTHER INFORMATION: Synthetic

<400> SEQUENCE: 258
```

Glu Val Gln Leu Val Glu Ser Gly Gly Asp Leu Val Gln Pro Gly Arg
 1               5                  10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Val Ser Trp Ser Gly Ser Thr Val Gly Tyr Ala Asp Ser Val
    50                  55                  60

Lys Gly Arg Phe Thr Val Ser Arg Asp Asn Ala Gln Lys Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Ala Tyr Lys Tyr Asn Tyr Tyr Tyr Gly Leu Asp Val
            100                 105                 110

Trp Gly Gln Gly Thr Thr Val Thr Val Ser Ser
        115                 120

```
<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcacct ttgatgatta tgcc                                             24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260
```

Gly Phe Thr Phe Asp Asp Tyr Ala
 1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
gttagttgga gtggtagtac cgta                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Val Ser Trp Ser Gly Ser Thr Val
 1               5

<210> SEQ ID NO 263
<211> LENGTH: 48
<212> TYPE: DNA
<213> ORGANISM: Artificial Sequence
<220> FEATURE:
<223> OTHER INFORMATION: Synthetic

<400> SEQUENCE: 263
gtaaaagacg cgtataaata caactactac tactacggtt tggacgtc                48

<210> SEQ ID NO 264
<211> LENGTH: 16
<212> TYPE: PRT
<213> ORGANISM: Artificial Sequence
<220> FEATURE:
<223> OTHER INFORMATION: Synthetic

<400> SEQUENCE: 264

Val Lys Asp Ala Tyr Lys Tyr Asn Tyr Tyr Tyr Tyr Gly Leu Asp Val
 1               5                  10                  15

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gaaatagtga tgacgcagtc tccagccacc ctgtctgtgt ctccagggga aagagccacc     60
ctctcctgca gggccagtca gactattctc agcaacttag cctggtacct acagaaacct    120
ggccaggctc ccaggctcct catctatggt gcatccacca gggccactgg tctcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga    300
gggaccaagg tggagatcaa a                                              321

<210> SEQ ID NO 266
<211> LENGTH: 107
<212> TYPE: PRT
<213> ORGANISM: Artificial Sequence
<220> FEATURE:

<223> OTHER INFORMATION: Synthetic

<400> SEQUENCE: 266

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Ile Leu Ser Asn
            20                  25                  30

Leu Ala Trp Tyr Leu Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagactattc tcagcaac                                                 18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

```
Gln Thr Ile Leu Ser Asn
1               5
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ggtgcatcc                                                            9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

```
Gly Ala Ser
1
```

<210> SEQ ID NO 271
<211> LENGTH: 27
<212> TYPE: DNA

<213> ORGANISM: Artificial Sequence
<220> FEATURE:
<223> OTHER INFORMATION: Synthetic

<400> SEQUENCE: 271

```
cagcagtata ataactggcc tctcact                                    27
```

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

```
Gln Gln Tyr Asn Asn Trp Pro Leu Thr
 1               5
```

<210> SEQ ID NO 273
<211> LENGTH: 369
<212> TYPE: DNA
<213> ORGANISM: Artificial Sequence
<220> FEATURE:
<223> OTHER INFORMATION: Synthetic

<400> SEQUENCE: 273

```
gaagtgcagc tggtggagtc tgggggagac ttggtacagc ctggcaggtc cctgagactc    60
tcctgtgtag cctctggatt cacctttgat gattatgcca tgcactgggt ccggcaagct   120
ccagggaagg gcctggagtg gtctcaggt gttagttgga gtggtagtac cgtaggctat    180
gcggactctg tgaagggccg attcaccgtc tccagagaca acgcccagaa atccctgtat   240
ctacaaatga acagtctgag agctgaggac acggccttgt attactgtgt aaaagacgcg   300
tataaattca actactacta ctacggtttg acgtctggg gccaagggac cacggtcacc    360
gtctcctca                                                           369
```

<210> SEQ ID NO 274
<211> LENGTH: 123
<212> TYPE: PRT
<213> ORGANISM: Artificial Sequence
<220> FEATURE:
<223> OTHER INFORMATION: Synthetic

<400> SEQUENCE: 274

```
Glu Val Gln Leu Val Glu Ser Gly Gly Asp Leu Val Gln Pro Gly Arg
 1               5                  10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Val Ser Trp Ser Gly Ser Thr Val Gly Tyr Ala Asp Ser Val
    50                  55                  60

Lys Gly Arg Phe Thr Val Ser Arg Asp Asn Ala Gln Lys Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Ala Tyr Lys Phe Asn Tyr Tyr Tyr Gly Leu Asp Val
            100                 105                 110

Trp Gly Gln Gly Thr Thr Val Thr Val Ser Ser
        115                 120
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacct ttgatgatta tgcc                                          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Asp Asp Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
gttagttgga gtggtagtac cgta                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Val Ser Trp Ser Gly Ser Thr Val
1               5

<210> SEQ ID NO 279
<211> LENGTH: 48
<212> TYPE: DNA
<213> ORGANISM: Artificial Sequence
<220> FEATURE:
<223> OTHER INFORMATION: Synthetic

<400> SEQUENCE: 279
gtaaaagacg cgtataaatt caactactac tactacggtt tggacgtc                48

<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Val Lys Asp Ala Tyr Lys Phe Asn Tyr Tyr Tyr Tyr Gly Leu Asp Val
1               5                   10                  15

<210> SEQ ID NO 281
<211> LENGTH: 321
<212> TYPE: DNA

-continued

<213> ORGANISM: Artificial Sequence
<220> FEATURE:
<223> OTHER INFORMATION: Synthetic

<400> SEQUENCE: 281

```
gaaatagtga tgacgcagtc tccagccacc ctgtctgtgt ctccagggga aagagccacc      60
ctctcctgca gggccagtca gactattctc agcaacttag cctggtacct acagaaacct     120
ggccaggctc ccaggctcct catctatggt gcatccacca gggccactgg tctcccagcc     180
aggttcagtg gcagtgggtc tgggacagag ttcactctca ccatcagcag cctgcagtct     240
gaagattttg cagtttatta ctgtcagcag tataataact ggcctctcac tttcggcgga     300
gggaccaagg tggagatcaa a                                                321
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Thr Ile Leu Ser Asn
             20                  25                  30

Leu Ala Trp Tyr Leu Gln Lys Pro Gly Gln Ala Pro Arg Leu Leu Ile
         35                  40                  45

Tyr Gly Ala Ser Thr Arg Ala Thr Gly Leu Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
cagactattc tcagcaac                                                    18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Thr Ile Leu Ser Asn
  1               5
```

<210> SEQ ID NO 285
<211> LENGTH: 9
<212> TYPE: DNA
<213> ORGANISM: Artificial Sequence

```
<220> FEATURE:
<223> OTHER INFORMATION: Synthetic

<400> SEQUENCE: 285 ggtgcatcc                                                                9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Gly Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
cagcagtata ataactggcc tctcact                                            27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Asn Asn Trp Pro Leu Thr
 1               5

<210> SEQ ID NO 289
<211> LENGTH: 369
<212> TYPE: DNA
<213> ORGANISM: Artificial Sequence
<220> FEATURE:
<223> OTHER INFORMATION: Synthetic

<400> SEQUENCE: 289
caggtgcagc tggagcagtc tggggctgag gtgaagaagc ctggggcctc agtgaggatc       60
tcctgtaagg cttctggcga caccttcacc ggctactata taaactgggt gcgccaggcc      120
cctggacaag ggcttgagtg gatgggatgg atcaatacta acagtggtgg cacatacttt      180
tcacagaaat ttcaggtcag ggtcatcctg accagggaca cgtccatcaa cacagcctac      240
atggagttga gcaggctgag atctgacgac acggccgttt attactgtgc gagaatgttt      300
tacgatattt tgactaattc tgatattttt gatatttggg gccaagggac aatggtcacc      360
gtctcttca                                                              369

<210> SEQ ID NO 290
<211> LENGTH: 123
<212> TYPE: PRT
<213> ORGANISM: Artificial Sequence
<220> FEATURE:
<223> OTHER INFORMATION: Synthetic

<400> SEQUENCE: 290
```

Gln Val Gln Leu Glu Gln Ser Gly Ala Glu Val Lys Lys Pro Gly Ala
1               5                   10                  15

Ser Val Arg Ile Ser Cys Lys Ala Ser Gly Asp Thr Phe Thr Gly Tyr
            20                  25                  30

Tyr Ile Asn Trp Val Arg Gln Ala Pro Gly Gln Gly Leu Glu Trp Met
        35                  40                  45

Gly Trp Ile Asn Thr Asn Ser Gly Gly Thr Tyr Phe Ser Gln Lys Phe
    50                  55                  60

Gln Val Arg Val Ile Leu Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Met Phe Tyr Asp Ile Leu Thr Asn Ser Asp Ile Phe Asp Ile
            100                 105                 110

Trp Gly Gln Gly Thr Met Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggcgacacct tcaccggcta ctat                                          24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Asp Thr Phe Thr Gly Tyr Tyr
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atcaatacta acagtggtgg caca                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Asn Thr Asn Ser Gly Gly Thr
1               5

<210> SEQ ID NO 295
<211> LENGTH: 48
<212> TYPE: DNA
<213> ORGANISM: Artificial Sequence
<220> FEATURE:
<223> OTHER INFORMATION: Synthetic

<400> SEQUENCE: 295
gcgagaatgt tttacgatat tttgactaat tctgatattt ttgatatt        48

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Ala Arg Met Phe Tyr Asp Ile Leu Thr Asn Ser Asp Ile Phe Asp Ile
 1               5                  10                  15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctcc ctgtctgcat ctgtaggaga cagagtcacc      60
atcacttgcc gggcaagtca ggacataaga aatgatttag ctggtatca gcagaaacca     120 gggaaagccc ctaagtgcct gatctatggt gcatccagtt tgcaaagtgg ggtcccatca    180
aggttcagcg gcagtggatc tgggacagaa ttcactctca caatcagcag cctgcagcct    240
gaagattttg caacttatta ctgtctacaa cataaaaatt acatgtacac ttttggccag    300
gggaccaagt ggagatcaa a                                                321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Cys Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Asn Tyr Met Tyr
                85                  90                  95

Thr Phe Gly Gln Gly Thr Lys Leu Glu Ile Lys
            100                 105

<210> SEQ ID NO 299
<211> LENGTH: 18
<212> TYPE: DNA
<213> ORGANISM: Artificial Sequence
<220> FEATURE:

<223> OTHER INFORMATION: Synthetic

<400> SEQUENCE: 299
caggacataa gaaatgat                                                    18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Arg Asn Asp
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 ggtgcatcc                                                               9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Gly Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
ctacaacata aaaattacat gtacact                                          27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Leu Gln His Lys Asn Tyr Met Tyr Thr
 1               5

<210> SEQ ID NO 305
<211> LENGTH: 345
<212> TYPE: DNA
<213> ORGANISM: Artificial Sequence
<220> FEATURE:
<223> OTHER INFORMATION: Synthetic

<400> SEQUENCE: 305

```
caggtgcagc tacagcagtg gggcgcagga ctgttgaagc cttcggagac cctgtccctc      60
acctgcgctg tctatggtgg gtccctcagt gattactact ggagctggat ccgccagccc     120
ccagggaagg ggctggagtg gattggggaa atcaatcata gtggagacac caactacgac     180
ccgtccctca gagtcgact caccatctca gtagacacgt ccaagaacca gttctccctg      240
aagctgaact ctgtgaccgc cgcggacacg gctgtgtatt actgtgcgag cctgtatttc     300 aattttttgga tgtggggtcg aggagccctg gtcaccgtct cctca                    345
```

<210> SEQ ID NO 306
<211> LENGTH: 115
<212> TYPE: PRT
<213> ORGANISM: Artificial Sequence
<220> FEATURE:
<223> OTHER INFORMATION: Synthetic

<400> SEQUENCE: 306

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Leu Ser Asp Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Asp Thr Asn Tyr Asp Pro Ser Leu Lys
     50                  55                  60

Ser Arg Leu Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Ser Leu Tyr Phe Asn Phe Trp Met Trp Gly Arg Gly Ala Leu Val Thr
            100                 105                 110

Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggtgggtccc tcagtgatta ctac                                             24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Gly Ser Leu Ser Asp Tyr Tyr
 1               5
```

<210> SEQ ID NO 309
<211> LENGTH: 21
<212> TYPE: DNA
<213> ORGANISM: Artificial Sequence
<220> FEATURE:
<223> OTHER INFORMATION: Synthetic

<400> SEQUENCE: 309
atcaatcata gtggagacac c                                        21

<210> SEQ ID NO 310
<211> LENGTH: 7
<212> TYPE: PRT
<213> ORGANISM: Artificial Sequence
<220> FEATURE:
<223> OTHER INFORMATION: Synthetic

<400> SEQUENCE: 310

Ile Asn His Ser Gly Asp Thr
 1               5

<210> SEQ ID NO 311
<211> LENGTH: 27
<212> TYPE: DNA
<213> ORGANISM: Artificial Sequence
<220> FEATURE:
<223> OTHER INFORMATION: Synthetic

<400> SEQUENCE: 311
gcgagcctgt atttcaattt ttggatg                                  27

<210> SEQ ID NO 312
<211> LENGTH: 9
<212> TYPE: PRT
<213> ORGANISM: Artificial Sequence
<220> FEATURE:
<223> OTHER INFORMATION: Synthetic

<400> SEQUENCE: 312

Ala Ser Leu Tyr Phe Asn Phe Trp Met
 1               5

<210> SEQ ID NO 313
<211> LENGTH: 336
<212> TYPE: DNA
<213> ORGANISM: Artificial Sequence
<220> FEATURE:
<223> OTHER INFORMATION: Synthetic

<400> SEQUENCE: 313
gatattgtga tgacccagac tccactctcc tcacctgtca ttcttggaca gccggcctcc    60
atctcctgca ggtctagtca agcctcgta tacagtgatg gaaacaccta cttgagttgg   120
cttcagcaga ggccaggcca gcctccaaga ctcctaattt ataagatttc taaccggttc   180
tctggggtcc cagacagatt cagtggcagt gggacaggga cagatttcac actgaaaatc   240
agcagggtgg aagctgagga tgtcggaatt tattactgca tgcaaactac acaatttccg   300
ctcactttcg gcggagggac caaggtggag atcaaa                           336

<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Thr Pro Leu Ser Ser Pro Val Ile Leu Gly
 1               5                  10                  15

Gln Pro Ala Ser Ile Ser Cys Arg Ser Ser Gln Ser Leu Val Tyr Ser
             20                  25                  30

```
Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
 50                  55                  60

Asp Arg Phe Ser Gly Ser Gly Thr Gly Thr Asp Phe Thr Leu Lys Ile
 65                  70                  75                  80

Ser Arg Val Glu Ala Glu Asp Val Gly Ile Tyr Tyr Cys Met Gln Thr
                 85                  90                  95

Thr Gln Phe Pro Leu Thr Phe Gly Gly Gly Thr Lys Val Glu Ile Lys
            100                 105                 110
```

<210> SEQ ID NO 315
<211> LENGTH: 33
<212> TYPE: DNA
<213> ORGANISM: Artificial Sequence
<220> FEATURE:
<223> OTHER INFORMATION: Synthetic

<400> SEQUENCE: 315
caaagcctcg tatacagtga tggaaacacc tac                        33

<210> SEQ ID NO 316
<211> LENGTH: 11
<212> TYPE: PRT
<213> ORGANISM: Artificial Sequence
<220> FEATURE:
<223> OTHER INFORMATION: Synthetic

<400> SEQUENCE: 316

```
Gln Ser Leu Val Tyr Ser Asp Gly Asn Thr Tyr
 1               5                  10
```

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 aagatttct                                                    9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

```
Lys Ile Ser
 1
```

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
atgcaaacta cacaatttcc gctcact                               27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Met Gln Thr Thr Gln Phe Pro Leu Thr
1               5

<210> SEQ ID NO 321
<211> LENGTH: 369
<212> TYPE: DNA
<213> ORGANISM: Artificial Sequence
<220> FEATURE:
<223> OTHER INFORMATION: Synthetic

<400> SEQUENCE: 321
caggtgcagt tggagcaatc tggggctgag gtgaagaagc ctgggacctc agtgaggatc        60
tcctgcaagg cttctggcga catcttcacc ggctactata tgaactgggt gcgccaggcc       120
cctggacaag gcttgagtg atgggatgg atcaatacta acagtggtgg cacatacttt         180
tcacagagat ttcagggcag ggtcaccctg accaggcaca cgtccatcag aacagcctac       240
atggagttga gcaggctgag atctgacgac acggccgttt attactgtgc gagaatgttt       300
tacgatattt tgactggttc tgatgttttt gatatttggg gccaagggac aatggtcacc       360
gtctcttca                                                              369

<210> SEQ ID NO 322
<211> LENGTH: 123
<212> TYPE: PRT
<213> ORGANISM: Artificial Sequence
<220> FEATURE:
<223> OTHER INFORMATION: Synthetic

<400> SEQUENCE: 322

Gln Val Gln Leu Glu Gln Ser Gly Ala Glu Val Lys Lys Pro Gly Thr
1               5                   10                  15

Ser Val Arg Ile Ser Cys Lys Ala Ser Gly Asp Ile Phe Thr Gly Tyr
                20                  25                  30

Tyr Met Asn Trp Val Arg Gln Ala Pro Gly Gln Gly Leu Glu Trp Met
            35                  40                  45

Gly Trp Ile Asn Thr Asn Ser Gly Gly Thr Tyr Phe Ser Gln Arg Phe
        50                  55                  60

Gln Gly Arg Val Thr Leu Thr Arg Asp Thr Ser Ile Arg Thr Ala Tyr
65                  70                  75                  80

Met Glu Leu Ser Arg Leu Arg Ser Asp Asp Thr Ala Val Tyr Tyr Cys
                85                  90                  95

Ala Arg Met Phe Tyr Asp Ile Leu Thr Gly Ser Asp Val Phe Asp Ile
            100                 105                 110

Trp Gly Gln Gly Thr Met Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggcgacatct tcaccggcta ctat                                           24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Asp Ile Phe Thr Gly Tyr Tyr
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
atcaatacta acagtggtgg caca                                           24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Asn Thr Asn Ser Gly Gly Thr
1               5

<210> SEQ ID NO 327
<211> LENGTH: 48
<212> TYPE: DNA
<213> ORGANISM: Artificial Sequence
<220> FEATURE:
<223> OTHER INFORMATION: Synthetic

<400> SEQUENCE: 327
gcgagaatgt tttacgatat tttgactggt tctgatgttt ttgatatt                 48

<210> SEQ ID NO 328
<211> LENGTH: 16
<212> TYPE: PRT
<213> ORGANISM: Artificial Sequence
<220> FEATURE:
<223> OTHER INFORMATION: Synthetic

<400> SEQUENCE: 328

Ala Arg Met Phe Tyr Asp Ile Leu Thr Gly Ser Asp Val Phe Asp Ile
1               5                   10                  15

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329
gacatccaga tgacccagtc tccatcctcc ctgtctgcat ctgttggaga cagagtcacc    60
atcacttgcc gggcaagtca ggacataaga aatgatttag gctggtatca ccagaaacca   120

```
gggaaagccc ctaagtgcct gatctatggt gcatccagtt tgcaaagtgg ggtcccatct      180
aggttcagcg gcagtggatc tgggacagaa ttcactctca caatcagcag cctgcagcct      240
gaagattttg caacttatta ctgtctacaa cataaaaatt acatgtacac ttttggccag      300
gggaccaagt tggagatcaa a                                                321
```

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Asp
                 20                  25                  30

Leu Gly Trp Tyr His Gln Lys Pro Gly Lys Ala Pro Lys Cys Leu Ile
             35                  40                  45

Tyr Gly Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Lys Asn Tyr Met Tyr
                 85                  90                  95

Thr Phe Gly Gln Gly Thr Lys Leu Glu Ile Lys
            100                 105
```

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331

```
caggacataa gaaatgat                                                     18
```

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

```
Gln Asp Ile Arg Asn Asp
  1               5
```

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333

```
ggtgcatcc                                                                9
```

<210> SEQ ID NO 334

```
<211> LENGTH: 3
<212> TYPE: PRT
<213> ORGANISM: Artificial Sequence
<220> FEATURE:
<223> OTHER INFORMATION: Synthetic

<400> SEQUENCE: 334

Gly Ala Ser
 1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
ctacaacata aaaattacat gtacact                                           27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Leu Gln His Lys Asn Tyr Met Tyr Thr
 1               5

<210> SEQ ID NO 337
<211> LENGTH: 384
<212> TYPE: DNA
<213> ORGANISM: Artificial Sequence
<220> FEATURE:
<223> OTHER INFORMATION: Synthetic

<400> SEQUENCE: 337
gaggtgcagc tggtggagtc tgggggaggc ttggtacagc ctggagggtc cctgagactc        60
tcctgtgcag cctctggatt caccatcagt aattatgaaa tgaactgggt ccgtcaggct       120
ccagggaagg ggctggagtg ggtttcatac attagtacta gtggtattac catatactac       180
gcagactctg tgcagggccg attcaccatc tccagagaca tgccaagaa ctcactgtat        240 ctgcaattga acagcctgag agccgaggac acggctgttt attactgtgc gcggggatat       300
tgtacaaatg gtgtatgcta tccccattac tactactccg atatggacgt ctggggccaa       360
gggaccacgg tcaccgtctc ctca                                              384

<210> SEQ ID NO 338
<211> LENGTH: 128
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Asn Tyr
            20                  25                  30

Glu Met Asn Trp Val Arg Gln Ala Pro Gly Lys Gly Leu Glu Trp Val
        35                  40                  45
```

Ser Tyr Ile Ser Thr Ser Gly Ile Thr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Val Tyr Tyr Cys
                85                  90                  95

Ala Arg Gly Tyr Cys Thr Asn Gly Val Cys Tyr Pro His Tyr Tyr Tyr
            100                 105                 110

Ser Asp Met Asp Val Trp Gly Gln Gly Thr Thr Val Thr Val Ser Ser
        115                 120                 125

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacca tcagtaatta tgaa                                          24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Ile Ser Asn Tyr Glu
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attagtacta gtggtattac cata                                          24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Thr Ser Gly Ile Thr Ile
1               5

<210> SEQ ID NO 343
<211> LENGTH: 63
<212> TYPE: DNA
<213> ORGANISM: Artificial Sequence
<220> FEATURE:
<223> OTHER INFORMATION: Synthetic

<400> SEQUENCE: 343
gcgcggggat attgtacaaa tggtgtatgc tatccccatt actactactc cgatatggac   60
gtc                                                                 63

<210> SEQ ID NO 344
<211> LENGTH: 21
<212> TYPE: PRT
<213> ORGANISM: Artificial Sequence
<220> FEATURE:
<223> OTHER INFORMATION: Synthetic

<400> SEQUENCE: 344

```
Ala Arg Gly Tyr Cys Thr Asn Gly Val Cys Tyr Pro His Tyr Tyr Tyr
1               5                   10                  15

Ser Asp Met Asp Val
            20
```

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345

```
gacatccaga tgacccagtc tccatcctcc ctgtctgcat ctgtaggaga cagactcacc    60
atcacttgcc gggcaagtca gaccattagc acctatttaa attggtttca gcagaaagta   120
gggaatgccc ctaaactcct gatctattct acatccagtt tgcaaagtgg ggtcccagca   180
aggttcagtg gcagtggatc tgggacagat ttcactctca ccatcagcag tctgcaacct   240
gaagattttg caacttacta ctgtcaacag agttacagta gtcctccgac gttcggccaa   300
gggaccaagg tggaaatcaa a                                             321
```

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

```
Asp Ile Gln Met Thr Gln Ser Pro Ser Ser Leu Ser Ala Ser Val Gly
1               5                   10                  15

Asp Arg Leu Thr Ile Thr Cys Arg Ala Ser Gln Thr Ile Ser Thr Tyr
            20                  25                  30

Leu Asn Trp Phe Gln Gln Lys Val Gly Asn Ala Pro Lys Leu Leu Ile
        35                  40                  45

Tyr Ser Thr Ser Ser Leu Gln Ser Gly Val Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Pro
                85                  90                  95

Thr Phe Gly Gln Gly Thr Lys Val Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagaccatta gcacctat                                                   18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Thr Ile Ser Thr Tyr
 1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 tctacatcc                                                              9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Ser Thr Ser
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagagtt acagtagtcc tccgacg                                         27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Ser Tyr Ser Ser Pro Pro Thr
 1               5

<210> SEQ ID NO 353
<211> LENGTH: 560
<212> TYPE: PRT
<213> ORGANISM: Artificial Sequence
<220> FEATURE:
<223> OTHER INFORMATION: Synthetic

<400> SEQUENCE: 353

Met His Arg Pro Arg Arg Arg Gly Thr Arg Pro Pro Leu Ala Leu
 1               5                  10                  15

Leu Ala Ala Leu Leu Leu Ala Ala Arg Gly Ala Asp Ala Asn Ile Thr

```
            20                  25                  30
Glu Glu Phe Tyr Gln Ser Thr Cys Ser Ala Val Ser Lys Gly Tyr Leu
                35                  40                  45
Ser Ala Leu Arg Thr Gly Trp Tyr Thr Ser Val Ile Thr Ile Glu Leu
            50                  55                  60
Ser Asn Ile Lys Glu Asn Lys Cys Asn Gly Thr Asp Ala Lys Val Lys
65                  70                  75                  80
Leu Ile Asn Gln Glu Leu Asp Lys Tyr Lys Asn Ala Val Thr Glu Leu
                85                  90                  95
Gln Leu Leu Met Gln Ser Thr Thr Ala Ala Asn Asn Arg Ala Arg Arg
                100                 105                 110
Glu Leu Pro Arg Phe Met Asn Tyr Thr Leu Asn Asn Thr Lys Lys Thr
                115                 120                 125
Asn Val Thr Leu Ser Lys Lys Arg Lys Arg Arg Phe Leu Gly Phe Leu
                130                 135                 140
Leu Gly Val Gly Ser Ala Ile Ala Ser Gly Ile Ala Val Ser Lys Val
145                 150                 155                 160
Leu His Leu Glu Gly Glu Val Asn Lys Ile Lys Ser Ala Leu Leu Ser
                165                 170                 175
Thr Asn Lys Ala Val Val Ser Leu Ser Asn Gly Val Ser Val Leu Thr
                180                 185                 190
Ser Lys Val Leu Asp Leu Lys Asn Tyr Ile Asp Lys Gln Leu Leu Pro
                195                 200                 205
Ile Val Asn Lys Gln Ser Cys Arg Ile Ser Asn Ile Glu Thr Val Ile
                210                 215                 220
Glu Phe Gln Gln Lys Asn Asn Arg Leu Leu Glu Ile Thr Arg Glu Phe
225                 230                 235                 240
Ser Val Asn Ala Gly Val Thr Thr Pro Val Ser Thr Tyr Met Leu Thr
                245                 250                 255
Asn Ser Glu Leu Leu Ser Leu Ile Asn Asp Met Pro Ile Thr Asn Asp
                260                 265                 270
Gln Lys Lys Leu Met Ser Asn Asn Val Gln Ile Val Arg Gln Gln Ser
                275                 280                 285
Tyr Ser Ile Met Ser Ile Ile Lys Glu Glu Val Leu Ala Tyr Val Val
                290                 295                 300
Gln Leu Pro Leu Tyr Gly Val Ile Asp Thr Pro Cys Trp Lys Leu His
305                 310                 315                 320
Thr Ser Pro Leu Cys Thr Thr Asn Thr Lys Glu Gly Ser Asn Ile Cys
                325                 330                 335
Leu Thr Arg Thr Asp Arg Gly Trp Tyr Cys Asp Asn Ala Gly Ser Val
                340                 345                 350
Ser Phe Phe Pro Gln Ala Glu Thr Cys Lys Val Gln Ser Asn Arg Val
                355                 360                 365
Phe Cys Asp Thr Met Asn Ser Leu Thr Leu Pro Ser Glu Val Asn Leu
                370                 375                 380
Cys Asn Val Asp Ile Phe Asn Pro Lys Tyr Asp Cys Lys Ile Met Thr
385                 390                 395                 400
Ser Lys Thr Asp Val Ser Ser Ser Val Ile Thr Ser Leu Gly Ala Ile
                405                 410                 415
Val Ser Cys Tyr Gly Lys Thr Lys Cys Thr Ala Ser Asn Lys Asn Arg
                420                 425                 430
Gly Ile Ile Lys Thr Phe Ser Asn Gly Cys Asp Tyr Val Ser Asn Lys
                435                 440                 445
```

Gly Val Asp Thr Val Ser Val Gly Asn Thr Leu Tyr Tyr Val Asn Lys
                450                 455                 460

Gln Glu Gly Lys Ser Leu Tyr Val Lys Gly Glu Pro Ile Ile Asn Phe
465                 470                 475                 480

Tyr Asp Pro Leu Val Phe Pro Ser Asp Glu Phe Asp Ala Ser Ile Ser
                485                 490                 495

Gln Val Asn Glu Lys Ile Asn Gln Ser Leu Ala Phe Ile Arg Lys Ser
                500                 505                 510

Asp Glu Leu Leu His His Val Asn Ala Gly Lys Ser Thr Thr Asn Ile
                515                 520                 525

Met Ile Thr Thr Glu Gln Lys Leu Ile Ser Glu Glu Asp Leu Gly Gly
                530                 535                 540

Glu Gln Lys Leu Ile Ser Glu Glu Asp Leu His His His His His His
545                 550                 555                 560

<210> SEQ ID NO 354
<211> LENGTH: 574
<212> TYPE: PRT
<213> ORGANISM: Artificial Sequence
<220> FEATURE:
<223> OTHER INFORMATION: Synthetic

<400> SEQUENCE: 354

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Asn
65                  70                  75                  80

Gln Glu Leu Asp Lys Tyr Lys Asn Ala Val Thr Glu Leu Gln Leu Leu
                85                  90                  95

Met Gln Ser Thr Thr Ala Ala Asn Asn Arg Ala Arg Arg Glu Leu Pro
                100                 105                 110

Arg Phe Met Asn Tyr Thr Leu Asn Asn Thr Lys Lys Thr Asn Val Thr
                115                 120                 125

Leu Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Arg Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His His Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 355
<211> LENGTH: 11
<212> TYPE: PRT
<213> ORGANISM: Artificial Sequence
<220> FEATURE:
<223> OTHER INFORMATION: Synthetic

<400> SEQUENCE: 355

Glu Gly Glu Val Asn Lys Ile Lys Ser Ala Leu
 1               5                  10

<210> SEQ ID NO 356
<211> LENGTH: 17
<212> TYPE: PRT
<213> ORGANISM: Artificial Sequence
```

```
<220> FEATURE:
<223> OTHER INFORMATION: Synthetic

<400> SEQUENCE: 356

Leu Ser Thr Asn Lys Ala Val Val Ser Leu Ser Asn Gly Val Ser Val
 1               5                  10                  15

Leu

<210> SEQ ID NO 357
<211> LENGTH: 454
<212> TYPE: PRT
<213> ORGANISM: Artificial Sequence
<220> FEATURE:
<223> OTHER INFORMATION: Synthetic
      AM22 HC

<400> SEQUENCE: 357

Gln Val Gln Leu Val Gln Ser Gly Ala Glu Val Lys Lys Pro Gly Ala
 1               5                  10                  15

Thr Val Lys Val Ser Cys Lys Ile Ser Gly His Thr Leu Ile Lys Leu
             20                  25                  30

Ser Ile His Trp Val Arg Gln Ala Pro Gly Lys Gly Leu Glu Trp Met
         35                  40                  45

Gly Gly Tyr Glu Gly Glu Val Asp Glu Ile Phe Tyr Ala Gln Lys Phe
     50                  55                  60

Gln His Arg Leu Thr Val Ile Ala Asp Thr Ala Thr Asp Thr Val Tyr
 65                  70                  75                  80

Met Glu Leu Gly Arg Leu Thr Ser Asp Asp Thr Ala Val Tyr Phe Cys
                 85                  90                  95

Gly Thr Leu Gly Val Thr Val Thr Glu Ala Gly Leu Gly Ile Asp Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
```

```
305                 310                 315                 320
Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 358
<211> LENGTH: 215
<212> TYPE: PRT
<213> ORGANISM: Artificial Sequence
<220> FEATURE:
<223> OTHER INFORMATION: Synthetic
      AM22 LC

<400> SEQUENCE: 358

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ile Val Ser Arg Asn
            20                  25                  30

His Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Val Arg Phe Ser
    50                  55                  60

Gly Ser Gly Ser Gly Thr Asp Phe Thr Leu Thr Ile Asn Gly Leu Ala
65                  70                  75                  80

Pro Glu Asp Phe Ala Val Tyr Tyr Cys Leu Ser Ser Asp Ser Ser Ile
                85                  90                  95

Phe Thr Phe Gly Pro Gly Thr Lys Val Asp Phe Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 359
<211> LENGTH: 450
<212> TYPE: PRT
<213> ORGANISM: Artificial Sequence
<220> FEATURE:
<223> OTHER INFORMATION: Synthetic
      Motavizumab HC

<400> SEQUENCE: 359

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 360
<211> LENGTH: 213
<212> TYPE: PRT
<213> ORGANISM: Artificial Sequence
<220> FEATURE:
<223> OTHER INFORMATION: Synthetic
      Motavizumab LC

<400> SEQUENCE: 360

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 361
<211> LENGTH: 450
<212> TYPE: PRT

<213> ORGANISM: Artificial Sequence
<220> FEATURE:
<223> OTHER INFORMATION: Synthetic Palivizumab HC

<400> SEQUENCE: 361

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Ala
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 362
<211> LENGTH: 213
<212> TYPE: PRT
<213> ORGANISM: Artificial Sequence
<220> FEATURE:
<223> OTHER INFORMATION: Synthetic
      Palivizumab LC

<400> SEQUENCE: 362

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65              70                  75                  80

Asp Phe Ala Thr Tyr Tyr Cys Phe Gln Gly Ser Gly Tyr Pro Phe Thr
            85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 363
<211> LENGTH: 453
<212> TYPE: PRT
<213> ORGANISM: Artificial Sequence
<220> FEATURE:
<223> OTHER INFORMATION: Synthetic

<400> SEQUENCE: 363

Glu Val Gln Leu Val Glu Ser Gly Gly Asp Leu Val Gln Pro Gly Arg
```

-continued

```
  1               5                  10                 15
Ser Leu Arg Leu Ser Cys Val Ala Ser Gly Phe Thr Phe Asp Asp Tyr
             20                  25                 30
Ala Met His Trp Val Arg Gln Ala Pro Gly Lys Gly Leu Glu Trp Val
             35                  40                 45
Ser Gly Val Ser Trp Ser Gly Ser Thr Val Gly Tyr Ala Asp Ser Val
             50                  55                 60
Lys Gly Arg Phe Thr Val Ser Arg Asp Asn Ala Gln Lys Ser Leu Tyr
 65                  70                  75                 80
Leu Gln Met Asn Ser Leu Arg Ala Glu Asp Thr Ala Leu Tyr Tyr Cys
             85                  90                 95
Val Lys Asp Ala Tyr Lys Phe Asn Tyr Tyr Tyr Gly Leu Asp Val
             100                 105                110
Trp Gly Gln Gly Thr Thr Val Thr Val Ser Ser Ala Ser Thr Lys Gly
             115                 120                125
Pro Ser Val Phe Pro Leu Ala Pro Ser Ser Lys Ser Thr Ser Gly Gly
             130                 135                140
Thr Ala Ala Leu Gly Cys Leu Val Lys Asp Tyr Phe Pro Glu Pro Val
145                  150                 155                160
Thr Val Ser Trp Asn Ser Gly Ala Leu Thr Ser Gly Val His Thr Phe
             165                 170                175
Pro Ala Val Leu Gln Ser Ser Gly Leu Tyr Ser Leu Ser Ser Val Val
             180                 185                190
Thr Val Pro Ser Ser Ser Leu Gly Thr Gln Thr Tyr Ile Cys Asn Val
             195                 200                205
Asn His Lys Pro Ser Asn Thr Lys Val Asp Lys Lys Val Glu Pro Lys
210                  215                 220
Ser Cys Asp Lys Thr His Thr Cys Pro Pro Cys Pro Ala Pro Glu Leu
225                  230                 235                240
Leu Gly Gly Pro Ser Val Phe Leu Phe Pro Pro Lys Pro Lys Asp Thr
             245                 250                255
Leu Met Ile Ser Arg Thr Pro Glu Val Thr Cys Val Val Val Asp Val
             260                 265                270
Ser His Glu Asp Pro Glu Val Lys Phe Asn Trp Tyr Val Asp Gly Val
             275                 280                285
Glu Val His Asn Ala Lys Thr Lys Pro Arg Glu Glu Gln Tyr Asn Ser
             290                 295                300
Thr Tyr Arg Val Val Ser Val Leu Thr Val Leu His Gln Asp Trp Leu
305                  310                 315                320
Asn Gly Lys Glu Tyr Lys Cys Lys Val Ser Asn Lys Ala Leu Pro Ala
             325                 330                335
Pro Ile Glu Lys Thr Ile Ser Lys Ala Lys Gly Gln Pro Arg Glu Pro
             340                 345                350
Gln Val Tyr Thr Leu Pro Pro Ser Arg Asp Glu Leu Thr Lys Asn Gln
             355                 360                365
Val Ser Leu Thr Cys Leu Val Lys Gly Phe Tyr Pro Ser Asp Ile Ala
             370                 375                380
Val Glu Trp Glu Ser Asn Gly Gln Pro Glu Asn Asn Tyr Lys Thr Thr
385                  390                 395                400
Pro Pro Val Leu Asp Ser Asp Gly Ser Phe Phe Leu Tyr Ser Lys Leu
             405                 410                415
Thr Val Asp Lys Ser Arg Trp Gln Gln Gly Asn Val Phe Ser Cys Ser
             420                 425                430
```

```
Val Met His Glu Ala Leu His Asn His Tyr Thr Gln Lys Ser Leu Ser
        435                 440             445

Leu Ser Pro Gly Lys
    450

<210> SEQ ID NO 364
<211> LENGTH: 214
<212> TYPE: PRT
<213> ORGANISM: Artificial Sequence
<220> FEATURE:
<223> OTHER INFORMATION: Synthetic

<400> SEQUENCE: 364

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Thr Ile Leu Ser Asn
             20                  25                  30

Leu Ala Trp Tyr Leu Gln Lys Pro Gly Gln Ala Pro Arg Leu Leu Ile
         35                  40                  45

Tyr Gly Ala Ser Thr Arg Ala Thr Gly Leu Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210
```

HUMAN ANTIBODIES TO RESPIRATORY SYNCYTIAL VIRUS F PROTEIN AND METHODS OF USE THEREOF

CROSS-REFERENCE TO RELATED APPLICATIONS

This application is a continuation of U.S. application Ser. No. 14/207,797, filed Mar. 13, 2014, which claims the benefit under 35 USC § 119(e) of U.S. Provisional Application Nos. 61/782,215, filed Mar. 14, 2013 and 61/911,093, filed Dec. 3, 2013, each of which is herein specifically incorporated by reference in its entirety.

SEQUENCE LISTING

This application incorporates by reference the Sequence Listing submitted in Computer Readable Form as file 480467-Sequence.txt, created on Aug. 5, 2016 and containing 149,291 bytes.

FIELD OF THE INVENTION

The present invention is related to human antibodies and antigen-binding fragments of human antibodies that specifically bind to Respiratory Syncytial Virus F protein (RSV-F), compositions comprising these antibodies and methods of using these antibodies.

STATEMENT OF RELATED ART

Respiratory syncytial virus (RSV) is a negative sense, single stranded RNA virus that is the leading cause of serious respiratory tract infections in infants and children, with the primary infection occurring in children from 6 weeks to 2 years of age and uncommonly in the first 4 weeks of life during nosocomial epidemics (Hall et al., 1979, New Engl. J. Med. 300:393-396). (Feigen et al., eds., 1987, In: Textbook of Pediatric Infectious Diseases, W B Saunders, Philadelphia at pages 1653-1675; New Vaccine Development, Establishing Priorities, Vol. 1, 1985, National Academy Press, Washington D.C. at pages 397-409; Ruuskanen et al., 1993, Curr. Probl. Pediatr. 23:50-79; Hall et al., 1979, New Engl. J. Med. 300:393-396). Certain populations of children are at risk for developing an RSV infection and these include preterm infants (Hall et al., 1979, New Engl. J. Med. 300:393-396), children with congenital malformations of the airway, children with bronchopulmonary dysplasia (Groothuis et al., 1988, Pediatrics 82:199-203), children with congenital heart disease (MacDonald et al., New Engl. J. Med. 307:397-400), and children with congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830).

RSV can infect the adult population as well. In this population, RSV causes primarily an upper respiratory tract disease, although elderly patients may be at greater risk for a serious infection and pneumonia (Evans, A. S., eds., 1989, Viral Infections of Humans. Epidemiology and Control, $3^{rd}$ ed., Plenum Medical Book, New York at pages 525-544), as well as adults who are immunosuppressed, particularly bone marrow transplant patients (Hertz et al., 1989, Medicine 68:269-281). Other at risk patients include those suffering from congestive heart failure and those suffering from chronic obstructive pulmonary disease (ie. COPD). There have also been reports of epidemics among nursing home patients and institutionalized young adults (Falsey, A. R., 1991, Infect. Control Hosp. Epidemiol. 12:602-608; and Garvie et al., 1980, Br. Med. J. 281:1253-1254).

While treatment options for established RSV disease are limited, more severe forms of the disease of the lower respiratory tract often require considerable supportive care, including administration of humidified oxygen and respiratory assistance (Fields et al., eds, 1990, Fields Virology, $2^{nd}$ ed., Vol. 1, Raven Press, New York at pages 1045-1072).

Ribavirin, which is the only drug approved for treatment of infection, has been shown to be effective in the treatment of pneumonia and bronchiolitis associated with RSV infection, and has been shown to modify the course of severe RSV disease in immunocompetent children (Smith et al., 1991, New Engl. J. Med. 325:24-29). The use of ribavirin is limited due to concerns surrounding its potential risk to pregnant women who may be exposed to the aerosolized drug while it is being administered in a hospital environment.

Similarly, while a vaccine may be useful, no commercially available vaccine has been developed to date. Several vaccine candidates have been abandoned and others are under development (Murphy et al., 1994, Virus Res. 32:13-36). The development of a vaccine has proven to be problematic. In particular, immunization would be required in the immediate neonatal period since the peak incidence of lower respiratory tract disease occurs at 2-5 months of age. However, it is known that the neonatal immune response is immature at that time. Plus, the infant at that point in time still has high titers of maternally acquired RSV antibody, which might reduce vaccine immunogenicity (Murphy et al., 1988, J. Virol. 62:3907-3910; and Murphy et al., 1991, Vaccine 9:185-189).

Two glycoproteins, F and G, on the surface of RSV have been shown to be targets of neutralizing antibodies (Fields et al., 1990, supra; and Murphy et al., 1994, supra). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation and cell to cell virus spread.

Currently, the only approved approach to prophylaxis of RSV disease is passive immunization. For example, the humanized antibody, palivizumab (SYNAGIS®), which is specific for an epitope on the F protein, is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et aL, (1997), J. Infect. Diseases 176:1215-1224 and U.S. Pat. No. 5,824,307, the entire contents of which are incorporated herein by reference.

Although SYNAGIS® has been successfully used for the prevention of RSV infection in pediatric patients, multiple intramuscular doses of 15 mg/kg of SYNAGIS® are required to achieve a prophylactic effect. The necessity for the administration of multiple intramuscular doses of antibody requires repeated visits to the doctor's office, which is not only inconvenient for the patient but can also result in missed doses.

Efforts were made to improve on the therapeutic profile of an anti-RSV-F antibody, and this lead to the identification and development of motavizumab, also referred to as NUMAX™. However, clinical testing revealed that certain of the patients being administered motavizumab were having severe hypersensitivity reactions. Further development of this humanized anti-RSV-F antibody was then discontinued.

Other antibodies to RSV-F protein have been described and can be found in U.S. Pat. Nos. 6,656,467; 5,824,307, 7,786,273; 7,670,600; 7,083,784; 6,818,216: 7,700,735; 7,553,489; 7,323,172; 7,229,619; 7,425,618; 7,740,851; 7,658,921; 7,704,505; 7,635,568; 6,855,493; 6,565,849; 7,582,297; 7,208,162; 7,700,720; 6,413,771; 5,811,524; 6,537,809; 5,762,905; 7,070,786; 7,364,742; 7,879,329; 7,488,477; 7,867,497; 534 411; 6,835,372; 7,482,024; 7,691,603; 8,562,996; 8,568,726; US20100015596; WO2009088159A1. To date, none other than SYNAGIS® has been approved by a regulatory agency for use in preventing an RSV infection.

Thus, a need still exists for antibodies that specifically bind to an RSV antigen, such as RSV-F, which are highly potent and which produce no adverse effects that would preclude approval for clinical use.

BRIEF SUMMARY OF THE INVENTION

The invention provides isolated fully human monoclonal antibodies (mAbs) and antigen-binding fragments thereof that bind specifically to Respiratory Syncytial Virus F protein (RSV-F). Given the role that the F protein plays in fusion of the virus with the cell and in cell to cell transmission of the virus, the antibodies described herein provide a method of inhibiting that process and as such, may be used for preventing infection of a patient exposed to, or at risk for acquiring an infection with RSV, or for treating and/or ameliorating one or more symptoms associated with RSV infection in a patient exposed to, or at risk for acquiring an infection with RSV, or suffering from infection with RSV. The antibodies described herein may also be used to prevent or to treat an RSV infection in a patient who may experience a more severe form of the RSV infection due to an underlying or pre-existing medical condition. A patient who may benefit from treatment with an antibody of the invention may be a pre-term infant, a full-term infant born during RSV season (approximately late fall (November) through early spring (April)) that is at risk because of other pre-existing or underlying medical conditions including congenital heart disease or chronic lung disease, a child greater than one year of age with or without an underlying medical condition, an institutionalized or hospitalized patient, or an elderly adult (>65 years of age) with or without an underlying medical condition, such as congestive heart failure (CHF), or chronic obstructive pulmonary disease (COPD). A patient who may benefit from such therapy may suffer from a medical condition resulting from a compromised pulmonary, cardiovascular, neuromuscular, or immune system. For example, the patient may suffer from an abnormality of the airway, or an airway malfunction, a chronic lung disease, a chronic or congenital heart disease, a neuromuscular disease that compromises the handling of respiratory secretions, or the patient may be immunosuppressed due to severe combined immunodeficiency disease or severe acquired immunodeficiency disease, or from any other underlying infectious disease or cancerous condition that results in immunosuppression, or the patient may be immunosuppressed due to treatment with an immunosuppressive drug (e.g. any drug used for treating a transplant patient) or radiation therapy. A patient who may benefit from the antibodies of the invention may be a patient that suffers from chronic obstructive pulmonary disease (COPD), cystic fibrosis (CF), bronchopulmonary dysplasia, congestive heart failure (CHF), or congenital heart disease.

Because the antibodies of the invention are more effective at neutralization of RSV compared to known antibodies, lower doses of the antibodies or antibody fragments could be used to achieve a greater level of protection against infection with RSV, and more effective treatment and/or amelioration of symptoms associated with an RSV infection. Accordingly, the use of lower doses of antibodies or fragments thereof which immunospecifically bind to RSV-F antigen may result in fewer or less severe adverse events. Likewise, the use of more effective neutralizing antibodies may result in a diminished need for frequent administration of the antibodies or antibody fragments than previously envisioned as necessary for the prevention of infection, or for virus neutralization, or for treatment or amelioration of one or more symptoms associated with an RSV infection. Symptoms of RSV infection may include a bluish skin color due to lack of oxygen (hypoxia), breathing difficulty (rapid breathing or shortness of breath), cough, croupy cough ("seal bark" cough), fever, nasal flaring, nasal congestion (stuffy nose), apnea, decreased appetite, dehydration, poor feeding, altered mental status, or wheezing.

Such antibodies may be useful when administered prophylactically (prior to exposure to the virus and infection with the virus) to lessen the severity, or duration of a primary infection with RSV, or ameliorate at least one symptom associated with the infection. The antibodies may be used alone or in conjunction with a second agent useful for treating an RSV infection. In certain embodiments, the antibodies may be given therapeutically (after exposure to and infection with the virus) either alone, or in conjunction with a second agent to lessen the severity or duration of the primary infection, or to ameliorate at least one symptom associated with the infection. In certain embodiments, the antibodies may be used prophylactically as stand-alone therapy to protect patients who are at risk for acquiring an infection with RSV, such as those described above. Any of these patient populations may benefit from treatment with the antibodies of the invention, when given alone or in conjunction with a second agent, including for example, an anti-viral therapy, such as ribavirin, or other anti-viral vaccines.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. lmmunol. 164:1925-1933).

Accordingly, in a first aspect, the invention provides an isolated antibody or an antigen-binding fragment thereof that specifically binds to Respiratory Syncytial Virus F protein (RSV-F).

In one embodiment, the invention provides an isolated antibody or an antigen-binding fragment thereof that specifically binds to Respiratory Syncytial Virus F protein (RSV-F), wherein the antibody has one or more of the following characteristics:
   (a) is a fully human monoclonal antibody;
   (b) interacts with an amino acid sequence comprising amino acid residues ranging from about position 161 to about position 188 of SEQ ID NO: 354;
   (c) interacts with either the serine at position 173 of SEQ ID NO: 354, or the threonine at position 174 of SEQ ID NO: 354, or both the serine at position 173 of SEQ ID NO: 354 and the threonine at position 174 of SEQ ID NO: 354;

(d) is capable of neutralizing respiratory syncytial virus subtype A and subtype B strains in vitro;

(e) demonstrates the ability to significantly reduce the nasal and/or lung viral load in vivo in an animal model of RSV infection; or (f) inhibits fusion of the virus to the cell.

In one embodiment, the invention provides an isolated antibody or an antigen-binding fragment thereof that specifically binds to Respiratory Syncytial Virus F protein (RSV-F), wherein the antibody interacts with an amino acid sequence comprising amino acid residues ranging from about position 161 to about position 188 of SEQ ID NO: 354.

In one embodiment, the antibody is a fully human monoclonal antibody or an antigen-binding fragment thereof that specifically binds to Respiratory Syncytial Virus F protein (RSV-F), wherein the antibody or an antigen-binding fragment thereof interacts with an amino acid sequence comprising amino acid residues ranging from about position 161 to about position 188 of SEQ ID NO: 354, and wherein the antibody neutralizes respiratory syncytial virus subtype A and/or subtype B strains in vitro and in vivo.

In one embodiment, the invention provides an isolated antibody or an antigen-binding fragment thereof that specifically binds to Respiratory Syncytial Virus F protein (RSV-F), wherein the antibody or the antigen-binding fragment thereof demonstrates the ability to significantly reduce the lung viral load in a mouse model of RSV infection when administered at a dose ranging from about 0.05 mg/kg to about 0.15 mg/kg.

In one embodiment, the invention provides an isolated antibody or an antigen-binding fragment thereof that specifically binds to Respiratory Syncytial Virus F protein (RSV-F), wherein the antibody or the antigen-binding fragment thereof demonstrates a 1-2 logs greater reduction of nasal and/or lung viral titers as compared to palivizumab in a cotton rat model of RSV infection when administered at a dose ranging from about 0.62 mg/kg to about 5.0 mg/kg.

In one embodiment, the invention provides an isolated antibody or an antigen-binding fragment thereof that specifically binds to Respiratory Syncytial Virus F protein (RSV-F), wherein the antibody or the antigen-binding fragment thereof demonstrates an $ED_{99}$ of about 0.15 mg/kg or less when administered in a mouse model of RSV subtype A infection.

In one embodiment, the invention provides an isolated antibody or an antigen-binding fragment thereof that specifically binds to Respiratory Syncytial Virus F protein (RSV-F), wherein the antibody or the antigen-binding fragment thereof demonstrates an $ED_{99}$ of about 0.62 mg/kg or less when administered in a cotton rat model of RSV subtype A infection.

In one embodiment, the invention provides an isolated antibody or an antigen-binding fragment thereof that specifically binds to Respiratory Syncytial Virus F protein (RSV-F), wherein the antibody or the antigen-binding fragment thereof demonstrates an $ED_{99}$ of about 2.5 mg/kg or less when administered in a cotton rat model of RSV subtype B infection.

In one embodiment, the isolated antibody or an antigen-binding fragment thereof that specifically binds to Respiratory Syncytial Virus F protein (RSV-F), demonstrates an $ED_{99}$ that is about 2 to 3 fold lower than the $ED_{99}$ for palivizumab or motavizumab.

In one embodiment, the isolated antibody or an antigen-binding fragment thereof that specifically binds to Respiratory Syncytial Virus F protein (RSV-F), demonstrates a half maximal inhibitory concentration ($IC_{50}$) of about 2 pM to about 600 pM in a microneutralization assay specific for RSV subtype A strains of RSV.

In one embodiment, the isolated antibody or an antigen-binding fragment thereof that specifically binds to Respiratory Syncytial Virus F protein (RSV-F), demonstrates a half maximal inhibitory concentration ($IC_{50}$) of about 6 pM to about 100 pM in a microneutralization assay specific for RSV subtype B strains of RSV.

In one embodiment, the isolated antibody or an antigen-binding fragment thereof that specifically binds to RSV-F protein demonstrates a neutralization potency against one or more subtype A laboratory strains of RSV that is about a 15 to 17 fold improvement over palivizumab, or demonstrates a neutralization potency against one or more subtype A clinical strains of RSV that is about 10 to 22 fold improvement over palivizumab.

In one embodiment, the isolated antibody or an antigen-binding fragment thereof that specifically binds to Respiratory Syncytial Virus F protein (RSV-F), demonstrates a neutralization potency against one or more subtype B laboratory strains of RSV that is about a 2 to 5 fold improvement over palivizumab.

In one embodiment, the isolated antibody or an antigen-binding fragment thereof that specifically binds to Respiratory Syncytial Virus F protein (RSV-F), demonstrates a neutralization potency against one or more subtype A laboratory strains or subtype A clinical strains of RSV that is about a 0.5 to 2 fold improvement over AM-22.

In one embodiment, the isolated antibody or an antigen-binding fragment thereof that specifically binds to Respiratory Syncytial Virus F protein (RSV-F), demonstrates a neutralization potency against one or more subtype B laboratory strains of RSV that is about a 2.5 to 17 fold improvement over AM-22.

In one embodiment, the isolated human antibody or an antigen-binding fragment thereof that specifically binds to Respiratory Syncytial Virus F protein (RSV-F), exhibits a $K_D$ ranging from $1 \times 10^{-7}$ M to $6 \times 10^{-10}$ M, as measured by surface plasmon resonance.

In one embodiment, the isolated human antibody or an antigen-binding fragment thereof that specifically binds to Respiratory Syncytial Virus F protein (RSV-F), exhibits a $K_D$ ranging from $1 \times 10^{-7}$ M to $9 \times 10^{-9}$ M, as measured by surface plasmon resonance.

In one embodiment, the isolated human antibody or antigen-binding fragment thereof that specifically binds to Respiratory Syncytial Virus F protein (RSV-F), comprises the three heavy chain CDRs (HCDR1, HCDR2 and HCDR3) contained within a HCVR amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338; and the three light chain CDRs (LCDR1, LCDR2 and LCDR3) contained within a LCVR amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), J. Mol. Biol. 273:927-948; and Martin et al., (1989), Proc. Natl. Acad. Sci. USA 86:9268-9272. Public databases are also available for identifying CDR sequences within an antibody.

In one embodiment, the isolated human antibody or antigen-binding fragment thereof that specifically binds to Respiratory Syncytial Virus F protein (RSV-F), comprises a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338.

In one embodiment, the isolated human antibody or antigen-binding fragment thereof that specifically binds to Respiratory Syncytial Virus F protein (RSV-F), comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346.

In one embodiment, the isolated human antibody or antigen-binding fragment thereof that specifically binds to Respiratory Syncytial Virus F protein (RSV-F), comprises a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338; and a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346.

In one embodiment, the isolated human antibody or antigen-binding fragment thereof that specifically binds to Respiratory Syncytial Virus F protein (RSV-F), comprises the heavy chain amino acid sequence of SEQ ID NO: 363 and the light chain amino acid sequence of SEQ ID NO: 364.

In one embodiment, the isolated human antibody or antigen-binding fragment thereof that specifically binds to Respiratory Syncytial Virus F protein (RSV-F), comprises a HCVR/LCVR amino acid sequence pair selected from the group consisting of SEQ ID NOs: SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In one embodiment, the isolated human antibody or antigen-binding fragment thereof that specifically binds to Respiratory Syncytial Virus F protein (RSV-F), comprises a HCVR/LCVR amino acid sequence pair selected from the group consisting of SEQ ID NOs: 274/282 and 338/346.

In one embodiment, the isolated human antibody or antigen-binding fragment thereof that specifically binds to Respiratory Syncytial Virus F protein (RSV-F), comprises:
  (a) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, and 344; and
  (b) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336 and 352.

In one embodiment, the isolated human antibody or antigen-binding fragment thereof that specifically binds to Respiratory Syncytial Virus F protein (RSV-F), further comprises:
  (c) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340;
  (d) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342;
  (e) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348; and
  (f) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350.

In one embodiment, the isolated human antibody or antigen-binding fragment thereof that specifically binds to Respiratory Syncytial Virus F protein (RSV-F) comprises:
  (a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340;
  (b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342;
  (c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, and 344;
  (4d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348;
  (e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350; and
  (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336 and 352.

In one embodiment, the isolated human antibody or antigen-binding fragment thereof that specifically binds to Respiratory Syncytial Virus F protein (RSV-F) comprises:
  (a) a HCDR1 domain having an amino acid sequence selected from the group consisting of SEQ ID NOs: 276 and 340;
  (b) a HCDR2 domain having an amino acid sequence selected from the group consisting of SEQ ID NOs: 278 and 342;
  (c) a HCDR3 domain having an amino acid sequence selected from the group consisting of SEQ ID NOs: 280 and 344;
  (d) a LCDR1 domain having an amino acid sequence selected from the group consisting of SEQ ID NOs: 284 and 348;
  (e) a LCDR2 domain having an amino acid sequence selected from the group consisting of SEQ ID NOs: 286 and 350; and (f) a LCDR3 domain having an amino acid sequence selected from the group consisting of SEQ ID NOs: 288 and 352.

In one embodiment, the isolated human antibody or antigen binding fragment thereof that specifically binds to RSV-F comprises the HCDR1, HCDR2 and HCDR3 amino acid sequences of SEQ ID NOs: 276, 278 and 280, respectively and LCDR1, LCDR2 and LCDR3 amino acid sequences of SEQ ID NOs: 284, 286 and 288, respectively.

In one embodiment, the isolated human antibody or antigen binding fragment thereof that specifically binds to RSV-F comprises the HCDR1, HCDR2 and HCDR3 amino acid sequences of SEQ ID NOs: 340, 342 and 344, respectively and LCDR1, LCDR2 and LCDR3 amino acid sequences of SEQ ID NOs: 348, 350 and 352, respectively.

In one embodiment, the isolated human antibody or antigen-binding fragment thereof that specifically binds to Respiratory Syncytial Virus F protein (RSV-F) competes for specific binding to RSV-F with an antibody or antigen-binding fragment comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In one embodiment, the isolated human antibody or antigen-binding fragment thereof, which comprises heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346, and which specifically binds to Respiratory Syncytial Virus F protein (RSV-F), does not compete for specific binding to RSV-F with palivizumab, motavizumab, or AM-22.

In one embodiment, the isolated human antibody or antigen-binding fragment thereof that specifically binds to Respiratory Syncytial Virus F protein (RSV-F) binds the same epitope on RSV-F that is recognized by an antibody comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In one embodiment, the isolated human antibody or antigen-binding fragment thereof, which comprises heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346, and which specifically binds to Respiratory Syncytial Virus F protein (RSV-F), does not bind the same epitope on RSV-F as palivizumab or motavizumab.

In one embodiment, the invention provides a fully human monoclonal antibody or antigen-binding fragment thereof that specifically binds to RSV-F, wherein the antibody or fragment thereof exhibits one or more of the following characteristics: (i) comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338, or a substantially similar sequence thereof having at least 90%, at least 95%, at least 98% or at least 99% sequence identity; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346, or a substantially similar sequence thereof having at least 90%, at least 95%, at least 98% or at least 99% sequence identity; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336 and 352, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340, or a substantially similar sequence thereof having at least 90%, at least 95%, at least 98% or at least 99% sequence identity; (v) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342, or a substantially similar sequence thereof having at least 90%, at least 95%, at least 98% or at least 99% sequence identity; (vi) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348, or a substantially similar sequence thereof having at least 90%, at least 95%, at least 98% or at least 99% sequence identity; (vii) and a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350, or a substantially similar sequence thereof having at least 90%, at least 95%, at least 98% or at least 99% sequence identity; (viii) exhibits a $K_D$ ranging from about $1 \times 10^{-7}$ M to about $6 \times 10^{-10}$ M as measured by surface plasmon resonance; (ix) is capable of neutralizing respiratory syncytial virus subtype A and/or subtype B strains in vitro; (x) demonstrates the ability to significantly reduce the viral load in a mouse model of RSV infection when administered at a dose ranging from about 0.05 mg/kg to about 0.15 mg/kg; (xi) demonstrates a 1 to 2 logs greater reduction of nasal and/or lung viral titers in a cotton rat model of RSV infection at a dose ranging from about 0.62 mg/kg to about 5.0 mg/kg when compared to palivizumab; (xii) demonstrates an effective dose 99 ($ED_{99}$) ranging from about 0.15 mg/kg to about 2.5 mg/kg when administered in an animal model of RSV infection (e.g. a mouse model or a cotton rat model); or (xiii) demonstrates a half maximal inhibitory concentration ($IC_{50}$) of about 2 pM to about 15 pM in a microneutralization assay specific for RSV subtype A strains of RSV and a half maximal inhibitory concentration ($IC_{50}$) of about 6 pM to about 100 pM in a microneutralization assay.

In one embodiment, the invention provides a fully human monoclonal antibody or antigen-binding fragment thereof that specifically binds to RSV-F, wherein the antibody or fragment thereof exhibits one or more of the following characteristics: (i) comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338, or a substantially similar sequence thereof having at least 90%, at least 95%, at least 98% or at least 99% sequence identity; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346, or a substantially similar sequence thereof having at least 90%, at least 95%, at least 98% or at least 99% sequence identity; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336 and 352, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340, or a substantially similar sequence thereof having at least 90%, at least 95%, at least 98% or at least 99% sequence identity; (v) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342, or a substantially similar sequence thereof having at least 90%, at least 95%, at least 98% or at least 99% sequence identity; (vi) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348, or a substantially similar sequence thereof having at least 90%, at least 95%, at least 98% or at least 99% sequence identity; (vii) and a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350, or a substantially similar sequence thereof having at least 90%, at least 95%, at least 98% or at least 99% sequence identity; (viii) exhibits a $K_D$ ranging from about $1 \times 10^{-7}$ M to about $6 \times 10^{-10}$ M; (ix) is capable of neutralizing respiratory syncytial virus subtype A and/or subtype B strains in vitro; (x) demonstrates the ability to significantly reduce the viral load in an animal model of RSV infection (e.g. a mouse model) when administered at a dose ranging from about 0.05 mg/kg to about 0.15 mg/kg; (xi) demonstrates a 1 to 2 logs greater reduction of nasal and/or lung viral titers in an animal model of RSV infection (e.g. a cotton rat model) at a dose ranging from about 0.62 mg/kg to about 5.0 mg/kg when compared to palivizumab; (xii) demonstrates an effective dose 99 ($ED_{99}$) ranging from about 0.05 mg/kg to about 2.5 mg/kg when administered in an animal model of RSV infection (e.g. a mouse model or a cotton rat model); (xiii) demonstrates an $ED_{99}$ that is about 2 to 3 fold lower than the $ED_{99}$ for palivizumab or motavizumab; (xiv) demonstrates a neutralization potency against one or more subtype A laboratory strains of RSV that is about 15 to 17 fold improvement over palivizumab, or demonstrates a neutralization potency against one or more subtype A clinical strains of RSV that is about a 10-22 fold improvement over palivizumab; (xv) demonstrates a neutralization potency against one or more subtype B laboratory strains of RSV that is about a 2 to 5 fold improvement over palivizumab; (xvi) demonstrates a neutralization potency against one or more subtype A laboratory strains or subtype A clinical strains of RSV that is about 0.5 to 2 fold improvement over AM-22; (xvii) demonstrates a neutralization potency against one or more subtype B laboratory strains of RSV that is about a 2.5 to 17 fold improvement over AM-22.

In one embodiment, the invention provides a fully human monoclonal antibody or antigen-binding fragment thereof that specifically binds to RSV-F, wherein the antibody or fragment thereof exhibits one or more of the following characteristics: (i) comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338, or a substantially similar sequence thereof having at least 90%, at least 95%, at least 98% or at least 99% sequence identity; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346, or a substantially similar sequence thereof having at least 90%, at least 95%, at least 98% or at least 99% sequence identity; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336 and 352, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340, or a substantially similar sequence thereof having at least 90%, at least 95%, at least 98% or at least 99% sequence identity; (v) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342, or a substantially similar sequence thereof having at least 90%, at least 95%, at least 98% or at least 99% sequence identity; (vi) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348, or a substantially similar sequence thereof having at least 90%, at least 95%, at least 98% or at least 99% sequence identity; (vii) and a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350, or a substantially similar sequence thereof having at least 90%, at least 95%, at least 98% or at least 99% sequence identity; (viii) exhibits a $K_D$ ranging from about $1 \times 10^{-7}$ M to about $6 \times 10^{-10}$ M; (ix) is capable of neutralizing respiratory syncytial virus subtype A and/or subtype B strains in vitro; (x) demonstrates the ability to significantly reduce the viral load in an mammal having an RSV infection; (xi) interacts with an amino acid sequence comprising amino acid residues ranging from about position 161 to about position 188 of SEQ ID NO: 354; (xii) interacts with either the serine at position 173 of SEQ ID O: 354, or the threonine at position 174 of SEQ ID NO: 354, or both the serine at position 173 of SEQ ID O: 354, and the threonine at position 174 of SEQ ID NO: 354;

(xiii) inhibits fusion of RSV to the host cell; (xiv) does not cross-compete with palivizumab or AM-22 for binding to RSV-F.

In one embodiment, the invention provides an isolated human monoclonal antibody that specifically binds Respiratory Syncytial Virus F protein (RSV-F), or an antigen-binding fragment thereof, wherein the antibody or antigen-binding fragment thereof interacts with an amino acid sequence comprising amino acid residues ranging from about position 161 to about position 188 of SEQ ID NO: 354.

In one embodiment, the invention provides an isolated human monoclonal antibody that specifically binds RSV-F, or an antigen-binding fragment thereof, wherein the antibody or antigen-binding fragment thereof interacts with at least one amino acid sequence selected from the group consisting of SEQ ID NO: 355 and 356.

In one embodiment, the invention provides an isolated human monoclonal antibody that specifically binds RSV-F, or an antigen-binding fragment thereof, wherein the antibody or antigen-binding fragment thereof interacts with at least one amino acid residue within residues 161 through 188 of SEQ ID NO: 354.

In one embodiment, the invention provides an isolated human monoclonal antibody that specifically binds RSV-F, or an antigen-binding fragment thereof, wherein the antibody or antigen-binding fragment thereof interacts with at least one amino acid residue within SEQ ID NO: 355 or SEQ ID NO:356.

In one embodiment, the invention provides an isolated human monoclonal antibody that specifically binds RSV-F, or an antigen-binding fragment thereof, wherein the antibody or antigen-binding fragment thereof interacts with either the serine at position 173 of SEQ ID NO: 354, or the threonine at position 174 of SEQ ID NO: 354, or both the serine at position 173 of SEQ ID NO: 354 and the threonine at position 174 of SEQ ID NO: 354.

In one embodiment, the invention provides an isolated human monoclonal antibody or antigen-binding fragment thereof that specifically binds to Respiratory Syncytial Virus F protein (RSV-F), wherein the antibody or antigen-binding fragment thereof interacts with an amino acid sequence comprising amino acid residues ranging from about position 161 to about position 188 of SEQ ID NO: 354, and wherein the antibody or antigen-binding fragment thereof comprises three heavy chain CDRs (HCDR1, HCDR2 and HCDR3) contained within the heavy chain variable region (HCVR) amino acid sequence of SEQ ID NO: 274; and three light chain CDRs (LCDR1, LCDR2 and LCDR3) contained within the light chain variable region (LCVR) amino acid sequence of SEQ ID NO: 282.

In one embodiment, the invention provides an isolated human monoclonal antibody or antigen-binding fragment thereof that specifically binds to Respiratory Syncytial Virus F protein (RSV-F), wherein the antibody or antigen-binding fragment thereof comprises:
 (a) a HCDR1 domain comprising the amino acid sequence of SEQ ID NO: 276;
 (b) a HCDR2 domain comprising the amino acid sequence of SEQ ID NO: 278;
 (c) a HCDR3 domain comprising the amino acid sequence of SEQ ID NO: 280;
 (d) a LCDR1 domain comprising the amino acid sequence of SEQ ID NO: 284;
 (e) a LCDR2 domain comprising the amino acid sequence of SEQ ID NO: 286; and
 (f) a LCDR3 domain comprising the amino acid sequence of SEQ ID NO: 288.

In one embodiment, the invention provides an isolated human monoclonal antibody, or an antigen-binding fragment thereof, that binds specifically to RSV-F, wherein the antibody comprises the three HCDRs contained within the heavy chain variable region (HCVR) amino acid sequence of SEQ ID NO: 274; and the three light chain CDRs (LCDR1, LCDR2 and LCDR3) contained within the light chain variable region (LCVR) amino acid sequence of SEQ ID NO: 282 and wherein the antibody or antigen-binding fragment thereof interacts with at least one amino acid sequence selected from the group consisting of SEQ ID NO: 355 and 356.

In one embodiment, the invention provides an isolated human monoclonal antibody, or an antigen-binding fragment thereof, that binds specifically to RSV-F, wherein the antibody comprises the three HCDRs contained within the heavy chain variable region (HCVR) amino acid sequence of SEQ ID NO: 274; and the three light chain CDRs (LCDR1, LCDR2 and LCDR3) contained within the light chain variable region (LCVR) amino acid sequence of SEQ ID NO: 282 and wherein the antibody or antigen-binding fragment thereof interacts with at least one amino acid residue within residues 161 through 188 of SEQ ID NO: 354.

In one embodiment, the invention provides an isolated human monoclonal antibody, or an antigen-binding fragment thereof, that binds specifically to RSV-F, wherein the antibody comprises the three HCDRs contained within the heavy chain variable region (HCVR) amino acid sequence of SEQ ID NO: 274; and the three light chain CDRs (LCDR1, LCDR2 and LCDR3) contained within the light chain variable region (LCVR) amino acid sequence of SEQ ID NO: 282 and wherein the antibody or antigen-binding fragment thereof interacts with at least one amino acid residue within SEQ ID NO: 355 or SEQ ID NO:356.

In one embodiment, the invention provides an isolated human monoclonal antibody, or an antigen-binding fragment thereof, that binds specifically to RSV-F, wherein the antibody comprises the three HCDRs contained within the heavy chain variable region (HCVR) amino acid sequence of SEQ ID NO: 274; and the three light chain CDRs (LCDR1, LCDR2 and LCDR3) contained within the light chain variable region (LCVR) amino acid sequence of SEQ ID NO: 282, wherein the antibody or antigen-binding fragment thereof interacts with either the serine at position 173 of SEQ ID NO: 354, or the threonine at position 174 of SEQ ID NO: 354, or both the serine at position 173 of SEQ ID NO: 354 and the threonine at position 174 of SEQ ID NO: 354.

In one embodiment, the invention provides an isolated human antibody, or an antigen-binding fragment thereof that does not cross-compete for binding to RSV-F with palivizumab, or motavizumab.

In one embodiment, the invention provides an isolated human antibody, or an antigen-binding fragment thereof that does not cross-compete for binding to RSV-F with AM-22.

In one embodiment, the invention provides an isolated human antibody, or an antigen-binding fragment thereof that does not bind the same epitope on RSV-F as palivizumab.

In one embodiment, the invention provides an isolated human antibody, or an antigen-binding fragment thereof that does not bind the same epitope on RSV-F as motavizumab.

In one embodiment, the invention provides an isolated human monoclonal antibody, or an antigen-binding fragment thereof that does not bind to an epitope on RSV-F ranging from about amino acid residue 255 to about amino acid residue 276 of SEQ ID NO: 354.

In one embodiment, the isolated human monoclonal antibody, or an antigen-binding fragment thereof does not bind to the same epitope on RSV-F as palivizumab, wherein the epitope ranges from about amino acid residue 255 to about amino acid residue 276 of SEQ ID NO: 354.

In a second aspect, the invention provides nucleic acid molecules encoding antibodies or fragments thereof that specifically bind to RSV-F. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33,49, 65, 81, 97, 113, 129, 145, 161, 177, 193, 209, 225, 241, 257, 273, 289, 305, 321, and 337 or a substantially identical sequence having at least 90%, at least 95%, at least 98%, or at least 99% homology thereof.

In one embodiment, the HCVR is encoded by a nucleic acid sequence selected from the group consisting of SEQ ID NO: 273 and 337.

In one embodiment, the antibody or fragment thereof further comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, and 345, or a substantially identical sequence having at least 90%, at least 95%, at least 98%, or at least 99% homology thereof.

In one embodiment, the LCVR is encoded by a nucleic acid sequence selected from the group consisting of SEQ ID NO: 281 and 345.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, and 343 or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, and 351, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, and 339, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, and 341, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, and 347, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, and 349, or a substantially similar sequence thereof having at least 90%, at least 95%, at least 98% or at least 99% sequence identity.

In a third aspect, the invention features a human antibody or antigen-binding fragment specific for RSV-F comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences.

The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention provides a pharmaceutical composition comprising at least one isolated fully human monoclonal antibody or antigen-binding fragment thereof that binds to RSV-F and a pharmaceutically acceptable carrier or diluent. In one embodiment, the invention provides a pharmaceutical composition comprising two fully human monoclonal antibodies or antigen-binding fragments thereof, which either bind to the same epitope or bind to two different epitopes on RSV-F and a pharmaceutically acceptable carrier or diluent. It is to be understood that any combination of antibodies as described herein may be used in a pharmaceutical composition to achieve the desired results in the patient population in need of such therapy. For example, two antibodies that recognize and/or bind RSV-F may be used in a composition. Alternatively, two antibodies, one that recognizes and/or binds RSV-F and a second antibody that binds to another antigen on RSV (e.g. RSV-G) may be used in a composition. In one embodiment, two antibodies, one that recognizes and/or binds RSV-F and a second antibody that binds to a metapneumovirus antigen may be used in a composition. Alternatively, two or more antibodies may be used in a composition, one that recognizes and/or binds to RSV-F, one that binds to a metapneumovirus antigen and one that binds to an influenza virus antigen or to any other virus that causes respiratory diseases.

In one embodiment, the pharmaceutical composition comprises an antibody that binds RSV-F and has a HCVR/LCVR amino acid sequence pair selected from the group consisting of SEQ ID NOs: 274/282 and 338/346.

In one embodiment, the pharmaceutical composition comprises an antibody that binds RSV-F and has a HCVR/LCVR amino acid sequence pair consisting of SEQ ID NOs: 274/282.

In one embodiment, the pharmaceutical composition comprises an antibody that binds RSV-F and has a HCVR/LCVR amino acid sequence pair consisting of SEQ ID NOs: 338/346.

In one embodiment, the pharmaceutical composition comprises at least one antibody that binds RSV-F, wherein the antibody comprises the three heavy chain complementarity determining regions (HCDR1, HCDR2 and HCDR3) contained within any one of the heavy chain variable region (HCVR) amino acid sequences selected from the group consisting of SEQ ID NOs: 274 and 338; and the three light chain complementarity determining regions (LCDR1, LCDR2 and LCDR3) contained within any one of the light chain variable region (LCVR) amino acid sequences selected from the group consisting of SEQ ID NOs: 282 and 346.

In one embodiment, the antibodies of the invention, or compositions containing one or more antibodies of the invention may be used to neutralize RSV from any subtype A or subtype B strain of RSV.

In one embodiment, the invention features a composition, which is a combination of an antibody or antigen-binding fragment of an antibody of the invention, and a second therapeutic agent.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with the antibody or fragment thereof of the invention, for example, an antiviral agent (e.g. ribavirin), a vaccine specific for RSV, or a vaccine specific for influenza virus, or a vaccine specific for metapneumovirus (MPV), an siRNA specific for an RSV antigen, an siRNA specific for an influenza virus antigen, an siRNA specific for a metapneumovirus (MPV) antigen, a second antibody specific for an RSV antigen, or a metapneumovirus (MPV) antigen, or an influenza antigen, an anti-IL4R antibody, an anti-RSV-G antibody or a NSAID. In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

When multiple therapeutics are co-administered, dosages may be adjusted accordingly, as is recognized in the pertinent art.

A fifth aspect of the invention provides a method for preventing infection with respiratory syncytial virus in a patient in need thereof, or for treating a patient suffering from an infection with RSV, or for ameliorating at least one symptom or complication associated with the RSV infection, the method comprising administering one or more antibodies or antigen-binding fragments thereof as described herein, or a pharmaceutical composition comprising one or more antibodies of the invention or fragments thereof, as described herein, to a patient in need thereof, such that the RSV infection is prevented, or at least one symptom or complication associated with the infection is ameliorated, alleviated or reduced in severity and/or duration.

In a related embodiment, the invention provides a pharmaceutical composition comprising one or more antibodies of the invention, alone or in combination with a second therapeutic agent, for use in preventing a respiratory syncytial virus (RSV) infection in a patient in need thereof, or for treating a patient suffering from an RSV infection, or for ameliorating at least one symptom or complication associated with the infection, wherein the infection is either prevented, or at least one symptom or complication associated with the infection is prevented, ameliorated, or lessened in severity and/or duration.

In one embodiment, the invention provides a pharmaceutical composition comprising one or more antibodies of the invention, alone or in combination with a second therapeutic agent in the manufacture of a medicament for preventing a respiratory syncytial virus (RSV) infection in a patient in need thereof, or for treating a patient suffering from an RSV infection, or for ameliorating at least one symptom or complication associated with the infection, wherein the infection is either prevented, or at least one symptom or complication associated with the infection is prevented, ameliorated, or lessened in severity and/or duration.

In one embodiment, a patient in need of treatment with an antibody of the invention, or an antigen-binding fragment thereof is a patient who may experience a more severe form of the RSV infection due to an underlying or pre-existing medical condition. In one embodiment, the method provides for preventing the development of infection with RSV in a patient at risk thereof, the method comprising administering to the patient an effective amount of an antibody or an antigen-binding fragment thereof that binds to the F protein of RSV, or a pharmaceutical composition comprising an effective amount of an antibody or an antigen-binding fragment thereof that binds to the F protein of RSV such that the infection is either prevented, ameliorated, or lessened in severity and/or duration, or at least one symptom or complication associated with the infection is prevented, or ameliorated, or lessened in severity or duration. In one embodiment, the administering of the isolated human RSV-F antibody or an antigen-binding fragment thereof results in prevention of recurrent wheezing in the patient. In one embodiment, the administering of the isolated human RSV-F antibody or an antigen-binding fragment thereof results in prevention of RSV-associated asthma in a child. In one embodiment, the administering of the isolated human RSV-F antibody or an antigen-binding fragment thereof results in prevention of an RSV infection caused by a subtype A or a subtype B respiratory syncytial virus.

In one embodiment, the at least one symptom or complication associated with the RSV infection that may be treated with an antibody of the invention, or an antigen-binding fragment thereof, may be selected from the group consisting of hypoxia, a bluish skin color due to lack of oxygen, breathing difficulty (e.g.,rapid breathing or shortness of breath), cough, croupy cough ("seal bark" cough), fever, nasal flaring, stuffy nose, wheezing, pneumonia, apnea, dehydration, poor feeding, altered mental status, decreased appetite, or bronchiolitis.

In one embodiment, the patient at risk of developing an RSV infection, who may benefit from treatment with the antibodies of the invention, or with a composition comprising one or more antibodies of the invention, may be selected from the group consisting of a pre-term infant, a full term infant who is compromised due to some other underlying medical condition and/or is exposed during the peak season for RSV, a child greater than or equal to one year of age with or without an underlying medical condition (e.g. congenital heart disease, chronic lung disease, cystic fibrosis, immunodeficiency, a neuromuscular disorder), an institutionalized or hospitalized patient, an elderly patient (≥65 years of age) with or without an underlying medical condition such as congestive heart failure or chronic obstructive pulmonary disease), a patient who is immunocompromised due to underlying illness or due to administration of immunosuppressive therapeutics, a patient who has some underlying medical condition that may pre-dispose them to acquiring an RSV infection, for example, chronic obstructive pulmonary disease (COPD), congestive heart failure, cystic fibrosis, bronchopulmonary dysplasia, airway malfunction, chronic lung disease, a cancer patient, or a transplant patient who is on immunosuppressive therapy.

In one embodiment, a patient who is a candidate for therapy with an antibody of the invention may suffer from a condition resulting from a compromised pulmonary, cardiovascular, neuromuscular, or immune system. The condition may be selected from the group consisting of an abnormality of the airway, a chronic lung disease, a chronic heart disease, a neuromuscular disease that compromises the handling of respiratory secretions and immunosuppression. The chronic lung disease may be chronic obstructive pulmonary disease (COPD), cystic fibrosis, or bronchopulmonary dysplasia. The chronic heart disease may be congestive heart failure (CHF), or congenital heart disease. The neuromuscular disease or condition may be a neurodegenerative disease, or an inability to handle and/or eliminate respiratory secretions due to an injury or accident to the nervous system, e.g. a stroke, or a spinal cord injury. The immunosuppression may be the result of severe combined immunodeficiency or severe acquired immunodeficiency, or may be a result of any other infectious disease or cancerous condition that leads to immunosuppression, or is a result of treatment with immunosuppressant drug therapy or radiation therapy.

In one embodiment, the antibody is administered prophylactically (administered prior to development of the infection) to a patient at risk for developing an RSV infection, or at risk for developing at least one symptom or complication associated with the RSV infection. The patients who are candidates for treatment with the antibodies of the invention may be administered the compositions comprising one or more antibodies by any route of delivery suitable for administration, including but not limited to intravenous injection, intramuscular injection, or subcutaneous injection.

In one embodiment, the antibody is administered therapeutically (administered after the development of the infection) to a patient to ameliorate or reduce the severity and/or duration of at least one symptom or complication associated with the RSV infection.

In one embodiment, the antibodies of the invention may be administered to the patient in combination with one or more therapeutic agents useful for treating a RSV infection. The one or more therapeutic agents may be selected from the group consisting of an antiviral agent; a vaccine specific for RSV, a vaccine specific for influenza virus, or a vaccine specific for metapneumovirus (MPV); an siRNA specific for an RSV antigen or a metapneumovirus (MPV) antigen; a second antibody specific for an RSV antigen or a metapneumovirus (MPV) antigen; an anti-IL4R antibody, an antibody specific for an influenza virus antigen, an anti-RSV-G antibody and a NSAID.

A sixth aspect of the invention provides an immunogenic composition, or a vaccine, that when administered to an individual, preferably a human, induces an immune response in such individual to a Respiratory Syncytial Virus (RSV) antigen.

In one embodiment, the immunogenic composition, or vaccine, comprises an RSV antigen, for example, an RSV-F protein, polypeptide, or an immunogenic fragment thereof, or an epitope contained within and/or obtained from an antigen of the RSV-F polypeptide or a fragment thereof, and/or comprises DNA and/or RNA which encodes and expresses an epitope from an antigen of the RSV-F polypeptide, or other polypeptides of the invention.

In one embodiment of the invention, the immunogenic composition, or vaccine, may comprise the RSV-F protein as shown in SEQ ID NO: 354. In one embodiment of the invention, the immunogenic composition, or vaccine, may comprise a RSV-F polypeptide fragment comprising residues 161 through 188 of SEQ ID NO: 354. In one embodiment of the invention, the immunogenic composition, or vaccine, may comprise one or more amino acid residues contained within SEQ ID NO: 355 and/or SEQ ID NO: 356. In one embodiment of the invention, the immunogenic composition, or vaccine, may comprise SEQ ID NO: 355 and/or SEQ ID NO: 356.

In a related aspect, the invention provides a method for inducing an immune response in an individual, particularly a mammal, preferably humans, by administering to an individual an immunogenic composition, or a vaccine, comprising a RSV-F protein, or an immunogenic fragment thereof, or a RSV-F antigen or an immunogenic fragment thereof comprising one or more epitopes contained within the RSV-F antigen or fragment thereof, adequate to produce an antibody and/or a T cell immune response to protect the individual from infection, particularly infection with Respiratory Syncytial Virus (RSV).

In one embodiment, methods are provided for using the immunogenic compositions, or vaccines of the invention for inducing an immune response that results in inhibiting, or slowing the progression of cell to cell viral spread. Methods are also provided for ameliorating at least one symptom associated with RSV infection by administering an immunogenic composition, or a vaccine, comprising at least one RSV-F antigen, or one or more epitopes contained within the RSV-F antigen, which when administered will induce an immune response in the individual.

For example, in one embodiment the invention provides a method of inducing an immune response in an individual comprising delivering to the individual an immunogenic composition, or vaccine comprising, an RSV-F antigen (e.g. the amino acid sequence shown in SEQ ID NO: 354), or an antigenic fragment thereof, (e.g. a polypeptide comprising residues 161 through 188 of SEQ ID NO: 354), or a nucleic acid vector comprising a nucleotide sequence to direct expression of such viral polypeptide, or a fragment or a variant thereof, in vivo in order to induce an immune response.

In one embodiment of the invention, the polypeptide to be used in an immunogenic composition or in a vaccine for inducing an immune response in an individual comprises residues 161 through 188 of SEQ ID NO: 354. In one embodiment of the invention, the polypeptide to be used in an immunogenic composition or in a vaccine for inducing an immune response in an individual comprises one or more amino acid residues contained within SEQ ID NO: 355 and/or SEQ ID NO: 356. In one embodiment of the invention, the polypeptide to be used in an immunogenic composition or in a vaccine for inducing an immune response in an individual comprises SEQ ID NO: 355 and/or SEQ ID NO: 356. In one embodiment of the invention, the immunogenic composition, or vaccine, may elicit an antibody response or a T cell response specific for the RSV-F antigen of RSV, wherein the antibodies generated interact with either the serine at position 173 of SEQ ID NO: 354, or the threonine at position 354, or both the serine at position 173 of SEQ ID NO: 354 and the threonine at position 174 of SEQ ID NO: 354.

In certain embodiments of the invention, the immunogenic composition, or vaccine may comprise an immunogenic polypeptide and/or polynucleotide of the invention, or a combination thereof, together with a suitable carrier/excipient, such as a pharmaceutically acceptable carrier/excipient. The immunogenic composition, or vaccine of the invention may also include adjuvants for enhancing the immunogenicity of the formulation.

In certain embodiments, it is advantageous for the RSV-F antigens or fragments thereof to be formulated into immunogenic compositions, or vaccines that comprise immunogenic, preferably immunologically effective, amounts of additional antigens to elicit immunity to other pathogens, preferably viruses and/or bacteria. Such additional antigens may include an influenza virus antigen, an antigen from metapneumovirus or from a coronavirus, an antigen from Haemophilus influenzae, Streptococcus pneumonia, or Bordetella pertussis. Other RSV antigens may be included in the immunogenic compositions, or vaccines, such as the RSV-G glycoprotein, or immunogenic fragments thereof, the HN protein, or derivatives thereof.

DETAILED DESCRIPTION

Figure 1:
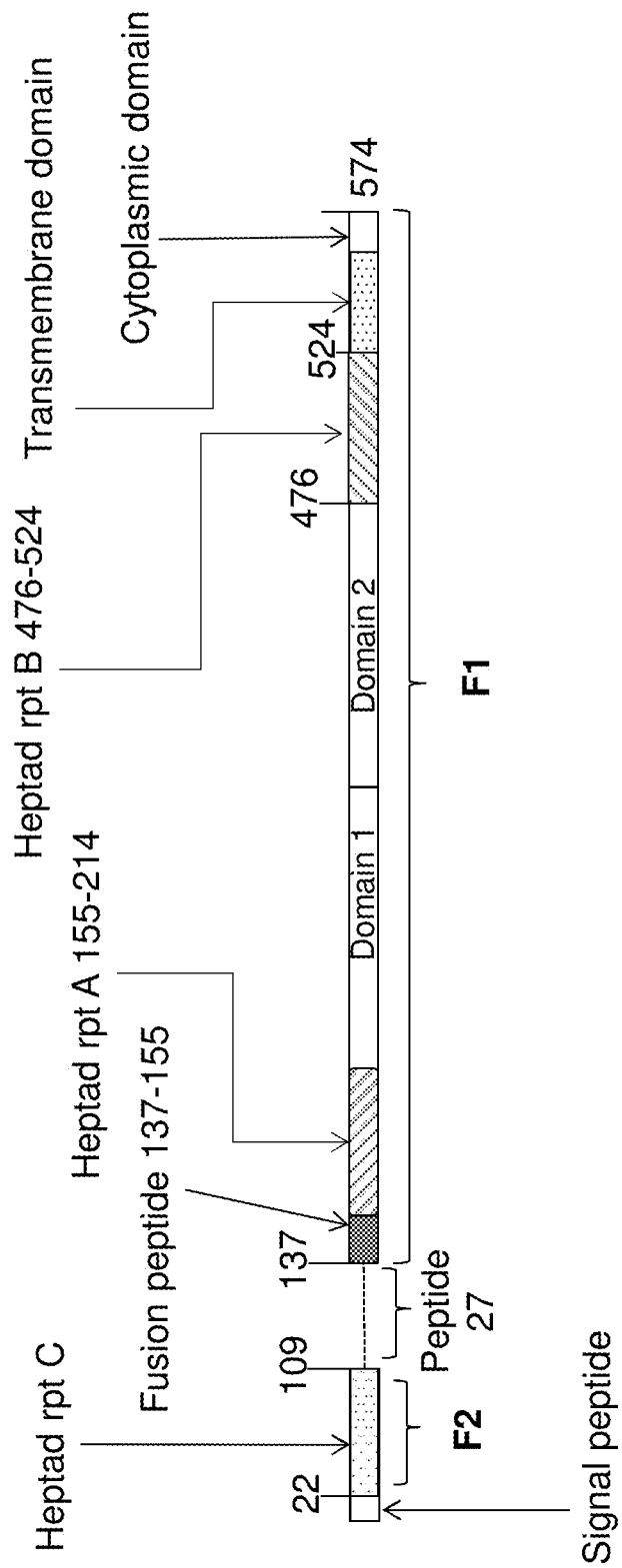
FIG. 1 shows a schematic diagram of the RSV-F protein.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.
Definitions "Respiratory Syncytial Virus-F protein", also referred to as "RSV-F" is a type I transmembrane surface protein, which has an N terminal cleaved signal peptide and a membrane anchor near the C terminus (Collins, P. L. et al., (1984), PNAS (USA) 81:7683-7687). The RSV-F protein is synthesized as an inactive 67 KDa precursor denoted as F0 (Calder, L. J.; et al., Virology (2000), 271, 122-131. The F0 protein is activated proteolytically in the Golgi complex by a furin-like protease at two sites, yielding two disulfide linked polypeptides, F2 and F1, from the N and C terminal, respectively. There is a 27 amino acid peptide released called "pep27". There are furin cleavage sites (FCS) on either side of the pep27 (Collins, P. L.; Mottet, G. (1991), J. Gen. Virol, 72: 3095-3101; Sugrue, R. J, et al. (2001), J. Gen. Virol, 82,1375-1386). The F2 subunit consists of the Heptad repeat C (HRC), while the F1 contains the fusion polypeptide (FP), heptad repeat A (HRA), domain I, domain II, heptad repeat B (HRB), transmembrane (TM) and cytoplasmic domain (CP) (See Sun, Z. et al. Viruses (2013), 5:211-225). The RSV-F protein plays a role in fusion of the virus particle to the cell membrane, and is expressed on the surface of infected cells, thus playing a role in cell to cell transmission of the virus and syncytia formation. The amino acid sequence of the RSV-F protein is provided in GenBank as accession number AAX23994 and is also referred to herein as SEQ ID NO: 354.

A genetically engineered construct of the RSV-F protein is shown herein as having the amino acid sequence of SEQ ID NO: 353.

The term "laboratory strain" as used herein refers to a strain of RSV (subtype A or B) that has been passaged extensively in in vitro cell culture. A "laboratory strain" can acquire adaptive mutations that may affect their biological properties. A "clinical strain" as used herein refers to an RSV isolate (subtype A or B), which is obtained from an infected individual and which has been isolated and grown in tissue culture at low passage.

The term "effective dose 99" or "$ED_{99}$" refers to the dosage of an agent that produces a desired effect of 99% reduction of viral forming plaques relative to the isotype (negative) control. In the present invention, the $ED_{99}$ refers to the dosage of the anti-RSV-F antibodies that will neutralize the virus infection (ie.g. reduce 99% of viral load) in vivo, as described in Example 5.

The term "IC50" refers to the "half maximal inhibitory concentration", which value measures the effectiveness of compound (e.g. anti-RSV-F antibody) inhibition towards a biological or biochemical utility. This quantitative measure indicates the quantity required for a particular inhibitor to inhibit a given biological process by half.

"Palivizumab", also referred to as "SYNAGIS®", is a humanized anti-RSV-F antibody with heavy and light chain variable domains having the amino acid sequences as set forth in U.S. Pat. No. 7,635,568 and 5,824,307 (also shown herein as SEQ ID NO: 361 for the heavy chain of the antibody and SEQ ID NO: 362 for the light chain of the antibody). This antibody, which immunospecifically binds to the RSV-F protein, is currently FDA-approved for the passive immunoprophylaxis of serious RSV disease in high-risk children and is administered intramuscularly at recommended monthly doses of 15 mg/kg of body weight throughout the RSV season (November through April in the northern hemisphere). SYNAGIS® is composed of 95% human and 5% murine antibody sequences. See also Johnson et al., (1997), J. Infect. Diseases 176:1215-1224.

"Motavizumab", also referred to as "NUMAX™", is an enhanced potency RSV-F-specific humanized monoclonal antibody derived by in vitro affinity maturation of the complementarity-determining regions of the heavy and light chains of palivizumab. For reference purposes, the amino acid sequence of the NUMAX™ antibody is disclosed in U.S Patent Publication 2003/0091584 and in U.S. Pat. No. 6,818,216 and in Wu et al., (2005) J. Mol. Bio. 350(1):126-

144 and in Wu, et al. (2007) J. Mol. Biol. 368:652-665. It is also shown herein as SEQ ID NO: 359 for the heavy chain and as SEQ ID NO: 360 for the light chain of the antibody.

As used herein, the terms "treat," "treatment" and "treating" refer to the reduction or amelioration of the progression, severity, and/or duration of an upper and/or lower respiratory tract RSV infection, otitis media, or a symptom or respiratory condition related thereto (such as asthma, wheezing, or a combination thereof) resulting from the administration of one or more therapies (including, but not limited to, the administration of one or more prophylactic or therapeutic agents). In specific embodiments, such terms refer to the reduction or inhibition of the replication of RSV, the inhibition or reduction in the spread of RSV to other tissues or subjects (e.g., the spread to the lower respiratory tract), the inhibition or reduction of infection of a cell with a RSV, or the amelioration of one or more symptoms associated with an upper and/or lower respiratory tract RSV infection or otitis media.

As used herein, the terms "prevent," "preventing," and "prevention" refer to the prevention or inhibition of the development or onset of an upper and/or lower respiratory tract RSV infection, otitis media or a respiratory condition related thereto in a subject, the prevention or inhibition of the progression of an upper respiratory tract RSV infection to a lower respiratory tract RSV infection, otitis media or a respiratory condition related thereto resulting from the administration of a therapy (e.g., a prophylactic or therapeutic agent), the prevention of a symptom of an upper and/or lower tract RSV infection, otitis media or a respiratory condition related thereto, or the administration of a combination of therapies (e.g., a combination of prophylactic or therapeutic agents).

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully monoclonal antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "recombinant" generally refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins used in the immunogenic compositions of the invention may be isolated from a natural source or produced by genetic engineering methods.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to RSV-F. Moreover, multi-specific antibodies that bind to RSV-F protein and one or more additional antigens or a bi-specific that binds to two different regions of RSV-F are nonetheless considered antibodies that "specifically bind", as used herein.

The term "high affinity" antibody refers to those mAbs having a binding affinity to RSV-F, expressed as $K_D$, of at least $10^{-9}$ M; more preferably $10^{-10}$ M, more preferably $10^{-11}$ M, more preferably $10^{-12}$ M as measured by surface plasmon resonance, e.g., BIACORE™ or solution-affinity ELISA.

By the term "slow off rate", "Koff" or "kd" is meant an antibody that dissociates from RSV-F, with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retains the ability to bind to RSV-F.

The specific embodiments, antibody or antibody fragments of the invention may be conjugated to a therapeutic moiety ("immunoconjugate"), such as an antibiotic, a second anti-RSV-7 antibody, a vaccine, or a toxoid, or any other therapeutic moiety useful for treating a RSV infection.

An "isolated antibody", as used herein, is intended to refer to an antibody that is substantially free of other antibodies (Abs) having different antigenic specificities (e.g., an isolated antibody that specifically binds RSV-F, or a fragment thereof, is substantially free of Abs that specifically bind antigens other than RSV-F.

A "blocking antibody" or a "neutralizing antibody", as used herein (or an "antibody that neutralizes RSV-F activity"), is intended to refer to an antibody whose binding to RSV-F results in inhibition of at least one biological activity of RSV-F. For example, an antibody of the invention may aid in blocking the fusion of RSV to a host cell, or prevent syncytia formation, or prevent the primary disease caused by RSV. Alternatively, an antibody of the invention may demonstrate the ability to ameliorate at least one symptom of the RSV infection. This inhibition of the biological activity of RSV-F can be assessed by measuring one or more indicators of RSV-F biological activity by one or more of several standard in vitro assays (such as a neutralization assay, as described herein) or in vivo assays known in the art (for example, animal models to look at protection from challenge with RSV following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

An "immunogenic composition" relates to a composition containing an antigen/immunogen, e.g. a microorganism, such as a virus or a bacterium, or a component thereof, a protein, a polypeptide, a fragment of a protein or polypeptide, a whole cell inactivated, subunit or attenuated virus, or a polysaccharide, or combination thereof, administered to stimulate the recipient's humoral and/or cellular immune systems to one or more of the antigens/immunogens present in the immunogenic composition. The immunogenic compositions of the present invention can be used to treat a human susceptible to RSV infection, by means of administering the immunogenic compositions via a systemic route. These administrations can include injection via the intramuscular (i.m.), intradermal (i.d.), intranasal or inhalation route, or subcutaneous (s.c.) routes; application by a patch or other transdermal delivery device. In one embodiment, the immunogenic composition may be used in the manufacture of a vaccine or in the elicitation of polyclonal or monoclonal antibodies that could be used to passively protect or treat a mammal.

The terms "vaccine" or "vaccine composition", which are used interchangeably, refer to a composition comprising at least one immunogenic composition that induces an immune response in an animal.

In one embodiment of the invention, the protein of interest comprises an antigen. The terms "antigen," "immunogen," "antigenic," "immunogenic," "antigenically active," and "immunologically active" when made in reference to a molecule, refer to any substance that is capable of inducing a specific humoral and/or cell-mediated immune response. In one embodiment, the antigen comprises an epitope, as defined above.

"Immunologically protective amount", as used herein, is an amount of an antigen effective to induce an immunogenic response in the recipient that is adequate to prevent or ameliorate signs or symptoms of disease, including adverse health effects or complications thereof. Either humoral immunity or cell-mediated immunity or both can be induced. The immunogenic response of an animal to a composition can be evaluated, e.g., indirectly through measurement of antibody titers, lymphocyte proliferation assays, or directly through monitoring signs and symptoms after challenge with the microorganism. The protective immunity conferred by an immunogenic composition or vaccine can be evaluated by measuring, e.g., reduction of shed of challenge organisms, reduction in clinical signs such as mortality, morbidity, temperature, and overall physical condition, health and performance of the subject. The immune response can comprise, without limitation, induction of cellular and/or humoral immunity. The amount of a composition or vaccine that is therapeutically effective can vary, depending on the particular organism used, or the condition of the animal being treated or vaccinated.

"Immune response", or "immunological response" as used herein, in a subject refers to the development of a humoral immune response, a cellular-immune response, or a humoral and a cellular immune response to an antigen/immunogen. A "humoral immune response" refers to one that is at least in part mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art. "Immunogenicity", as used herein, refers to the capability of a protein or polypeptide to elicit an immune response directed specifically against a bacteria or virus that causes the identified disease, General Description Respiratory syncytial virus (RSV) is a negative sense, single stranded RNA virus that is the leading cause of serious respiratory tract infections in infants and children, with the primary infection occurring in children from 6 weeks to 2 years of age and uncommonly in the first 4 weeks of life during nosocomial epidemics (Hall et al., 1979, New Engl. J. Med. 300:393-396). (Feigen et al, eds., 1987, In: Textbook of Pediatric Infectious Diseases, W B Saunders, Philadelphia at pages 1653-1675; New Vaccine Development, Establishing Priorities, Vol. 1, 1985, National Academy Press, Washington D.C. at pages 397-409; Ruuskanen et al., 1993, Curr. Probl. Pediatr. 23:50-79; Hall et al., 1979, New Engl. J. Med. 300:393-396). Certain populations of children are at risk for developing an RSV infection and these include preterm infants (Hall et al., 1979, New Engl. J. Med. 300:393-396), children with congenital malformations of the airway, children with bronchopulmonary dysplasia (Groothuis et al., 1988, Pediatrics 82:199-203), children with congenital heart disease (MacDonald et al., New Engl. J. Med. 307:397-400), and children with congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830).

RSV can infect the adult population as well. In this population, RSV causes primarily an upper respiratory tract disease, although elderly patients may be at greater risk for a serious infection and pneumonia (Evans, A. S., eds., 1989, Viral Infections of Humans. Epidemiology and Control, $3^{rd}$ ed., Plenum Medical Book, New York at pages 525-544), as well as adults who are immunosuppressed, particularly bone marrow transplant patients (Hertz et al., 1989, Medicine 68:269-281). Other at risk patients include those suffering from congestive heart failure and those suffering from chronic obstructive pulmonary disease (ie. COPD). There have also been reports of epidemics among nursing home patients and institutionalized young adults (Falsey, A. R., 1991, Infect. Control Hosp. Epidemiol. 12:602-608; and Garvie et al., 1980, Br. Med. J. 281:1253-1254).

While treatment options for established RSV disease are limited, more severe forms of the disease of the lower respiratory tract often require considerable supportive care, including administration of humidified oxygen and respiratory assistance (Fields et al., eds, 1990, Fields Virology, $2^{nd}$ ed., Vol. 1, Raven Press, New York at pages 1045-1072).

Ribavirin, which is the only drug approved for treatment of infection, has been shown to be effective in the treatment of pneumonia and bronchiolitis associated with RSV infection, and has been shown to modify the course of severe RSV disease in immunocompetent children (Smith et al., 1991, New Engl. J. Med. 325:24-29). However, the use of ribavirin is limited due to concerns surrounding its potential risk to pregnant women who may be exposed to the aerosolized drug while it is being administered in a hospital environment. Its use is also limited due to its relatively high cost.

Other peptide inhibitors of RSV infection have been identified, which inhibit viral growth in vitro, but have failed when tested in vivo, most likely due to lack of oral availability and a relatively low half life in circulation (Lambert, D. M., et al. (1996), PNAS (USA) 93:2186-2191; Magro, M. et al., (2010), J. Virol. 84:7970-7982; Park, M. et al. (2011), Anal. Biochem. 409:195-201).

Other small molecule inhibitors of RSV infection have also been identified, but have been discontinued for various reasons, some of which may be due to toxic side effects (Wyde, P. R. et al. (1998), Antiviral Res. 38:31-42; Nikitenko, A. A. et al. (2001), Bioorg Med Chem Lett 11:1041-1044; Douglas, J. L., et al. (2003), J. Virol 77:5054-5064; Bonfanti, J. F. et al, (2008), J. Med Chem 51:875-896).

Similarly, while a vaccine may be useful, no commercially available vaccine has been developed to date. Several vaccine candidates have been abandoned and others are under development (Murphy et al., 1994, Virus Res. 32:13-36). The development of a vaccine has proven to be problematic. In particular, immunization would be required in the immediate neonatal period since the peak incidence of lower respiratory tract disease occurs at 2-5 months of age. However, it is known that the neonatal immune response is immature at that time. Plus, the infant at that point in time still has high titers of maternally acquired RSV antibody, which might reduce vaccine immunogenicity (Murphy et al., 1988, J. Virol. 62:3907-3910; and Murphy et al., 1991, Vaccine 9:185-189).

Currently, passive immunization appears to be the only approved approach to prophylaxis of RSV disease. Initial evidence that suggested a protective role for IgG was obtained from studies demonstrating maternal antibody in ferrets (Prince, G. A., Ph.D. diss., University of California, Los Angeles, 1975) and humans (Lambrecht et al, 1976, J. Infect. Dis. 134:211-217; and Glezen et al., 1981, J. Pediatr. 98:708-715).

Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis. This same group of investigators then examined the ability of hyperimmune serum or immune globulin, enriched for RSV neutralizing antibody, to protect cotton rats and primates against RSV infection (Prince et al., 1985, Virus Res. 3:193-206; Prince et al., 1990, J. Virol. 64:3091-3092; Hemming et al., 1985, J. Infect. Dis. 152: 1083-1087; Prince et al., 1983, Infect. Immun. 42:81-87; and Prince et al., 1985, J. Virol. 55:517-520). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model.

More recent studies have concentrated on the role of two glycoproteins, designated F and G, which are found on the surface of RSV, as targets of neutralizing antibodies, due to the role of these glycoproteins in viral attachment and fusion with the host cell (Fields et al., 1990, supra; and Murphy et al., 1994, supra). The G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein may directly neutralize virus, or block fusion of the virus with the cell, or prevent cell to cell spread by preventing syncytia formation.

The first humanized antibody approved for use in pediatric patients for prevention of serious lower respiratory tract disease caused by RSV was palivizumab (SYNAGIS®), which immunospecifically binds to the F protein and is administered intramuscularly at recommended monthly doses of 15 mg/kg of body weight throughout the RSV season (November through April in the northern hemisphere). SYNAGIS® is composed of 95% human and 5% murine antibody sequences. See, Johnson et al, 1997, J. Infect. Diseases 176:1215-1224 and U.S. Pat. No. 5,824,307, the entire contents of which are incorporated herein by reference.

While SYNAGIS® has been successfully used for the prevention of RSV infection in pediatric patients, the need for multiple visits to the doctor's office for multiple intramuscular doses of 15 mg/kg of SYNAGIS® was not only inconvenient for the patient but could also result in missed doses. Thus, there was a need for development of antibodies that retained the immunospecificity for the RSV antigen, but which were more potent, with an improved pharmacokinetic profile, and thus have an overall improved therapeutic profile. Such an antibody is described in U.S Patent Publication 2003/0091584 and is known as motavizumab (NUMAX™). Although NUMAX™ has improved binding characteristics that may overcome the higher dosing requirements described above for SYNAGIS®, it also had a 3 to 5 fold increase in the frequency and severity of hypersensitivity reactions compared to SYNAGIS®. NUMAX™ was then withdrawn from future development.

Accordingly, there is still a need for effective therapies against RSV infections, and in particular, there is a need to identify a more potent antibody for preventing and treating RSV infections, but without the adverse side effects associated with those described above. The antibodies described herein, while exhibiting a lower binding affinity for RSV-F (i.e. the antibodies of the present invention do not bind as tightly to RSV-F as palivizumab) than that described for palivizumab or motavizumab appears to exhibit better neutralization capabilities and addresses those needs.

In certain embodiments, the antibodies of the invention are obtained from mice immunized with a primary immunogen, such as a whole RSV particle, either live, attenuated, or inactivated, or with a recombinant form of the virus, or with a purified F protein (See GenBank accession number AAX23994.1 (SEQ ID NO: 354)), or a recombinantly produced F protein (See SEQ ID NO: 353), followed by immunization with a secondary immunogen (whole virus, or purified F protein), or with an immunogenically active fragment of the F protein.

The immunogen may be DNA encoding the F protein or an active fragment thereof.

The immunogen may be derived from the N-terminal or C-terminal domain of either the 67 KDa precursor (F0), or from either of the two fragments generated from the precursor by a furin-like protease yielding two disulfide linked polypeptides, designated as F2 and F1, from the N and C terminal, respectively. The fragment may be derived from any of the known regions of RSV-F protein (See Sun, Z. et al. (2013), Viruses 5:211-225).

The full-length amino acid sequence of RSV-F is shown as SEQ ID NO: 354 and is also shown in GenBank accession number AAX23994.1.

A genetic construct containing the F protein of RSV is shown as SEQ ID NO: 353.

In certain embodiments, antibodies that bind specifically to RSV-F may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of RSV-F specific antibodies. In certain embodiments, any one or more of the above-noted regions of RSV-F, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to RSV-F. An antibody fragment may include a Fab fragment, a F(ab')2 fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (Vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$, and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to RSV-F.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to RSV-F are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In certain embodiments, the antibodies of the instant invention possess affinities ($K_D$) ranging from about $1.0 \times 10^{-7}$ M to about $1.0 \times 10^{-12}$M, when measured by binding to antigen either immobilized on solid phase or in solution phase. In certain embodiments, the antibodies of the invention possess affinities ($K_D$) ranging from about $1 \times 10^{-7}$ M to about $6 \times 10^{-10}$M, when measured by binding to antigen either immobilized on solid phase or in solution phase. In certain embodiments, the antibodies of the invention possess affinities ($K_D$) ranging from about $1 \times 10^{-7}$ M to about $9 \times 10^{-10}$M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region. Surprisingly, certain antibodies of the present invention, while demonstrating lower affinities than motavizumab, are more potent in terms of virus neutralization.

Bioequivalents

The anti-RSV-F antibodies and antibody fragments of the present invention encompass proteins having amino acid sequences that vary from those of the described antibodies, but that retain the ability to bind RSV-F. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological Characteristics of the Antibodies

In general, the antibodies of the present invention may function by binding to RSV-F and in so doing act to block the fusion of the viral membrane with the host cell membrane. The antibodies of the present invention may also function by binding to RSV-F and in so doing block the cell to cell spread of the virus and block syncytia formation associated with RSV infection of cells.

In certain embodiments, the antibodies of the present invention may function by blocking or inhibiting RSV fusion to the cell membrane by binding to any other region or fragment of the full length native F protein, the amino acid sequence of which is shown in SEQ ID NO: 354, also shown as GenBank accession number AAX23994.1. The antibodies may also bind to any region which is found in SEQ ID NO: 353, or to a fragment found within SEQ ID NO: 353.

In one embodiment, the invention provides a fully human monoclonal antibody or antigen-binding fragment thereof that binds to the F protein of RSV subtype A or B, wherein the antibody or fragment thereof exhibits one or more of the following characteristics: (a) is a fully human monoclonal antibody; (b) exhibits a $K_D$ ranging from about $1 \times 10^{-7}$ M to about $6 \times 10^{-10}$M; (c) is capable of neutralizing respiratory syncytial virus subtype A and subtype B strains in vitro; (d) demonstrates the ability to significantly reduce the viral load in an animal model of RSV infection (e) demonstrates a 1-2 logs greater reduction of nasal and/or lung viral titers when compared to palivizumab; (f) demonstrates an effective dose 99 ($ED_{99}$) of about 0.15 mg/kg or less when administered subcutaneously in a mouse model of RSV subtype A infection, or an $ED_{99}$ of about 0.62 mg/kg or less when administered in a cotton rat model of RSV subtype A infection, or an $ED_{99}$ of about 2.5 mg/kg or less when administered in a cotton rat model of RSV subtype B infection; (g) demonstrates an $ED_{99}$ that is about 2 to 3 fold lower than the $ED_{99}$ for palivizumab or motavizumab; (h) demonstrates a neutralization potency against one or more subtype A laboratory strains of RSV that is about 15 to 17 fold improvement over palivizumab, or demonstrates a neutralization potency against one or more subtype A clinical strains of RSV that is about 10 to 22 fold improvement over palivizumab; (i) demonstrates a neutralization potency against a subtype B laboratory strain of RSV that is about a 2 to 5 fold improvement over palivizumab (j) demonstrates a neutralization potency against a subtype A laboratory strain or clinical strain of RSV that is about a 0.5 to 2 fold improvement over AM-22; (k) demonstrates a neutralization potency against one or more subtype B laboratory strains of RSV that is about a 2.5 to 17 fold improvement over AM-22; (l) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322 and 338, or a substantially similar sequence thereof having at least 90%, at least 95%, at least 98% or at least 99% sequence identity; (m) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330 and 346, or a substantially similar sequence thereof having at least 90%, at least 95%, at least 98% or at least 99% sequence identity; (n) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, and 344, or a substantially similar sequence thereof having at least 90%, at least 95%, at least 98% or at least 99% sequence identity and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336 and 352, or a substantially similar sequence thereof having at least 90%, at least 95%, at least 98% or at least 99% sequence identity; (o) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324 and 340, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326 and 342, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332 and 348, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334 and 350, or a substantially similar sequence thereof having at least 90%, at least 95%, at least 98% or at least 99% sequence identity; (p) interacts with an amino acid sequence comprising residues ranging from about position 161 to about position 188 of SEQ ID NO: 354; (q) interacts with either the serine at position 173 of SEQ ID NO: 354, or the threonine at position 174 of SEQ ID NO: 354, or both the serine at position 173 of SEQ ID NO: 354 and the threonine at position 174 of SEQ ID NO: 354; (r) does not cross-compete for binding to RSV-F protein with palivizumab or motavizumab; (s) inhibits fusion of the virus to the cell.

Certain anti-RSV-F antibodies of the present invention are able to bind to the F protein of RSV and neutralize the infectivity of both subtypes A and B of RSV as determined by in vitro assays. The ability of the antibodies of the invention to bind to and neutralize the infectivity of the subtypes of RSV may be measured using any standard method known to those skilled in the art, including binding assays, or neutralization assays, or in vivo protection assays, as described herein.

Non-limiting, exemplary in vitro and in vivo assays for measuring binding activity and in vitro neutralization and in vivo efficacy are illustrated in Examples 3, 4, 5, 7, 8, 9, 10, 11 and 12 herein. In Example 3, the binding affinities and kinetic constants of human anti-RSV-F antibodies were determined by surface plasmon resonance and the measurements were conducted on a Biacore 4000 or T200 instrument. In Example 4, the potency of the antibodies was tested in a RSV micro-neutralization assay. Example 5 demonstrates the ability of the antibodies of the invention to neutralize an RSV infection in vivo in two different animal models. Examples 7 and 8 demonstrate the interaction of the antibodies of the invention with particular binding sites on RSV-F protein. Examples 9 and 10 demonstrate the neutralization capabilities of the antibodies with several laboratory and clinical strains of RSV subtypes A and B. Example 11 demonstrates the ability of the antibodies of the invention to inhibit fusion of the virus to cells. Example 12 demonstrates the cross-competition of various antibodies for binding to RSV-F.

Epitope Mapping and Related Technologies

Various techniques known to persons of ordinary skill in the art can be used to determine whether an antibody "interacts with one or more amino acids" within a polypeptide or protein. Exemplary techniques include, for example, a routine cross-blocking assay such as that described *Antibodies*, Harlow and Lane (Cold Spring Harbor Press, Cold Spring Harb., N.Y.) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) *Analytical Biochemistry* 267(2):252-259; Engen and Smith (2001) *Anal. Chem.* 73:256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the antibodies or antigen-binding fragments of the invention interact with an amino acid sequence comprising amino acid residues ranging from about position 161 to about position 188 of SEQ ID NO: 354. In certain embodiments, the antibodies of the invention may interact with amino acid residues that extend beyond the region identified above by about 5 to 10 amino acid residues, or by about 10 to 15 amino acid residues, or by about 15 to 20 amino acid residues towards either the amino terminal or the carboxy terminal of the RSV-F protein.

In one embodiment, the invention provides an isolated human monoclonal antibody that specifically binds RSV-F, or an antigen-binding fragment thereof, wherein the antibody or antigen-binding fragment thereof interacts with at least one amino acid sequence selected from the group consisting of SEQ ID NO: 355 and 356.

In one embodiment, the invention provides an isolated human monoclonal antibody that specifically binds RSV-F, or an antigen-binding fragment thereof, wherein the antibody or antigen-binding fragment thereof interacts with at least one amino acid residue within residues 161 through 188 of SEQ ID NO: 354.

In one embodiment, the invention provides an isolated human monoclonal antibody that specifically binds RSV-F, or an antigen-binding fragment thereof, wherein the antibody or antigen-binding fragment thereof interacts with at least one amino acid residue within SEQ ID NO: 355 or SEQ ID NO:356.

In one embodiment, the invention provides an isolated human monoclonal antibody that specifically binds RSV-F, or an antigen-binding fragment thereof, wherein the antibody or antigen-binding fragment thereof interacts with either the serine at position 173 of SEQ ID NO: 354, or the threonine at position 174 of SEQ ID NO: 354, or both the serine at position 173 of SEQ ID NO: 354 and the threonine at position 174 of SEQ ID NO: 354.

The present invention includes anti-RSV-F antibodies that bind to the same epitope as any of the specific exemplary antibodies described herein in Table 1. Likewise, the present invention also includes anti-RSV-F antibodies that compete for binding to RSV-F fragment with any of the specific exemplary antibodies described herein in Table 1.

In certain embodiments, the antibodies of the present invention do not cross-compete for binding to RSV-F with palivizumab, motavizumab, or AM-22.

In certain embodiments, the antibodies of the present invention do not bind to the same epitope on RSV-F protein as palivizumab or motavizumab.

In certain embodiments, the antibodies of the present invention do not bind to an epitope on RSV-F ranging from amino acid residue 255 to amino acid residue 276 of SEQ ID NO: 354.

One can easily determine whether an antibody binds to the same epitope as, or competes for binding with, a reference anti-RSV-F antibody by using routine methods known in the art. For example, to determine if a test antibody binds to the same epitope as a reference RSV-F antibody of the invention, the reference antibody is allowed to bind to a RSV-F protein or peptide under saturating conditions. Next, the ability of a test antibody to bind to the RSV-F molecule is assessed. If the test antibody is able to bind to RSV-F following saturation binding with the reference anti-RSV-F antibody, it can be concluded that the test antibody binds to a different epitope than the reference anti-RSV-F antibody. On the other hand, if the test antibody is not able to bind to the RSV-F molecule following saturation binding with the reference anti-RSV-F antibody, then the test antibody may bind to the same epitope as the epitope bound by the reference anti-RSV-F antibody of the invention.

To determine if an antibody competes for binding with a reference anti-RSV-F antibody, the above-described binding methodology is performed in two orientations: In a first orientation, the reference antibody is allowed to bind to a RSV-F molecule under saturating conditions followed by assessment of binding of the test antibody to the RSV-F molecule. In a second orientation, the test antibody is allowed to bind to a RSV-F molecule under saturating conditions followed by assessment of binding of the reference antibody to the RSV-F molecule. If, in both orientations, only the first (saturating) antibody is capable of binding to the RSV-F molecule, then it is concluded that the test antibody and the reference antibody compete for binding to RSV-F. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human RSV-F monoclonal antibody conjugated to a therapeutic moiety ("immunoconjugate"), such as an agent that is capable of reducing the severity of primary infection with RSV, or to ameliorate at least one symptom associated with RSV infection, including coughing, fever, pneumonia, or the severity thereof. Such an agent may be a second different antibody to RSV-F, or a vaccine. The type of therapeutic moiety that may be conjugated to the anti-RSV-F antibody and will take into account the condition to be treated and the desired therapeutic effect to be achieved. Alternatively, if the desired therapeutic effect is to treat the sequelae or symptoms associated with RSV infection, or any other condition resulting from such infection, such as, but not limited to, pneumonia, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al, 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity.

An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-RSV-F antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the invention may vary depending upon the age and the size of a subject to be administered, target disease, conditions, route of administration, and the like. When the antibodies of the present invention are used for treating a RSV infection in a patient, or for treating one or more symptoms associated with a RSV infection, such as the cough or pneumonia associated with a RSV infection in a patient, or for lessening the severity of the disease, it is advantageous to administer each of the antibodies of the present invention intravenously or subcutaneously normally at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the invention can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, nasal mucosa, rectal and intestinal mucosa, etc.) and may be administered together with other biologically active agents. Administration can be systemic or local. It may be delivered as an aerosolized formulation (See US2011/0311515 and US2012/0128669). The delivery of agents useful for treating respiratory diseases by inhalation is becoming more widely accepted (See A. J. Bitonti and J. A. Dumont, (2006), Adv. Drug Deliv. Rev, 58:1106-1118). In addition to being effective at treating local pulmonary disease, such a delivery mechanism may also be useful for systemic delivery of antibodies (See Maillet et al. (2008), Pharmaceutical Research, Vol. 25, No. 6, 2008).

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KW IKPEN™ (Eli Lilly), the SURECLICK™ Autoinjector (Amgen, Thousands Oaks, Calif.), the PENLET™ (Haselmeier, Stuttgart, Germany), the EPIPEN (Dey, L. P.) and the HUMIRA™ Pen (Abbott Labs, Abbott Park, Ill,), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

According to certain embodiments of the present invention, multiple doses of an antibody to RSV-F may be administered to a subject over a defined time course. The methods according to this aspect of the invention comprise sequentially administering to a subject multiple doses of an antibody to RSV-F. As used herein, "sequentially administering" means that each dose of antibody to RSV-F is administered to the subject at a different point in time, e.g., on different days separated by a predetermined interval (e.g., hours, days, weeks or months). The present invention includes methods which comprise sequentially administering to the patient a single initial dose of an antibody to RSV-F, followed by one or more secondary doses of the antibody to RSV-F and optionally followed by one or more tertiary doses of the antibody to RSV-F.

The terms "initial dose," "secondary doses," and "tertiary doses," refer to the temporal sequence of administration of the antibody to RSV-F. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to RSV-F, but generally may differ from one another in terms of frequency of administration. In certain embodiments, however, the amount of antibody to RSV-F contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antibody to RSV-F which is administered to a patient prior to the administration of the very next dose in the sequence with no intervening doses.

The methods according to this aspect of the invention may comprise administering to a patient any number of secondary and/or tertiary doses of an antibody to RSV-F. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Therapeutic Uses of the Antibodies

Due to their binding to/interaction with, the RSV fusion protein (RSV-F), the present antibodies are useful for preventing fusion of the virus with the host cell membrane, for preventing cell to cell virus spread, and for inhibition of syncytia formation. As such, the antibodies of the present invention are useful for preventing an infection of a subject with RSV when administered prophylactically. Alternatively, the antibodies of the present invention may be useful for ameliorating at least one symptom associated with the infection, such as coughing, fever, pneumonia, or for lessening the severity, duration, and/or frequency of the infection. The antibodies of the invention are also contemplated for prophylactic use in patients at risk for developing or acquiring an RSV infection. These patients include pre-term infants, full term infants born during RSV season (late fall to early spring), the elderly (for example, in anyone 65 years of age or older), or patients immunocompromised due to illness or treatment with immunosuppressive therapeutics, or patients who may have an underlying medical condition that predisposes them to an RSV infection (for example, cystic fibrosis patients, patients with congestive heart failure or other cardiac conditions, patients with airway impairment, patients with COPD). It is contemplated that the antibodies of the invention may be used alone, or in conjunction with a second agent, or third agent for treating RSV infection, or for alleviating at least one symptom or complication associated with the RSV infection, such as the fever, coughing, bronchiolitis, or pneumonia associated with, or resulting from such an infection. The second or third agents may be delivered concurrently with the antibodies of the invention, or they may be administered separately, either before or after the antibodies of the invention. The second or third agent may be an anti-viral such as ribavirin, an NSAID or other agents to reduce fever or pain, another second but different antibody that specifically binds RSV-F, an agent (e.g. an antibody) that binds to another RSV antigen, such as RSV-G, a vaccine against RSV, an siRNA specific for an RSV antigen.

In yet a further embodiment of the invention the present antibodies are used for the preparation of a pharmaceutical composition for treating patients suffering from a RSV infection. In yet another embodiment of the invention the present antibodies are used for the preparation of a pharmaceutical composition for reducing the severity of a primary infection with RSV, or for reducing the duration of the infection, or for reducing at least one symptom associated with the RSV infection. In a further embodiment of the invention the present antibodies are used as adjunct therapy with any other agent useful for treating an RSV infection, including an antiviral, a toxoid, a vaccine, a second RSV-F antibody, or any other antibody specific for an RSV antigen, including an RSV-G antibody, or any other palliative therapy known to those skilled in the art.

Combination Therapies

As noted above, the methods of the present invention, according to certain embodiments, comprise administering to the subject one or more additional therapeutic agents in combination with an antibody to RSV-F. As used herein, the expression "in combination with" means that the additional therapeutic agents are administered before, after, or concurrent with the pharmaceutical composition comprising the anti-RSV-F antibody. The term "in combination with" also includes sequential or concomitant administration of the anti-RSV-F antibody and a second therapeutic agent.

For example, when administered "before" the pharmaceutical composition comprising the anti-RSV-F antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-RSV-F antibody. When administered "after" the pharmaceutical composition comprising the anti-RSV-F antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-RSV-F antibodies. Administration "concurrent" or with the pharmaceutical composition comprising the anti-RSV-F antibody means that the additional therapeutic agent is administered to the subject in a separate dosage form within less than 5 minutes (before, after, or at the same time) of administration of the pharmaceutical composition comprising the anti-RSV-F antibody, or administered to the subject as a single combined dosage formulation comprising both the additional therapeutic agent and the anti-RSV-F antibody.

Combination therapies may include an anti-RSV-F antibody of the invention and any additional therapeutic agent that may be advantageously combined with an antibody of the invention, or with a biologically active fragment of an antibody of the invention.

For example, a second or third therapeutic agent may be employed to aid in reducing the viral load in the lungs, such as an antiviral, for example, ribavirin. The antibodies may also be used in conjunction with other therapies, as noted above, including a toxoid, a vaccine specific for RSV, a second antibody specific for RSV-F, or an antibody specific for another RSV antigen, such as RSV-G.

Diagnostic Uses of the Antibodies

The anti-RSV antibodies of the present invention may also be used to detect and/or measure RSV in a sample, e.g., for diagnostic purposes. It is envisioned that confirmation of an infection thought to be caused by RSV may be made by measuring the presence of the virus through use of any one or more of the antibodies of the invention. Exemplary diagnostic assays for RSV may comprise, e.g., contacting a sample, obtained from a patient, with an anti-RSV-F antibody of the invention, wherein the anti-RSV-F antibody is labeled with a detectable label or reporter molecule or used as a capture ligand to selectively isolate the virus containing the F protein from patient samples. Alternatively, an unlabeled anti-RSV-F antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure RSV containing the F protein in a sample include enzyme-linked immunosorbent assay (ELISA), radioimmunoassay (RIA), and fluorescence-activated cell sorting (FACS).

Samples that can be used in RSV diagnostic assays according to the present invention include any tissue or fluid sample obtainable from a patient, which contains detectable quantities of RSV-F protein, or fragments thereof, under normal or pathological conditions. Generally, levels of RSV-F in a particular sample obtained from a healthy patient (e.g., a patient not afflicted with a disease or condition associated with the presence of RSV-F) will be measured to initially establish a baseline, or standard, level of the F protein from RSV. This baseline level of RSV-F can then be compared against the levels of RSV-F measured in samples obtained from individuals suspected of having an RSV infection, or symptoms associated with such infection.

Vaccines and Immunogenic Compositions

One aspect of the invention provides an immunogenic composition, or a vaccine, that when administered to an individual, preferably a human, induces an immune response in such individual to a Respiratory Syncytial Virus (RSV) antigen, for example, a RSV-F polypeptide, wherein the composition may comprise a recombinant RSV-F protein, or a polypeptide fragment of a RSV-F protein, or an epitope contained within and obtained from an antigen of the RSV-F polypeptide or a fragment thereof, and/or comprises DNA and/or RNA which encodes and expresses an epitope from an antigen of the RSV-F polypeptide, or other polypeptides of the invention. The immunogenic composition or vaccine may be used therapeutically or prophylactically and may be used to elicit antibody immunity and/or cellular immunity, such as cellular immunity arising from CTL or CD4+ T cells.

In one embodiment of the invention, the immunogenic composition, or vaccine, may comprise the RSV-F protein as shown in SEQ ID NO: 354. In one embodiment of the invention, the immunogenic composition, or vaccine, may comprise a RSV-F polypeptide fragment comprising residues 161 through 188 of SEQ ID NO: 354. In one embodiment of the invention, the immunogenic composition, or vaccine, may comprise one or more amino acid residues contained within SEQ ID NO: 355 and/or SEQ ID NO: 356.

In one embodiment of the invention, the immunogenic composition, or vaccine, may comprise SEQ ID NO: 355 and/or SEQ ID NO: 356.

In a related aspect, the invention provides a method for inducing an immune response in an individual, particularly a mammal, preferably humans, by administering to an individual an immunogenic composition, or a vaccine, comprising a RSV-F protein, or an immunogenic fragment thereof, or a RSV-F antigen or an immunogenic fragment thereof comprising one or more epitopes contained within the RSV-F antigen or fragment thereof, adequate to produce an antibody and/or a T cell immune response to protect the individual from infection, particularly infection with Respiratory Syncytial Virus (RSV). Also provided are methods of using the immunogenic compositions, or vaccines of the invention for inducing an immune response that results in inhibiting, or slowing the progression of cell to cell viral spread. Methods are also provided for ameliorating at least one symptom associated with RSV infection by administering an immunogenic composition, or a vaccine, comprising at least one RSV-F antigen, or one or more epitopes contained within the RSV-F antigen, which when administered will induce an immune response in the individual.

For example, in one embodiment the invention provides a method of inducing an immune response in an individual comprising delivering to the individual an immunogenic composition, or vaccine comprising, an RSV-F antigen (e.g. the amino acid sequence shown in SEQ ID NO: 354), or an antigenic fragment thereof, (e.g. a polypeptide comprising residues 161 through 188 of SEQ ID NO: 354), or a nucleic acid vector comprising a nucleotide sequence to direct expression of such viral polypeptide, or a fragment or a variant thereof, in vivo in order to induce an immune response.

In one embodiment of the invention, the polypeptide to be used in an immunogenic composition or in a vaccine for inducing an immune response in an individual comprises residues 161 through 188 of SEQ ID NO: 354. In one embodiment of the invention, the polypeptide to be used in an immunogenic composition or in a vaccine for inducing an immune response in an individual comprises one or more amino acid residues contained within SEQ ID NO: 355 and/or SEQ ID NO: 356. In one embodiment of the invention, the polypeptide to be used in an immunogenic composition or in a vaccine for inducing an immune response in an individual comprises SEQ ID NO: 355 and/or SEQ ID NO: 356. In one embodiment of the invention, the immunogenic composition, or vaccine, may elicit an antibody response specific for the RSV-F antigen of RSV, wherein the antibodies generated interact with either the serine at position 173 of SEQ ID NO: 354, or the threonine at position 354, or both the serine at position 173 of SEQ ID NO: 354 and the threonine at position 174 of SEQ ID NO: 354.

In certain embodiments, it is advantageous for the RSV-F antigens or fragments thereof to be formulated into immunogenic compositions, or vaccines that comprise immunogenic, preferably immunologically effective, amounts of additional antigens to elicit immunity to other pathogens, preferably viruses and/or bacteria. Such additional antigens may include an influenza virus antigen, an antigen from metapneumovirus or from a coronavirus, an antigen from *Haemophilus influenzae, Streptococcus pneumonia*, or *Bordetella pertussis*. Other RSV antigens may be included in the immunogenic compositions, or vaccines, such as the RSV-G glycoprotein, or immunogenic fragments thereof, the HN protein, or derivatives thereof. In certain embodiments, influenza virus antigens to be included in the immunogenic compositions or vaccines of the invention may include whole, live or inactivated virus, split influenza virus, grown in eggs or MDCK cells, or Vero cells or whole flu virosomes, or purified or recombinant proteins thereof, such as HA, NP, NA, or M proteins, or combinations thereof.

In certain embodiments of the invention, the immunogenic composition, or vaccine formulation may comprise an immunogenic recombinant polypeptide and/or polynucleotide of the invention, or a combination thereof, together with a suitable carrier/excipient, such as a pharmaceutically acceptable carrier/excipient. The immunogenic composition and/or vaccine is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The immunogenic composition, or vaccine formulation of the invention may also include adjuvants for enhancing the immunogenicity of the formulation. At this time, the only adjuvant widely used in humans has been alum (aluminum phosphate or aluminum hydroxide) and calcium phosphate gels. Freund's complete adjuvant and other adjuvants used in research and veterinary applications have toxicities, which limit their potential use in human vaccines. However, chemically defined preparations such as oil emulsions and surfactant based formulations, e.g., MF59 (microfluidized detergent stabilized oil-in-water emulsion), QS21 (purified saponin), AS02 [SBAS2] (oil-in-water emulsion +MPL+ QS-21), Montanide ISA-51 and ISA-720 (stabilized water-in-oil emulsion), are also in development. Furthermore, microbial derivatives (natural and synthetic), e.g., muramyl dipeptide, monophosphoryl lipid A (e.g. 3 De-O-acylated monophosphoryl lipid A, also known as 3D-MPL, which is manufactured by Ribi lmmunochem, Montana), Detox (MPL+M. Phleicell wall skeleton), AGP [RC-529] (synthetic acylated monosaccharide), DCChol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), and QS21, an Hplc purified non-toxic fraction derived from the bark of Quillaja Saponaria Molina, have all been in development for human use.

A preferred form of 3 De-O-acylated monophosphoryl lipid A is disclosed in European Patent 0 689 454 B1 (SmithKline Beecham Biologicals SA).

Other particulate adjuvants include, e.g., virosomes (unilamellar liposomal vehicles incorporating a viral antigen), AS04 ([SBAS4] Al salt with MPL), ISCOMS (structured complex of saponins and lipids), polylactide co-glycolide (PLG).

Other suitable adjuvants include all acceptable immunostimulatory compounds, such as cytokines, chemokines, or colony stimulating factors. For example, these may include the interleukins IL-1, IL-2, IL-4, IL-7, IL-12, gamma-interferon, and hGM-CSF.

It is to be understood that the adjuvant and/or immunostimulatory compound to be used will depend on the subject to which the vaccine or immunogenic composition will be administered, the route of injection and the number of injections to be given.

While the invention has been described with reference to certain RSV-F polypeptides, it is to be understood that this covers fragments of the naturally occurring polypeptides, and similar polypeptides with additions, deletions or substitutions which do not substantially affect the immunogenic properties of the recombinant polypeptides or polynucleotides.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to RSV-F Protein

An immunogen comprising any one of the following can be used to generate antibodies to RSV-F protein. In certain embodiments, the antibodies of the invention are obtained from mice immunized with a primary immunogen, such as a whole respiratory syncytial virus isolate, either live, attenuated or killed/inactivated. The mice may be given one or more booster shots containing either the same virus isolate, or they may be boosted with the RSV-F protein itself. In certain embodiments, the mice are injected with live virus, followed by boosting with the construct shown as SEQ ID NO: 353, or with isolated RSV-F protein, obtained from a virus isolate or prepared recombinantly. (See also GenBank accession number AAX23994.1)

In certain embodiments, the antibodies of the invention are obtained from mice immunized with a primary immunogen, such as a biologically active RSV, subtype A or B, and/or the RSV fusion (F) protein, or an immunogenic fragment of the RSV fusion (RSV-F) protein, or DNA encoding the full length protein or the active fragment thereof. The immunogen may be delivered to the animal via any route including but not limited to intramuscularly, subcutaneously, intravenously or intranasally.

In certain embodiments, whole virus, or the RSV-F protein or fragments thereof may be used for preparing monospecific, bispecific, or multispecific antibodies.

The whole virus, or full length proteins, or fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a RSV-F immunoassay. When a desired immune response was achieved, splenocytes were harvested and fused with mouse myeloma cells to preserve their viability and form hybridoma cell lines. The hybridoma cell lines were screened and selected to identify cell lines that produce RSV-F-specific antibodies. Using this technique, and the various immunogens described above, several chimeric antibodies (i.e., antibodies possessing human variable domains and mouse constant domains) were obtained; certain exemplary antibodies generated in this manner were designated as H1M3621N, H1M3622N, H1M2634N and H1M3627N.

Anti-RSV-F antibodies were also isolated directly from antigen-positive B cells without fusion to myeloma cells, as described in U.S. 2007/0280945A1, herein specifically incorporated by reference in its entirety. Using this method, several fully human anti-RSV-F antibodies (i.e., antibodies possessing human variable domains and human constant domains) were obtained; exemplary antibodies generated in this manner were designated as follows: H1H3564P, H1H3565P, H1H3566P, H1H3567P, H1H3581P, H1H3583P, H1H3589P, H1H3591P, H1H3592P, H1H3597P, H1H3598P, H1H3603P, H1H3604P, H1H3605P, H1H3607P, H1H3608P2, H1H3592P2 and H1H3592P3.

The biological properties of the exemplary antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected antibodies specific for RSV-F protein and their corresponding antibody identifiers. Antibodies are typically referred to herein according to the following nomenclature: Fc prefix (e.g. "H4H", "H1M", "H2M"), followed by a numerical identifier (e.g. "3117" as shown in Table 1), followed by a "P" or "N" suffix. Thus, according to this nomenclature, an antibody may be referred to as, e.g. "H1H3117". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

Antibody Comparators

Anti-RSV-F antibody controls were included in the following Examples for comparative purposes. Isotype matched negative controls were also used in the Examples. One anti-RSV-F control antibody is designated herein as Control I and is a humanized anti-RSV-F antibody with heavy and light chain variable domain sequences of the palivizumab (SYNAGIS®) humanized antibody as set forth in U.S. Pat. No. 7,635,568 and U.S. Pat. No. 5,824,307. The variable light and heavy chains were expressed with human kappa and gamma-1 constants, respectively. One anti-RSV-F antibody is designated herein as Control II and is a humanized anti-RSV-F antibody variant of palivizumab, with heavy and light chain variable domain sequences of the motavizumab (NUMAX™) humanized antibody described in US2003/0091584 and by Wu et al, (2007), J. Mol. Biol. 368:652-665. The variable light and heavy chains were expressed with human kappa and gamma-1 constants, respectively. Another anti-RSV-F antibody is designated as Control III (also referred to as AM-22) and is described in U.S. Pat. No. 8,568,726. The amino acid sequence of the heavy and light chain of AM-22 is shown in SEQ ID NO: 357 (for the heavy chain of the antibody) and SEQ ID NO: 358 (for the light chain of the antibody).

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H3564P | 2 | 4 | 6 | 8 | 10 | 12 | 14 | 16 |
| H1H3565P | 18 | 20 | 22 | 24 | 26 | 28 | 30 | 32 |
| H1H3566P | 34 | 36 | 38 | 40 | 42 | 44 | 46 | 48 |
| H1H3567P | 50 | 52 | 54 | 56 | 58 | 60 | 62 | 64 |
| H1H3581P | 66 | 68 | 70 | 72 | 74 | 76 | 78 | 80 |
| H1H3583P | 82 | 84 | 86 | 88 | 90 | 92 | 94 | 96 |
| H1H3589P | 98 | 100 | 102 | 104 | 106 | 108 | 110 | 112 |
| H1H3591P | 114 | 116 | 118 | 120 | 122 | 124 | 126 | 128 |
| H1H3592P | 130 | 132 | 134 | 136 | 138 | 140 | 142 | 144 |
| H1H3597P | 146 | 148 | 150 | 152 | 154 | 156 | 158 | 160 |
| H1H3598P | 162 | 164 | 166 | 168 | 170 | 172 | 174 | 176 |
| H1H3603P | 178 | 180 | 182 | 184 | 186 | 188 | 190 | 192 |
| H1H3604P | 194 | 196 | 198 | 200 | 202 | 204 | 206 | 208 |
| H1H3605P | 210 | 212 | 214 | 216 | 218 | 220 | 222 | 224 |
| H1H3607P | 226 | 228 | 230 | 232 | 234 | 236 | 238 | 240 |
| H1H3608P2 | 242 | 244 | 246 | 248 | 250 | 252 | 254 | 256 |
| H1H3592P2 | 258 | 260 | 262 | 264 | 266 | 268 | 270 | 272 |
| H1H3592P3 | 274 | 276 | 278 | 280 | 282 | 284 | 286 | 288 |
| H1M3621N | 290 | 292 | 294 | 296 | 298 | 300 | 302 | 304 |
| H1M3622N | 306 | 308 | 310 | 312 | 314 | 316 | 318 | 320 |
| H1M2634N | 322 | 324 | 326 | 328 | 330 | 332 | 334 | 336 |
| H1M3627N | 338 | 340 | 342 | 344 | 346 | 348 | 350 | 352 |

Example 3

Antibody Binding Affinities and Kinetic Constants of Human Monoclonal Anti-RSV-F Antibodies as Determined by Surface Plasmon Resonance Binding affinities and kinetic constants of human monoclonal anti-RSV-F antibodies were determined by surface plasmon resonance at 25° C. (Tables 2-3). Measurements were conducted on a Biacore 4000 or T-200 instrument. Antibodies, expressed with either mouse Fc (AbPID prefix H1 M; H2M) or human IgG1 Fc (AbPID prefix H1H), were captured onto an anti-mouse or anti-human Fc sensor surface (Mab capture format), and soluble monomeric (RSV-F.mmh; SEQ ID NO: 353) protein was injected over the surface. All Biacore binding studies were performed in HBST running buffer (0.01 M HEPES pH 7.4, 0.15 M NaCl, 3 mM EDTA, 0.005% v/v surfactant P20). Different concentrations of RSV-F.mmh prepared in HBST running buffer were injected over the anti-RSV-F monoclonal antibody captured surface at a flow rate of 30 μl/min (Biacore 4000) or at a flow rate of 50 μl/min (Biacore T-200) and the association of RSV-F.mmh to captured monoclonal antibody was monitored for 6 min or 3 min respectively. The dissociation of RSV-F.mmh from the monoclonal antibody in HBST running buffer was monitored for 8-10min at 25° C. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives (t½) were calculated from the kinetic rate constants as: $K_D$ (M)=$k_d/k_a$; and $t_{1/2}$ (min)=$(\ln 2/(60 * k_d))$.

Anti-RSV-F antibodies of the invention displayed a broad range of affinities for RSV-F.mmh. Control I, produced based on the public sequence of palivizumab set forth in U.S. Pat. No. 7,635,568, and Control II, produced on the public sequence of motavizumab as described in Wu et al, (2007), (J. Mol. Biol. 368:652-665) displayed the approximately ~70-fold difference (control 1; 38 nM vs control II; 0.43 nM) in affinity that has been previously reported.

TABLE 2

Biacore Binding Affinities of Hybridoma mAbs at 25° C.
Binding at 25° C./Mab Capture Format

| AbPID | $k_a$ (1/Ms) | $k_d$ (1/s) | $K_D$ (M) | t½ (min) |
|---|---|---|---|---|
| H1M3621N | 2.05E+05 | 2.08E−04 | 1.01E−09 | 56 |
| H1M3622N | 3.84E+04 | 9.13E−05 | 2.38E−09 | 127 |
| H1M3624N | 1.79E+05 | 1.83E−04 | 1.02E−09 | 63 |
| H1M3627N | 2.59E+05 | 5.23E−04 | 2.02E−09 | 22 |

TABLE 3

Biacore binding affinities of human Fc mAbs at 25° C.
Binding at 25° C./Mab Capture Format

| AbPID | $k_a$ (1/Ms) | $k_d$ (1/s) | $K_D$ (M) | t½ (min) |
|---|---|---|---|---|
| H1H3564P | 3.10E+03 | 7.78E−05 | 2.50E−08 | 148 |
| H1H3565P | 1.93E+04 | 5.80E−05 | 3.01E−09 | 199 |
| H1H3566P | 2.04E+04 | 4.20E−05 | 2.06E−09 | 275 |
| H1H3567P | 6.05E+04 | 2.63E−03 | 4.34E−08 | 4 |
| H1H3581P | NB | NB | NB | NB |
| H1H3583P | 8.94E+04 | 3.08E−03 | 3.44E−08 | 4 |
| H1H3589P | 3.77E+04 | 9.14E−03 | 2.43E−07 | 1 |
| H1H3591P | 4.46E+04 | 1.53E−03 | 3.42E−08 | 8 |
| H1H3592P | 1.06E+05 | 4.66E−04 | 4.39E−09 | 25 |
| H1H3592P2 | 9.93E+04 | 1.46E−03 | 1.47E−08 | 8 |
| H1H3592P3 | 8.86E+04 | 7.47E−04 | 8.43E−09 | 15 |
| H1H3597P | NB | NB | NB | NB |
| H1H3598P | NB | NB | NB | NB |
| H1H3603P | 3.00E+03 | 1.23E−04 | 4.10E−08 | 94 |
| H1H3604P | 3.10E+03 | 9.27E−05 | 3.00E−08 | 125 |
| H1H3605P | 2.80E+03 | 1.68E−04 | 5.90E−08 | 69 |
| H1H3607P | 4.20E+03 | 1.48E−04 | 3.50E−08 | 78 |
| H1H3608P2 | 4.85E+03 | 2.60E−05 | 5.35E−09 | 445 |
| H1H3627N | 2.56E+05 | 1.49E−04 | 5.81E−10 | 78 |
| Control I | 6.75E+04 | 2.57E−03 | 3.81E−08 | 4 |
| Control II | 1.89E+05 | 8.13E−05 | 4.29E−10 | 142 |

NB: No binding observed under the conditions of the experiment

Example 4

Respiratory Syncytial Virus Fusion (RSV-F) Protein Antibodies Display Potent Neutralization Capabilities Across RSV Subtype A and Subtype B Strains Purified antibodies were tested in a RSV micro-neutralization assay to determine potency. Briefly, $10^4$ HEp-2 cells cultured in MEM high glucose medium, supplemented with 5% Hyclone FBS, L-glutamine and antibiotics, were seeded into 96-well clear bottom-black microplates and incubated for 16-18 hours (37° C., 5% $CO_2$). Next, various concentrations of antibodies, starting at 666 nM with subsequent 1:5 dilutions in media, were incubated with the RSV 1540 (A2) strain at an MOI of 0.04 for 2 hours (37C, 5% $CO_2$). Virus-free and irrelevant isotype controls were included.

Post incubation, the antibody:virus mixture was added to the HEp-2 cells and infection was maintained for 3 days. The degree of infection was determined by fixing cells in 2% PFA and performing an ELISA with Goat anti-RSV/anti-Goat HRP antibodies. Luminescence reagents were added to the wells and signal was detected using a plate reader (Victor X3, Perkin Elmer). Luminescence values were analyzed by a three-parameter logistic equation over an 11-point response curve (GraphPad Prism).

The antibodies of the invention displayed a broad range of neutralization activities against the RSV A2 (1540) strain (Table 4-5). Several antibodies displayed lower $IC_{50}$ values then control I while only a few exemplary antibodies H1H3627N, H1H3591P, H1H3592P and H1H3592P3 showed better neutralization then control II. Select antibodies (H1H3627N, H1H3592P3) were also tested for their ability to neutralization RSV subtype B strains (Table 6).

This example demonstrates the efficacy of the antibodies of this invention to neutralize several strains of RSV-F, across two subtypes, in vitro, with greater potency than previously demonstrated for established controls.

TABLE 4

Neutralization potency for selected mAbs against RSV A2 (1540)

| | IC$_{50}$ [pM] for RSV A2 Neutralization: | | | | | | |
|---|---|---|---|---|---|---|---|
| AbPID | Trial 1 | Trial 2 | Trial 3 | Trial 4 | Trial 5 | Trial 6 | Trial 7 |
| H1M3621N | 582 | 180 | — | — | — | — | — |
| H1M3622N | 320 | 82 | — | — | — | — | — |
| H1M3624N | 540 | 270 | 92 | — | — | — | — |
| H1M3627N | 4 | 4 | 5 | — | — | 10 | — |
| H1H3564P | >10000 | — | — | — | — | — | — |
| H1H3565P | >10000 | — | — | — | — | — | — |
| H1H3566P | >10000 | — | — | — | — | — | — |
| H1H3567P | — | — | — | 257 | — | 390 | — |
| H1H3581P | >10000 | — | — | — | — | — | — |
| H1H3583P | — | — | — | — | 50 | — | — |
| H1H3589P | — | — | — | — | 300 | — | — |
| H1H3591P | — | — | — | 6 | — | 8 | 6 |
| H1H3592P | — | — | — | 6 | — | 5 | 4 |
| H1H3592P3 | — | — | — | — | — | — | 10 |
| H1H3597P | >10000 | — | — | — | — | — | — |
| H1H3598P | >10000 | — | — | — | — | — | — |
| H1H3603P | >10000 | — | — | — | — | — | — |
| H1H3604P | >10000 | — | — | — | — | — | — |
| H1H3605P | >10000 | — | — | — | — | — | — |
| H1H3607P | >10000 | — | — | — | — | — | — |
| H1H3608P2 | >10000 | — | — | — | — | — | — |
| H1H3570P | >10000 | — | — | — | — | — | — |
| H1H3627N | — | — | — | — | — | — | 3 |
| Control 1 | 1820 | 950 | 290 | 530 | 160 | 500 | 250 |
| Control 2 | 50 | 30 | 23 | 20 | 12 | 12 | 12 |

TABLE 5

Neutralization potency for selected mAbs against RSV subtype A

| | Subtype A Neutralization: IC$_{50}$ & Fold Improvement Relative to Control 1 | | | |
|---|---|---|---|---|
| | RSV-A2 (1540) Neutral. IC50 | | RSV-Long Neutral. IC50 | |
| AbPID | [pM] | Fold | [pM] | Fold |
| H1H3627N | 2.6 | 138 | 7.3 | 73 |
| H1H3592P3 | 10 | 36 | 15 | 35 |
| Control I | 360 | — | 536 | — |
| Control II | 14 | 25 | 65 | 8.2 |

TABLE 6

Neutralization potency for selected mAbs against RSV subtype B

| | Subtype B Neutralization: IC$_{50}$ & Fold Improvement Relative to Control 1 | | | |
|---|---|---|---|---|
| | RSV - 1580 Neutral. IC50 | | RSV-9320 Neutral. IC50 | |
| AbPID | [pM] | Fold | [pM] | Fold |
| H1H3627N | 6.7 | 55 | 11 | 42 |
| H1H3592P3 | 31 | 12 | 100 | 4.6 |
| Control I | 375 | — | 460 | — |
| Control II | 43 | 8.7 | 56 | 8.2 |

Example 5

Selected Anti-RSV-F Antibodies Display Potent Neutralization of RSV Infection In Vivo A. Mouse Model The exemplary antibodies H1H3627N and H1H3592P3 were selected for in vivo RSV neutralization studies using Balb/c mice. Briefly, 7 week old Balb/c mice (n=4-5) were injected SC at two doses (0.15 or 0.05 mg/kg) using either H1H3627N, H1H3592P3, control I, control II or isotype-matched antibody. The use of carrier antibody (1 mg/kg) was utilized in all experiments to minimize the loss of anti-RSV-F antibody.

One day post-injection, mice were challenged intranasally with 50 ul (10$^6$ pfu) of RSV A2 (1540) strain. Four days post-infection, sera was drawn, mice were sacrificed, and lungs were extracted and homogenized in 1 mL of PBS using an OmniGLH homogenizer. Lung homogenates were centrifuged to remove cellular debris and a portion of supernatant was used to determine anti-RSV-F mAb concentration in the lung. The remaining supernatant was used to make serial dilutions which were incubated with HEp-2 cells for 2 hours, to allow viral entry. Subsequently, supernatant was removed and the cells were overlaid with 1% methylcellulose. Six days later, cells were stained with crystal violet and plaques were counted and the log$_{10}$ viral reduction was calculated relative to isotype control.

Exemplary antibodies H1H3627N and H1H3592P3 were more efficacious in reducing the viral load in vivo than control I or control II anti-RSV-F antibodies (Tables 7a-7e). Specifically, at the 0.15 mg/kg dose, antibodies H1H3627N, H1H3592P3 and control II all effectively reduced RSV infection in the lung to near undetectable levels compared to control I (viral reduction log(10) fold change ≥2.10). Total human IgG measurements in the lungs and serum confirmed that antibody levels were relatively consistent between groups.

At a lower administered dose, greater differentiation in neutralization efficacy between the three antibodies compared to control I was evident. At 0.05 mg/kg, H1H3592P3 showed the greatest reduction in viral load, with fold changes ranging from 1.49 to >2.07 logs, compared with viral load reduction fold changes of 1.08 to 1.36 logs for H1H3627N and 0.01 to 0.65 logs for control II. Control I at this lower dose was only moderately effective with viral load reduction changes of 0.03 to 1.03 logs.

The results indicate that both H1H3627N and H1H3592P3 are potent RSV neutralizing antibodies in vivo, with the latter showing a trend of being a more effective neutralizer of RSV infection at lower doses.

A dosing range experiment was performed following the same protocol described above, injecting SC 4 different doses of control I antibody (0.6, 0.3, 0.15 and 0.05 mg/kg), and two doses (0.15 and 0.05 mg/kg) of H1H3592P3 and control II. Viral reduction in the lungs was calculated as a percentage of isotype control (Exp M4, Tables 7d-e).

Exemplary antibody H1H3592P3 was more efficacious in reducing the viral load in vivo (in mouse) than control I or control II anti-RSV-F antibodies. In addition, the dose of control I required to reach a 99% viral reduction in the lungs was 3-4 fold higher than the dose of H1H3592P3.

Tables 7(a-e): RSV viral reduction (log (10)) in mice after administration of Anti-RSV-F antibodies TABLE 7a

| Exp M1 | | Dose: 0.15 mg/kg | | | Dose: 0.05 mg/kg | | |
|---|---|---|---|---|---|---|---|
| PID | Mice per group | Viral Reduction (log10) | mAb [ng/ml] Lungs | mAb [ng/ml] Serum | Viral Reduction (log10) | mAb [ng/ml] Lungs | mAb [ng/ml] Serum |
| H1H3627N | 5 | >2.10 | 35 ± 18 | 1041 ± 212 | 1.20 | 7 ± 4 | 274 ± 38 |
| H1H3592P3 | 5 | >2.10 | 44 ± 14 | 1731 ± 770 | >2.07 | 17 ± 4 | 438 ± 51 |
| Control I | 5 | 1.02 | 33 ± 11 | 895 ± 132 | 1.03 | 9 ± 5 | 365 ± 111 |
| Control II | 5 | >2.10 | 82 ± 24 | 1948 ± 429 | 0.65 | 7 ± 4 | 555 ± 80 |
| Isotype Ctrl | 5 | NA | 76 ± 28 | 2180 ± 197 | NA | 25 ± 2 | 1287 ± 120 |

TABLE 7b

| Exp M2 | | Dose: 0.15 mg/kg | | | Dose: 0.05 mg/kg | | |
|---|---|---|---|---|---|---|---|
| PID | Mice per group | Viral Reduction (log10) | mAb [ng/ml] Lungs | mAb [ng/ml] Serum | Viral Reduction (log10) | mAb [ng/ml] Lungs | mAb [ng/ml] Serum |
| H1H3627N | 5 | >2.51 | 23 ± 8 | 724 ± 148 | 1.08 | 3 ± 3 | 300 ± 35 |
| H1H3592P3 | 5 | >2.51 | 27 ± 5 | 1261 ± 74 | 1.49 | 10 ± 2 | 333 ± 55 |
| Control I | 5 | 0.79 | 9 ± 2 | 611 ± 61 | 0.15 | 1 ± 1 | 221 ± 35 |
| Control II | 5 | 2.31 | 13 ± 8 | 587 ± 36 | 0.01 | 1 ± 3 | 237 ± 22 |
| Isotype Ctrl | 5 | NA | 46 ± 12 | 1389 ± 170 | NA | 15 ± 4 | 498 ± 92 |

TABLE 7c

| Exp M3 | | Dose: 0.15 mg/kg | | | Dose: 0.05 mg/kg | | |
|---|---|---|---|---|---|---|---|
| PID | Mice per group | Viral Reduction (log10) | mAb [ng/ml] Lungs | mAb [ng/ml] Serum | Viral Reduction (log10) | mAb [ng/ml] Lungs | mAb [ng/ml] Serum |
| H1H3627N | 4 | 2.7 | 26 ± 6 | 1143 ± 83 | 1.36 | 7 ± 1 | 394 ± 16 |
| H1H3592P3 | 4 | >2.83 | 31 ± 12 | 947 ± 105 | 1.66 | 13 ± 4 | 371 ± 21 |
| Control I | 4 | 1.00 | 58 ± 14 | 1426 ± 114 | 0.03 | 6 ± 5 | 442 ± 27 |
| Control II | 4 | 2.35 | 20 ± 6 | 1152 ± 142 | 0.54 | BDL | 373 ± 21 |
| Isotype Ctrl | 4 | NA | 41 ± 3 | 808 ± 52 | NA | 37 ± 8 | 326 ± 26 |

TABLE 7d

| | Dose: 0.6 mg/kg | | Dose: 0.3 mg/kg | |
|---|---|---|---|---|
| Exp M4 (ED$_{99}$) | Viral | | Viral | |
| PID | Mice per group | Reduction (%) | mAb [ng/ml] Serum | Reduction (%) | mAb [ng/ml] Serum |
| Control I | 5 | >99 | 8451.9 ± 2562 | 96.9 | 3129.7 ± 403 |

ND: Not determined

TABLE 7e

| | Dose: 0.15 mg/kg | | Dose: 0.05 mg/kg | |
|---|---|---|---|---|
| Exp M4 (ED$_{90}$) | Viral | | Viral | |
| PID | Mice per group | Reduction (%) | mAb [ng/ml] Serum | Reduction (%) | mAb [ng/ml] Serum |
| H1H3592P3 | 5 | >99 | 1578.9 ± 256 | 90.6 | 524.0 ± 42 |
| Control I | 5 | 57.9 | 1561.2 ± 282 | 24.2 | 547.5 ± 59 |
| Control II | 5 | 96.7 | 1566.0 ± 354 | 48.5 | 465.7 ± 85 |
| Isotype Ctrl | 5 | NA | 1406.0 ± 196 | NA | 375.3 ± 86 |

ND: Not determined

B. Cotton Rat Model

The exemplary antibodies H1H3627N and H1H3592P3 were selected for in vivo RSV neutralization studies using cotton rats. Briefly, 6-8 week old cotton rats (n=5) were injected IM at two doses (5 or 0.6 mg/kg) using either H1H3627N, H1H3592P3, control I, control II or isotype-matched antibody.

One day post-injection, rats were challenged intranasally with 100 ul ($10^5$ pfu) of RSV A2 strain. Four days post-infection, sera was drawn, rats were sacrificed, and lung and nasal tissues were extracted for viral titration. Lung homogenates were centrifuged to remove cellular debris and a portion of supernatant was used to determine anti-RSV-F mAb concentration in the lung. The remaining supernatant was used to make serial dilutions, which were incubated with HEp-2 cells to allow viral entry. Subsequently, supernatant was removed and the cells were overlaid with 1% methylcellulose. Six days later, cells were stained and plaques were counted and the $\log_{10}$ viral reduction was calculated relative to isotype control.

Exemplary antibody H1H3592P3 was more efficacious in reducing the viral load in the lungs and nose than control I, and as efficacious as control II in lungs and better in the nose. Exemplary antibody H1H3627N was only better than control I and as efficacious as control II in the nose (Table 8). Specifically, at the 5 mg/kg dose, antibodies H1H3627N, H1H3592P3, control I and control II all effectively reduced RSV infection in the lung to near undetectable levels compared to isotype control (viral reduction log(10) fold change 2.33). However, in the nose, greater differentiation in neutralization efficacy between H1H3627N, H1H3592P3, control II compared to control I was evident. H1H3592P3 showed the greater reduction in viral load (2.65 logs) compared to H1H3627N (1.46 logs) or control II (1.33 logs).

At a lower administrated dose, greater differentiation in neutralization efficacy between the three antibodies compared to control I was evident in the lungs. At 0.6 mg/kg, H1H3592P3 showed similar reduction in viral load than control II (1.5 logs) and they were both more efficacious than control I (0.624 logs). H1H3627N showed less efficacy than the other three antibodies.

Exemplary anti-RSV-F antibody H1H3592P3 was next selected for testing its ability to neutralize RSV subtype B in H1H3592P3, compared with a reduction of 0.75 logs by Control I and 0.83 logs by Control II.

Overall, H1H3592P3 showed superiority in neutralization of RSV Subtype B in the lungs over both Control I and II at 0.6 mg/kg. At 5 mg/kg, H1H3592P3 showed comparable neutralizing ability than Control I and Control II in reducing viral load in the lungs.

The results indicate that H1H3592P3 is a potent neutralizer of RSV subtype strains A and B in vivo in cotton rats, being a more effective neutralizer of RSV infection at high doses in the nose and at lower doses in the lungs. The efficacy at low doses indicates the possibility of a lower dose regimen in the clinic.

TABLE 8

RSV-A viral reduction (log (10)) in cotton rats after administration of Anti-RSV-F antibodies

| | | Dose: 0.6 mg/kg | | | Dose: 5.0 mg/kg | | |
|---|---|---|---|---|---|---|---|
| Exp R1 | | Viral | Viral | mAb | Viral | Viral | mAb |
| PID | Rats per group | Reduction lung (log10) | Reduction nose (log10) | [ng/ml] Serum Day 4 | Reduction lung (log10) | Reduction nose (log10) | [ng/ml] Serum Day 4 |
| H1H3627N | 5 | 0.34 | 0.22 | 3.43 ± 0.25 | 2.33 | 1.46 | 21.52 ± 5.47 |
| H1H3592P3 | 5 | 1.66 | 0.19 | 3.49 ± 0.55 | 2.56 | 2.66 | 46.28 ± 7.69 |
| Control I | 5 | 0.62 | 0.21 | 3.04 ± 0.29 | 2.37 | 1.07 | 39.95 ± 5.23 |
| Control II | 5 | 1.50 | 0.20 | 4.26 ± 0.66 | 2.55 | 1.33 | 24.06 ± 2.96 |
| Isotype Ctrl | 4 | NA | NA | 3.78 ± 0.99 | NA | NA | 30.43 ± 6.66 |

TABLE 9

RSV-B viral reduction (log (10)) in cotton rats after administration of Anti-RSV-F antibodies

| | | Dose: 0.6 mg/kg | | | Dose: 5.0 mg/kg | | |
|---|---|---|---|---|---|---|---|
| Exp R2 | | Viral | Viral | mAb | Viral | Viral | mAb |
| PID | Rats per group | Reduction lung (log10) | Reduction nose (log10) | [ng/ml] Serum Day 4 | Reduction lung (log10) | Reduction nose (log10) | [ng/ml] Serum Day 4 |
| H1H3592P3 | 10 | 1.29 | 0.21 | 3.89 ± 0.99 | 2.21 | 0.86 | 42.31 ± 13.5 |
| Control I | 11 | 0.75 | 0.15 | 3.87 ± 0.73 | 2.11 | 0.79 | 35.28 ± 11.8 |
| Control II | 11 | 0.83 | 0.10 | 3.75 ± 0.49 | 2.18 | 1.24 | 27.65 ± 7.49 |
| Isotype Control | 10 | NA | NA | 3.56 ± 1.17 | NA | NA | 34.28 ± 9.24 | vivo using the cotton rat model. As with RSV/A, 6- to 8-week old cotton rats (n=4-6/group/experiment) were intramuscularly administered either 5 or 0.6 mg/kg of H1H3592P3, Control I or Control II. The next day, animals were challenged with 10^5 pfu of RSV/B strain 18537. Four days post-challenge, viral titers in the lungs and nose were determined along with serum antibody titers. The results shown in table 9 were data pooled from two independent experiments.

H1H3592P3 showed efficacy in reducing RSV/B viral load in lungs at both high and low doses (Table 9). At 5.0 mg/kg, RSV/B viral load in the lungs was reduced by 2.21 logs with H1H3592P3, compared with a reduction of 2.11 logs by Control I and 2.18 logs by Control II. At 0.6 mg/kg, RSV/B viral load in the lungs was reduced by 1.29 logs with C. Cotton Rat Model-Determination of the $ED_{99}$ of an Exemplary Antibody H1H3592P3

Dose-ranging studies using the cotton rat were performed to determine at which dose an exemplary antibody H1H3592P3 would reduce viral load by >99% (i.e. the $ED_{99}$). Cotton rats were prophylactically administered an IM dose of H1H3592P3 or Control 1 antibody at either 10, 5, 2.5, 1.25 or 0.62 mg/kg. Additionally an isotype control antibody was dosed in at either 10 or 0.62 mg/kg to bracket the active agents in this study. Following antibody treatments an intranasal RSV challenge of either subtype A (RSV A2 strain) or subtype B (RSV B strain 18537) was performed. Four days post-infection, sera was drawn, rats were sacrificed, and lung tissue was extracted for viral titration. H1H3592P3 at a dose of 0.62 mg/kg achieved >99% viral load reduction in the lungs as compared to Control 1 which required a dose of 2.5 mg/kg to reach the same >99% viral reduction (Table 10). The mean terminal Control 1 concentration (27 µg/mL) at the calculated $ED_{99}$ correlated well with previously published work (Scott and Lamb, 1999), which indicated that a serum palivizumab concentration (i.e. Control 1) of 30-40 µg/mL, at the time of RSV infection, was associated with a 99% reduction in lung viral load. The mean terminal H1H3592P3 concentration (4.9 µg/mL) correlated well with the 4-fold lower dose delivered at its $ED_{99}$. Results against subtype B challenge were similar (Table 11) in that an $ED_{99}$ for H1H3592P3 was achieved at 2.5 mg/kg while Control 1 required roughly a 4× greater dose (10 mg/kg) to obtain that same >99% viral lung reduction.

In summary these studies support that less frequent dosing of H1H3592P3 may confer the same level of protection as the current monthly dosing paradigm used with palivizumab.

TABLE 10

Determination of the $ED_{99}$ for Anti RSV-F Antibodies After RSV Subtype A Challenge
$ED_{99}$ Determination with RSV Subtype A

| PID | 10 mg/kg | 5 mg/kg | 2.5 mg/kg | 1.25 mg/kg | 0.62 mg/kg |
|---|---|---|---|---|---|
| | % Viral Lung Reduction | | | | |
| H1H3592P3 | >99 | >99 | >99 | >99 | >99 |
| Control I | >99 | >99 | >99 | 98.9 | 95.9 |
| Isotype Ctrl | NA | NA | NA | NA | NA |
| | Antibody Serum Concentration (ug/ml) | | | | |
| H1H3592P3 | 107.2 ± 3.4 | 48.44 ± 6.1 | 20.15 ± 1.8 | 10.55 ± 1.5 | 4.91 ± 0.7 |
| Control I | 89.16 ± 6.5 | 58.07 ± 6.3 | 26.93 ± 3.3 | 12.72 ± 2.2 | 6.65 ± 0.5 |
| Isotype Ctrl | 90.57 ± 12.6 | — | — | — | 5.39 ± 0.5 |

TABLE 11

Determination of the $ED_{99}$ for Anti RSV-F Antibodies After RSV Subtype B Challenge
$ED_{99}$ Determination with RSV Subtype B

| PID | 10 mg/kg | 5 mg/kg | 2.5 mg/kg | 1.25 mg/kg | 0.62 mg/kg |
|---|---|---|---|---|---|
| | % Viral Lung Reduction | | | | |
| H1H3592P3 | >99 | >99 | >99 | 98.4 | 96.7 |
| Control I | >99 | 97.7 | 98.4 | 96.3 | 88.2 |
| Isotype Ctrl | NA | NA | NA | NA | NA |
| | Antibody Serum Concentration (ug/ml) | | | | |
| H1H3592P3 | 98.04 ± 18.4 | 50.99 ± 7.8 | 27.82 ± 4.9 | 10.49 ± 1.7 | 7 ± 0.3 |
| Control I | 98.89 ± 10.9 | 42.74 ± 8.9 | 26.46 ± 3.3 | 16.06 ± 2.2 | 7.58 ± 1.1 |
| Isotype Ctrl | 99.72 ± 17.4 | NA | NA | NA | 5.38 ± 0.5 |

Example 6

Generation of a Bi-specific Antibody

Various bi-specific antibodies are generated for use in practicing the methods of the invention. For example, RSV-F specific antibodies are generated in a bi-specific format (a "bi-specific") in which variable regions binding to distinct domains of the RSV-F protein are linked together to confer dual-domain specificity within a single binding molecule. Appropriately designed bi-specifics may enhance overall virus neutralization efficacy through increasing both specificity and binding avidity. Variable regions with specificity for individual domains are paired on a structural scaffold that allows each region to bind simultaneously to separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022759 and US2010/0331527).

Alternatively, antibodies that bind RSV-F and a second target, such as, but not limited to, for example, a second different anti-RSV-F antibody, or a toxoid, or a vaccine, may be prepared in a bi-specific format using techniques described herein, or other techniques known to those skilled in the art. Antibody variable regions binding to distinct regions may be linked together with variable regions that bind to relevant sites on, for example, a different viral antigen to confer dual-antigen specificity within a single binding molecule. Appropriately designed bi-specifics of this nature serve a dual function. For example, in the case of a bi-specific antibody that binds ie. RSV-F and RSV-G one may be able to better neutralize the virus, without the need for administration of a composition containing two separate antibodies. Variable regions with specificity for RSV-F, are combined with a variable region with specificity for RSV-G and are paired on a structural scaffold that allows each variable region to bind to the separate antigens.

The bi-specific binders are tested for binding and functional blocking of the target antigens, for example, RSV-F and RSV-G, in any of the assays described above for antibodies. For example, standard methods to measure soluble protein binding are used to assess the bispecific interaction, such as Biacore, ELISA, size exclusion chromatography, multi-angle laser light scattering, direct scanning calorimetry, and other methods. Binding of bi-specific antibodies to both RSV-F and RSV-G is determined through use of an ELISA binding assay in which synthetic peptides representing the different antigens are coated onto the wells of microtiter plates, and binding of a bi-specific is determined through use of a secondary detection antibody. Binding experiments can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of both RSV-F and RSV-G by a bi-specific is determined using any bioassay such as the neutralization assay described herein, or by in vivo protection studies in appropriate animal models, such as those described herein, or in an in vivo model of lung inflammation.

Example 7

In Vitro Generation of RSV Escape Mutants to Determine the Binding Epitope of H1H3592P3

Generation of Escape Mutants to H1H3592P3

$3 \times 10^5$ Hep-2 cells/well were plated in a 6-well plate for 24 h. Concentrations of H1H3592P3, ranging from 50 ug/mL to 0.016 ug/mL were mixed with RSV subtype A strain 1540 or RSV subtype B strain 1580 for 1 h at 37° C. After coincubation, the RSV/antibody mixture was added to the previously seeded HEp-2 cells at a multiplicity of infection (MOI) of 10 plaque-forming units (pfu)/cell. Cells were incubated for 6 days, and cytopathic effects were monitored daily using light microscopy. At day 6, contents of each well were harvested, adjusted to initial concentration of antibody and used to infect freshly seeded HEp-2 cells. This serial passage was repeated until obvious cytopathic effects were observed at high concentrations of H1H3592P3 (50 ug/mL), which is approximately 2 logs greater than the $IC_{50}$ of the antibody, suggesting the presence of viral mutants. Supernatants from these wells were confirmed from the presence of resistant virus via a micro-neutralization assay (described below) and plaque isolation was performed in 10 cm tissue culture dishes. 10 individual plaques were expanded in 6-well plates and virus were re-tested for resistance via microneutralization. Sequencing was then performed on these viral mutants.

Microneutralization Assay

To confirm whether escape mutants generated under the pressure of H1H3592P3 were resistant to neutralization, a microneutralization assay in Hep-2 cells was performed. Briefly, $10^5$ Hep2 cells cultured in DMEM 1× medium, supplemented with 5% Hyclone FBS, L-glutamine and antibiotics, were seeded into 96-well clear bottom-black microplates and incubated for 16-18 hours (37C, 5% $CO_2$).

Next, various concentrations of antibodies, starting at 666 nM and diluted 1:5 in media, were incubated for 2 hours (37C, 5% $CO_2$) with RSV wild-type (subtype A or B) or escape mutants from both subtype A and B, at an MOI from 0.04 to 0.4. Controls not containing virus or controls containing virus but no antibodies were included. All dilutions of antibody were conducted in duplicates. After incubation, the antibody/virus mixture was added to cells and infection was allowed for 3 days. Infection was determined by fixing the cells in 2% PFA and an ELISA with Goat anti-RSV/anti-Goat HRP antibodies was performed. Luminescence reagents were added to the wells and signal was detected using a plate reader (Victor X3, Perkin Elmer). Luminescence values were analyzed by a three-parameter logistic equation over an 11-point response curve (GraphPad Prism).

Results

Respiratory syncytial virus escape mutants were generated to map the specific binding region of H1H3592P3 to RSV-F. Briefly, HEp-2 cells, infected with RSV strains 1540 (subtype A) or 1580 (subtype B) were subjected to H1H3592P3 treatment ranging from 50 ug/mL to 0.016 ug/mL. After 6 days, contents from each well were used to infect freshly seeded HEp-2 cells. This serial passage continued until cytopathic effects were observed in HEp-2 cells even in the presence of the highest antibody dose, indicating the presence of RSV viral mutants generated under selection pressure. Overall, viral mutants were isolated from ten distinct plaques, confirmed for neutralization resistance in the presence of H1H3592P3 and subsequently sequenced.

Sequence analysis confirmed that escape mutations for H1H3592P3 were found at amino acid positions 173 and 174 (S 173Y and T174K) of RSV-F (SEQ ID NO: 354), indicating that these amino acids play an important role in antibody binding and viral neutralization. Prior reports have determined that the binding epitopes for anti-RSV Control I and Control II antibodies are located between S255-N276. The data from these studies suggest a binding site for H1H3592P3 on RSV-F that plays a major role in viral neutralization (see table 12) and is distinct from that required for previously established Control antibodies.

TABLE 12

Neutralization Efficacy of H1H3592P3 and anti-RSV Control Antibodies on RSV subtype A and B Strains and Associated Escape Mutants

| Virus | H1H3592P3 (IC50, pM) | Control I (IC50, pM) | Control II (IC50, pM) |
|---|---|---|---|
| wt subtype A (RSV/A) | 177 | 1140 | 108 |
| RSV/A S173Y | Resistant | 1710 | 170 |
| Wt subtype B (RSV/B) | 290 | 1900 | 260 |
| RSV/B S173T | Resistant | 1900 | 177 |
| RSV/B T174K | Resistant | 640 | 108 |
| RSV/B S173T/T174K | Resistant | 980 | 218 |

Example 8

Determination of the Binding Epitope of H1H3592P3 to RSV-F using Hydrogen-Deuterium Exchange & Mass Spectrometry Hydrogen/Deuterium Exchange (H/D exchange) in combination with peptic digests and mass spectrometry was conducted to determine the binding epitope of the anti-RSV-F antibody H1H3592P3 to recombinant RSV-F. Two H/D exchange formats (described in detail below) were employed: An 'on-solution/off-beads' method in which RSV-F peptide fragments that are protected by H1H3592P3 from back-exchange retain $D_2O$ and yield higher molecule weights (m/z values) by mass spectrometry and an 'on-beads/off-beads' control method which establishes the baseline m/z values for all RSV-F peptides. Subtraction of the control m/z values from the m/z values obtained using the 'on-solution/off beads' method yields certain amino acids regions that show non-zero delta m/z values i.e residual $D_2O$ that correspond to the binding epitope between H1H3592P3 and RSV-F.

Methods

On Solution/Off Beads Format

In the 'on-solution/off-beads' (on-exchange in solution followed by off-exchange on beads) format, RSV-F.mmh protein (SEQ ID NO: 353) was deuterated for 5 min or 10 min in PBS buffer prepared with $D_2O$, and then bound to H1H3592P3 covalently attached to N-hydroxysuccinimide (NHS) agarose beads (GE Lifescience) via a 2 min incubation. The RSV-F/H1H3592P3 bead complex was washed with PBS buffer (prepared with non-deuterated $H_2O$) and incubated in PBS buffer for half of the on-exchange time. After the off-exchange, the bound RSV-F was eluted from beads with an ice-cold low pH TFA solution. The eluted RSV-F was then digested with immobilized pepsin (Thermo Scientific) for 5 min. The resulting peptides were desalted using ZipTip chromatographic pipette tips and immediately analyzed by UltrafleXtreme matrix assisted laser desorption ionization time of flight (MALDI-TOF)-TOF mass spectrometry (MS).

On-Beads/Off Beads Format

In the 'on-beads/off-beads' (on-exchange on beads followed by off-exchange on beads) format, RSV-F.mmh (SEQ ID NO: 353) was first bound to H1H3592P3 agarose beads and then incubated for 5 min or 10 min in $D_2O$ for on-exchange. The RSV-F/H1H3592P3 bead complex was washed with PBS buffer (prepared with non-deuterated $H_2O$) and incubated in PBS buffer for half of the on-exchange time. After the off-exchange, the bound RSV-F was eluted from beads with an ice-cold low pH TFA solution. The eluted RSV-F was then digested with immobilized pepsin (Thermo Scientific) for 5 min. The resulting peptides were desalted using ZipTip chromatographic pipette tips and immediately analyzed by MALDI-TOF-TOF mass spectrometry. The centroid values or average mass-to-charge ratios (m/z) of all the detected peptides were calculated and compared between this and the 'on-solution/off-beads' experiment.

Peptide Identification

The identification of the peptides was carried out using liquid chromatography-Orbitrap Elite (Thermo Scientific).

Results

Table 13 is a detailed comparison of the delta centroid m/z values for all the RSV-F peptides detected by MALDI-TOF mass spectrometry following H/D exchange and peptic digest. Two segments corresponding to amino acids 161-171 (EGEVNKIKSAL, (SEQ ID NO: 355)) and 172-188 (LSTNKAVVSLSNGVSVL, (SEQ ID NO: 356)) of SEQ ID NO: 354 had delta centroid values higher than 0.20, a threshold observed in-house to be considered indicative of antibody-protein contact and thus an epitope region. It should also be noted that the peptide signal corresponding to amino acids 161-171 was not quantified in the 10 min on-exchange experiment due to low signal to noise. However, the delta value of 0.88, detected at the 5 min on-exchange experiment, is far above the 0.2 threshold and can be attributed to the significant alteration in H/D exchange rate upon RSV-F binding to H1H3592P3.

Furthermore the peptide segment corresponding to amino acids 172-188 contains the amino acids of the two RSV escape mutants (S173Y and T174K; see example 7), which were resistant to H1H3592P3 treatment, indicating that these two amino acids play a role in antibody binding and viral neutralization. Thus the combination of sequencing escape RSV mutants along with H/D exchange support amino acids 161-188 of SEQ ID NO: 354 defining at least in part the binding region in RSV-F for antibody H1H3592P3.

TABLE 13

Centroid (m/z) Values of RSV-F Peptic Peptides After Back-exchange following deuteration in the Absence (on-solution/off-beads) and Presence (on-beads/off-beads) of H1H3592P3

| | Experiment I 5 min on-/2.5 min off-exchange | | | Experiment II 10 min on-/5 min off-exchange | | |
|---|---|---|---|---|---|---|
| Residues | on-beads/ off beads (m/z) | on-solution/ off-beads (m/z) | delta | on-beads/ off beads (m/z) | on-solution/ off-beads (m/z) | delta |
| 46-52 | 791.06 | 791.10 | 0.04 | 791.06 | 791.15 | 0.09 |
| 48-56 | 1083.32 | 1083.37 | 0.05 | 1083.32 | 1083.35 | 0.03 |
| 48-58 | 1297.42 | 1297.44 | 0.02 | 1297.40 | 1297.44 | 0.04 |
| 79-92 | 1665.81 | 1665.96 | 0.15 | 1665.86 | 1665.89 | 0.03 |
| 94-107 | 1519.93 | 1520.00 | 0.06 | 1520.01 | 1520.09 | 0.07 |
| 96-107 | 1278.64 | 1278.61 | −0.03 | 1278.61 | 1278.73 | 0.12 |
| 96-108 | 1434.61 | 1434.60 | −0.01 | 1434.50 | 1434.63 | 0.13 |
| 148-160 | 1308.97 | 1309.12 | 0.16 | N.A. | N.A. | N.A. |
| 161-171 | 1188.72 | 1189.60 | 0.88 | N.A. | N.A. | N.A. |
| 172-188 | 1689.44 | 1691.68 | 2.24 | 1689.60 | 1691.07 | 1.47 |
| 220-230 | 1390.02 | 1390.06 | 0.04 | 1389.98 | 1389.93 | −0.05 |
| 220-232 | 1632.30 | 1632.34 | 0.04 | 1632.29 | 1632.37 | 0.08 |
| 223-230 | 1048.49 | 1048.54 | 0.05 | 1048.44 | 1048.55 | 0.11 |
| 223-232 | 1291.16 | 1291.21 | 0.05 | 1291.12 | 1291.18 | 0.07 |
| 231-236 | 760.95 | 760.95 | 0.00 | 761.02 | 760.95 | −0.06 |
| 233-240 | 966.29 | 966.33 | 0.04 | 966.20 | 966.30 | 0.09 |
| 233-249 | 1780.20 | 1780.39 | 0.19 | 1780.38 | 1780.38 | 0.00 |
| 261-277 | 1977.81 | 1977.91 | 0.10 | 1977.92 | 1977.80 | −0.13 |
| 261-279 | 2205.05 | 2205.12 | 0.07 | 2205.10 | 2205.20 | 0.10 |
| 278-285 | 958.20 | 958.34 | 0.14 | 958.15 | 958.29 | 0.14 |
| 278-286 | 1121.50 | 1121.57 | 0.07 | 1121.54 | 1121.59 | 0.05 |
| 278-289 | 1453.19 | 1453.16 | −0.03 | 1453.14 | 1453.08 | −0.06 |
| 280-286 | 894.20 | 894.22 | 0.02 | 894.29 | 894.28 | −0.02 |
| 280-289 | 1225.75 | 1225.80 | 0.05 | 1225.79 | 1225.81 | 0.02 |
| 280-290 | 1312.70 | 1312.70 | −0.01 | 1312.86 | 1312.74 | −0.13 |
| 457-467 | 1329.73 | 1329.82 | 0.09 | 1329.73 | 1329.76 | 0.03 |
| 468-477 | 1180.57 | 1180.67 | 0.10 | 1180.60 | 1180.42 | −0.18 |
| 527-545 | 2132.30 | 2132.32 | 0.02 | 2132.39 | 2132.38 | −0.01 |
| 534-545 | 1318.54 | 1318.54 | 0.00 | 1318.64 | 1318.50 | −0.13 |
| 537-545 | 988.92 | 988.87 | −0.05 | 988.93 | 988.84 | −0.08 |
| 546-557 | 1528.62 | 1528.68 | 0.07 | 1528.64 | 1528.64 | 0.00 |
| No ID | 743.16 | 743.06 | −0.10 | 743.10 | 742.99 | −0.11 |
| No ID | 844.01 | 843.98 | −0.03 | 844.03 | 843.96 | −0.07 |
| No ID | 901.26 | 901.40 | 0.13 | 901.36 | 901.40 | 0.04 |
| No ID | 943.15 | 943.19 | 0.04 | 943.24 | 943.20 | −0.04 |
| No ID | 1090.41 | 1090.45 | 0.04 | 1090.48 | 1090.51 | 0.03 |
| No ID | 1143.51 | 1143.61 | 0.10 | 1143.53 | 1143.57 | 0.04 |
| No ID | 1325.52 | 1325.56 | 0.04 | 1325.54 | 1325.66 | 0.12 |
| No ID | 1353.69 | 1353.64 | −0.06 | 1353.77 | 1353.61 | −0.16 |
| No ID | 1550.39 | 1550.44 | 0.05 | 1550.45 | 1550.40 | −0.05 |
| No ID | 2074.49 | 2074.41 | −0.08 | 2074.52 | 2074.36 | −0.15 |
| No ID | 2257.71 | 2257.70 | −0.01 | 2257.89 | 2257.85 | −0.04 |
| No ID | 2365.83 | 2365.72 | −0.12 | 2365.94 | 2365.87 | −0.07 |
| No ID | 2385.18 | 2385.17 | −0.01 | 2385.23 | 2385.25 | 0.02 |
| No ID | 2405.22 | 2405.09 | −0.12 | 2405.17 | 2405.15 | −0.02 |
| No ID | 2456.18 | 2456.24 | 0.07 | 2456.14 | 2456.09 | −0.05 |
| No ID | 2513.28 | 2513.26 | −0.01 | 2513.32 | 2513.19 | −0.14 |

Example 9

Respiratory Syncytial Virus Fusion (RSV-F) Protein Antibodies Display Potent Neutralization Capabilities Across RSV Subtype A and B Laboratory Strains H1H3592P3 and controls I and II antibodies were tested in a RSV micro-neutralization assay to determine potency. Briefly, $10^4$ HEp-2 cells cultured in DMEM 1× medium, supplemented with 5% Hyclone FBS, L-glutamine and antibiotics, were seeded into 96-well clear bottom-black microplates and incubated for 16-18 hours (37° C., 5% $CO_2$). Next, various concentrations of antibodies, starting at 666 nM with subsequent 1:5 dilutions in media, were incubated with various RSV subtype A lab strains provided by ATCC at an MOI of 0.042 for 2 hours (37C, 5% $CO_2$). Virus-free and irrelevant isotype controls were included.

Post incubation, the antibody:virus mixture was added to the HEp-2 cells and infection was maintained for 3 days. The degree of infection was determined by fixing cells in 2% PFA and performing an ELISA with Goat anti-RSV/anti-Goat HRP antibodies. Luminescence reagents were added to the wells and signal was detected using a plate reader (Victor X3, Perkin Elmer). Luminescence values were analyzed by a three-parameter logistic equation over an 11-point response curve (GraphPad Prism).

The antibodies of the invention displayed a broad range of neutralization activities against the RSV lab strains (Table 14). Antibodies H1H3592P3 and AM22 showed similar potency than control II for RSV subtype A lab strains. Compared to control I, H1H3592P3 showed 15-17 fold more potency (IC50 44-140 pM), while AM22 showed 9-23 fold more potency (IC50 86-91 pM) (Table 14). For subtype B, antibody H1H3592P3 showed similar potency than control II, but superior than AM22 and control I. Compared to control I, H1H3592P3 showed 2-5 fold more potency (IC50 33-230 pM), while AM22 showed 0.13-2 fold more potency (IC50 190-2508 pM).

This example demonstrates the efficacy of the antibodies of this invention to neutralize several lab strains of RSV from both subtype A and B, in vitro, with greater potency than previously demonstrated for established controls.

and antibiotics, were seeded into 96-well clear bottom-black microplates and incubated for 16-18 hours (37° C., 5% $CO_2$). Next, various concentrations of antibodies, starting at 666 nM with subsequent 1:5 dilutions in media, were incubated with various RSV subtype A clinical isolates provided by Dr. Moore (Emory University) at a range of MOIs from 0.015 to 0.128 for 2 hours (37C, 5% $CO_2$). Virus-free and irrelevant isotype controls were included.

Post incubation, the antibody:virus mixture was added to the HEp-2 cells and infection was maintained for 3 days. The degree of infection was determined by fixing cells in 2% PFA and performing an ELISA with Goat anti-RSV/anti-Goat HRP antibodies. Luminescence reagents were added to the wells and signal was detected using a plate reader (Victor X3, Perkin Elmer). Luminescence values were analyzed by a three-parameter logistic equation over an 11-point response curve (GraphPad Prism).

The antibodies of the invention displayed a broad range of neutralization activities against the RSV clinical isolates (Table 15). Antibody H1H3592P3 showed similar potency to controls II and III for most clinical isolates. Compared to control I, H1H3592P3 showed 10-22 fold more potency (IC50 34-66 pM) (Table 15).

This example demonstrates the efficacy of the antibodies of this invention to neutralize several clinical isolates of RSV, in vitro, with greater potency than previously demonstrated for established controls.

TABLE 15

RSV-F Antibodies Display Potent Neutralization Capabilities Across RSV Subtype A clinical isolates

| | MOI | H1H3592P3 IC50 (pM) | Control I IC50 (pM) | Control II IC50 (pM) | Control III IC50 (pM) | Genbank |
|---|---|---|---|---|---|---|
| A2001/2-20 | 0.016 | 43 | 935 | 74 | 72 | JX069798.1 |
| A2001/3-12 | 0.018 | 66 | 1259 | 129 | 60 | JX069799.1 |
| A1997/12-35 | 0.015 | 40 | 478 | 41 | 20 | JX069800.1 |
| A1998/3-2 | 0.128 | 35 | 344 | 36 | 31 | JX069801.1 |
| A1998/12-21 | 0.026 | 34 | 580 | 68 | 43 | JX069802.1 |
| A2000/3-4 | 0.040 | 50 | 899 | 88 | 55 | JX069803.1 |

TABLE 14

| Subtype/strain | H1H3592P3 IC50 (pM) | Control I IC50 (pM) | Control II IC50 (pM) | Control III IC50 (pM) |
|---|---|---|---|---|
| A/A2 | 140 | 2080 | 202 | 91 |
| A/Long | 44 | 752 | 83 | 86 |
| B/18537 | 230 | 1190 | 187 | 660 |
| B/1400 | 33 | 113 | 38 | 190 |
| B/1A2 | 48 | 223 | 40 | 580 |
| B/9320 | 151 | 338 | 76 | 2508 |

Example 10

Respiratory Syncytial Virus Fusion (RSV-F) Protein Antibodies Display Potent Neutralization Capabilities Across RSV Subtype A Clinical Isolates H1H3592P3 and controls I, II and III antibodies were tested in a RSV micro-neutralization assay to determine potency. Briefly, $10^4$ HEp-2 cells cultured in DMEM 1' medium, supplemented with 5% Hyclone FBS, L-glutamine Example 11

H1H3592P3 Blocks Viral Entry by Inhibiting Fusion of Virus and Cell Membranes

Figure 2A:
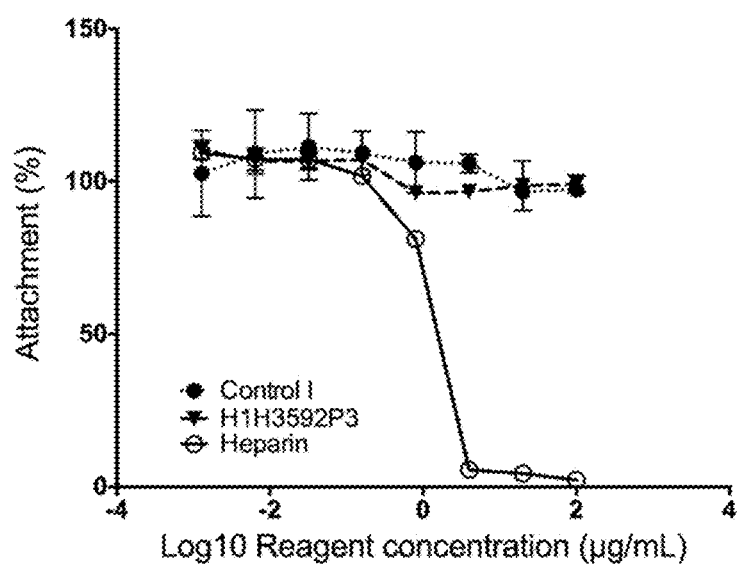
FIGS. 2A and 2B show that H1H3592P3 blocks viral entry by inhibiting fusion of virus and cell membranes.
Figure 2B:
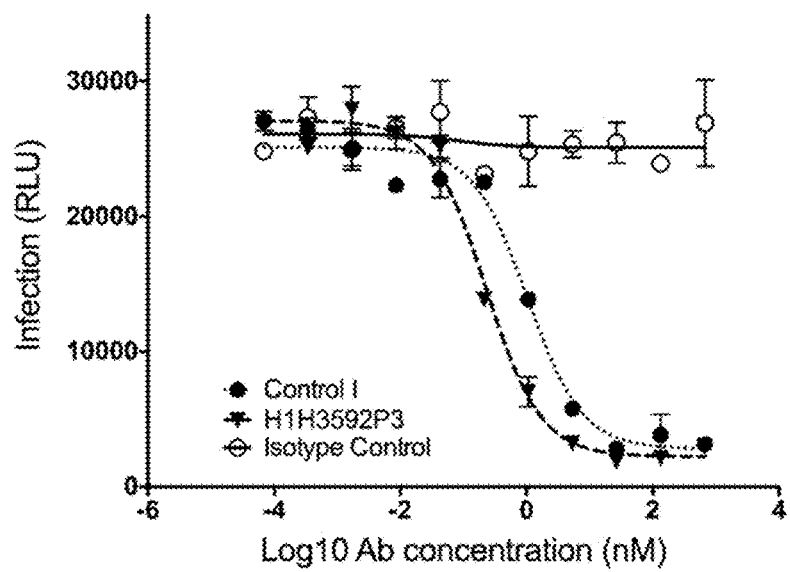

A study was done to determine the mechanism by which the antibodies of the invention block respiratory syncytial virus (RSV) infection. One exemplary antibody of the invention, H1H3592P3, was tested to determine whether it acted to prevent/inhibit RSV fusion with host cells (FIG. 2A and 2B). The mechanism of action for control I (the positive control mAb which is based on the sequence of palivizumab) was previously described as inhibition of viral fusion to the host cell (Huang et al., J. of Virol., (2010), August 84(16):8132-40). Because RSV-F is involved in both attachment to the cell via the interaction of the host receptor nucleolin, and fusion of the viral and plasma membranes, assays were performed to determine the mechanism of H1H3592P3.

The attachment assay (FIG. 2A) was performed by incubating RSV (subtype A, strain A2) in the presence of either H1H3592P3 or the positive control antibody (control I), then incubating the mixture with HEp-2 cells at 4° C. for one hour to allow binding of the virus to the cells. Unbound virus was washed out, cells were fixed and the percentage of attached virus was measured by ELISA. Heparin, which blocks RSV attachment, was used as a control.

Viral fusion was detected by allowing viral attachment at 4° C., washing out unbound virus, then incubating with H1H3592P3, positive Control I, or an isotype negative control antibody at 4° C. and moving cells to 37° C. to promote viral fusion and entry. Viral infection was measured 3 days later by ELISA (FIG. 2B). RLU: Relative Luminescence Units.

H1H3592P3, like control I, blocks RSV fusion and not the attachment of RSV to the cell surface, while the isotype (negative) control mAb had no effect on viral fusion (FIG. 2B). Heparin effectively blocked RSV attachment to cells (Hallack et al., Virology (2000), 271 (2):264-75), whereas neither antibody inhibited RSV attachment (FIG. 2A). H1H3592P3 blocked viral fusion in this assay format with an $IC_{50}$ of 230 pM, while the positive control mAb (control I) blocked viral fusion with an $IC_{50}$ 1 nM (FIG. 2B). Similar results were observed with an RSV subtype B strain (data not shown).

Example 12

Octet Cross Competition of anti-RSV-F Antibodies for Binding to RSV-F

Binding competition between a panel of anti-RSV-F mAbs was determined using a real time, label-free bio-layer interferometry assay on an Octet® HTX biosensor (Pall ForteBio Corp.). The entire experiment was performed at 25° C. in HBST kinetics buffer (0.01 M HEPES pH7.4, 0.15M NaCl, 3mM EDTA, 0.05% v/v Surfactant Tween-20, 0.1mg/mL BSA) with the plate shaking at the speed of 1000rpm. To assess whether two antibodies are able to compete with one another for binding to their respective epitopes on the recombinant RSV-F protein expressed with a C-terminal myc-myc-hexahistidine tag (RSV-F-mmH), around 0.36nm of RSV-F-mmH was first captured onto anti-Penta-His antibody coated Octet biosensor (Fortebio Inc, Cat# 18- 5079) by submerging the biosensors for 3minutes into wells containing 10μg/mL solution of recombinant RSV-F-mmH. The antigen captured biosensors were then saturated with the first anti-RSV-F monoclonal antibody (subsequently referred to as mAb-1) by dipping into wells containing 100-200μg/mL solution of mAb-1 for 10minutes. The biosensors were then subsequently dipped into wells containing 100- 200μg/mL solution of second anti-RSV-F monoclonal antibody (subsequently referred to as mAb-2) for 5minutes to check for mAb-2 binding to RSV-F-mmH, which is pre-bound to mAb-1. The biosensors were washed in HBST kinetics buffer in between every step of the experiment. The real-time binding response was monitored throughout the course of the experiment and the maximum binding response for all the steps was recorded. The response of mAb-2 binding to RSV-F-mmH pre-bound with mAb-1 was measured and competitive/non-competitive behavior of different anti-RSV-F monoclonal antibodies was determined.

Results

Sequential binding studies performed on Octet® HTX demonstrate that none of the anti-RSV-F monoclonal antibodies compete with each other and are able to bind non-competitively to RSV-F-mmH. As shown in Table 16, underlined values indicate the binding response for self-competition. No competition between antibodies that suggest a distinct binding epitope is represented in the values without underlining Binding of the first anti-RSV-F monoclonal antibody (mAb-1) to the anti-His-captured RSV-F-mmH protein does not prevent the binding of the second anti-RSV-F monoclonal antibody (mAb-2). For all the anti-RSV-F monoclonal antibodies in this study, the observed mAb-2 binding signal was found to be comparable to that observed in the absence of mAb-1 (No mAb). Moreover, the observed binding of mAb-2 for all the anti-RSV-F monoclonal antibodies was found to be independent of the order of binding of anti-RSV-F antibody; suggesting that all the anti-RSV-F antibodies under investigation have distinct binding epitopes.

TABLE 16

Cross-competition between anti-RSV-F monoclonal antibodies.

| mAb-1 | Amount of 10 μg/mL of RSV_F · mmh Captured ± Std Dev (nm) | Amount of 100-200 μg/mL of mAb-1 Binding Level (nm) | mAb# | Binding of mAb-2 to the Pre-complex of Captured RSV-F-mmH & mAb-1 | | | |
|---|---|---|---|---|---|---|---|
| | | | | 1 | 2 | 3 | 4 |
| Comparator III (AM-22) | 0.36 ± 0.01 | 0.33 ± 0.01 | 1 | 0.01 | 0.34 | 0.44 | 0.00 |
| H1H3592P3 | 0.36 ± 0.01 | 0.35 ± 0.01 | 2 | 0.26 | 0.00 | 0.30 | 0.00 |
| Comparator I (Palivizumab) | 0.39 ± 0.01 | 0.45 ± 0.02 | 3 | 0.29 | 0.23 | 0.01 | −0.01 |
| No mAb | 0.36 ± 0.01 | −0.01 ± 0.01 | 4 | 0.20 | 0.17 | 0.36 | 0.00 |

What is claimed is:

1. An isolated human antibody or antigen-binding fragment thereof that binds specifically to RSV-F, wherein the antibody or antigen-binding fragment comprises three heavy chain complementarity determining regions (CDRs) (HCDR1, HCDR2 and HCDR3) contained within a heavy chain variable region (HCVR) comprising the amino acid sequence of SEQ ID NO: 274; and comprises three light chain CDRs (LCDR1, LCDR2 and LCDR3) contained within a light chain variable region (LCVR) comprising the amino acid sequence of SEQ ID NOs: 282, wherein the CDRs are identified by the Kabat definition, the Chothia definition, or the AbM definition.

2. The isolated human antibody or antigen-binding fragment of claim 1, comprising:
   (a) a HCDR1 domain having the amino acid sequence of SEQ ID NO: 276;
   (b) a HCDR2 domain having the amino acid sequence of SEQ ID NO: 278;
   (c) a HCDR3 domain having the amino acid sequence of SEQ ID NO: 280;
   (d) a LCDR1 domain having the amino acid sequence of SEQ ID NO: 284;
   (e) a LCDR2 domain having the amino acid sequence of SEQ ID NO: 286; and
   (f) a LCDR3 domain having the amino acid sequence of SEQ ID NO: 288.

3. The isolated antibody or antigen-binding fragment of claim 2, comprising the HCVR/LCVR amino acid sequence pair of SEQ ID NOs: 274/282, wherein the antibody or antigen-binding fragment binds to RSV-F within amino acids 161-188 of SEQ ID NO: 354.

4. An isolated nucleic acid molecule encoding the antibody or antigen-binding fragment of claim 1.

5. An expression vector comprising the nucleic acid molecule of claim 4.

6. A host cell comprising the expression vector of claim 5.

7. A method for treating a respiratory syncytial virus (RSV) infection, the method comprising administering an antibody or antigen-binding fragment of claim 1, or a composition comprising an antibody or antigen-binding fragment of claim 1, to a patient in need thereof.

8. The method of claim 7, wherein:
   (a) the RSV infection is caused by a subtype A or a subtype B respiratory syncytial virus; and/or
   (b) the patient in need thereof is a patient at high risk of acquiring an RSV infection, or a patient who may experience a more severe form of the RSV infection due to an underlying or pre-existing medical condition.

9. The method of claim 8, wherein:
   (a) the patient is a pre-term infant, a full term infant, a child greater than or equal to one year of age with or without an underlying medical condition (e.g. congenital heart disease, chronic lung disease, cystic fibrosis, immunodeficiency, a neuromuscular disorder), an institutionalized or hospitalized patient, or an elderly adult (greater than 65 years of age) with or without an underlying medical condition such as congestive heart failure or chronic obstructive pulmonary disease); or
   (b) the patient suffers from a condition resulting from a compromised pulmonary, cardiovascular, neuromuscular, or immune system.

10. The method of claim 9, wherein the condition is selected from the group consisting of an abnormality of the airway, a chronic lung disease, a chronic heart disease, a neuromuscular disease that compromises the handling of respiratory secretions and immunosuppression.

11. The method of claim 10, wherein:
    (a) the chronic lung disease is chronic obstructive pulmonary disease (COPD), cystic fibrosis, or bronchopulmonary dysplasia, optionally wherein the chronic heart disease is congestive heart failure (CHF), or congenital heart disease; and/or
    (b) the immunosuppression is a result of severe combined immunodeficiency or severe acquired immunodeficiency, or is a result of any other infectious disease or cancerous condition that leads to immunosuppression, or is a result of treatment with immunosuppressant drug therapy or radiation therapy.

12. The method of claim 7, wherein:
    (a) the antibody or antigen-binding fragment thereof is administered via a route selected from the group consisting of intravenously, intramuscularly, and subcutaneously; and/or
    (b) the antibody or antigen-binding fragment is administered to the patient in combination with a second therapeutic agent.

13. A pharmaceutical composition comprising the antibody or antigen binding fragment thereof of claim 1 and a pharmaceutically acceptable carrier.

14. An isolated human antibody or antigen-binding fragment thereof that binds specifically to RSV-F, wherein the antibody or antigen-binding fragment comprises three heavy chain complementarity determining regions (CDRs) (HCDR1, HCDR2 and HCDR3) contained within a heavy chain variable region (HCVR) comprising the amino acid sequence of SEQ ID NO: 338; and comprises three light chain CDRs (LCDR1, LCDR2 and LCDR3) contained within a light chain variable region (LCVR) comprising the amino acid sequence of SEQ ID NOs: 346, wherein the CDRs are identified by the Kabat definition, the Chothia definition, or the AbM definition.

15. The isolated human antibody or antigen-binding fragment of claim 14, comprising:
    (a) a HCDR1 domain having the amino acid sequence of SEQ ID NO: 340;
    (b) a HCDR2 domain having the amino acid sequence of SEQ ID NO: 342;
    (c) a HCDR3 domain having the amino acid sequence of SEQ ID NO: 344;
    (d) a LCDR1 domain having the amino acid sequence of SEQ ID NO: 348;
    (e) a LCDR2 domain having the amino acid sequence of SEQ ID NO: 350; and
    (f) a LCDR3 domain having the amino acid sequence of SEQ ID NO: 352.

16. The isolated antibody or antigen-binding fragment of claim 15, comprising the HCVR/LCVR amino acid sequence pair of SEQ ID NOs: 338/346.

17. An isolated nucleic acid molecule encoding an antibody or antigen-binding fragment of claim 14.

18. An expression vector comprising the nucleic acid molecule of claim 17.

19. A host cell comprising the expression vector of claim 18.

20. A method for treating a respiratory syncytial virus (RSV) infection, the method comprising administering an antibody or antigen-binding fragment of claim 14, or a composition comprising an antibody or antigen-binding fragment of claim 14, to a patient in need thereof.

21. The method of claim 20, wherein:
    (a) the RSV infection is caused by a subtype A or a subtype B respiratory syncytial virus; and/or
    (b) the patient in need thereof is a patient at high risk of acquiring an RSV infection, or a patient who may experience a more severe form of the RSV infection due to an underlying or pre-existing medical condition.

22. The method of claim 21, wherein:
    (a) the patient is a pre-term infant, a full term infant, a child greater than or equal to one year of age with or without an underlying medical condition (e.g. congenital heart disease, chronic lung disease, cystic fibrosis, immunodeficiency, a neuromuscular disorder), an institutionalized or hospitalized patient, or an elderly adult (greater than 65 years of age) with or without an underlying medical condition such as congestive heart failure or chronic obstructive pulmonary disease); or
    (b) the patient suffers from a condition resulting from a compromised pulmonary, cardiovascular, neuromuscular, or immune system.

23. The method of claim 22, wherein the condition is selected from the group consisting of an abnormality of the airway, a chronic lung disease, a chronic heart disease, a neuromuscular disease that compromises the handling of respiratory secretions and immunosuppression.

24. The method of claim 23, wherein:
    (a) the chronic lung disease is chronic obstructive pulmonary disease (COPD), cystic fibrosis, or bronchopulmonary dysplasia, optionally wherein the chronic heart disease is congestive heart failure (CHF), or congenital heart disease; and/or
    (b) the immunosuppression is a result of severe combined immunodeficiency or severe acquired immunodeficiency, or is a result of any other infectious disease or cancerous condition that leads to immunosuppression, or is a result of treatment with immunosuppressant drug therapy or radiation therapy.

25. The method of claim 20, wherein:
(a) the antibody or antigen-binding fragment thereof is administered via a route selected from the group consisting of intravenously, intramuscularly, and subcutaneously; and/or
(b) the antibody or antigen-binding fragment is administered to the patient in combination with a second therapeutic agent.

26. A pharmaceutical composition comprising the antibody or antigen binding fragment thereof of claim 14 and a pharmaceutically acceptable carrier.

\* \* \* \* \*

UNITED STATES PATENT AND TRADEMARK OFFICE
CERTIFICATE OF CORRECTION

PATENT NO. : 10,125,188 B2
APPLICATION NO. : 15/229567
DATED : November 13, 2018
INVENTOR(S) : Gurnett-Bander et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this
Sixteenth Day of July, 2019

Andrei Iancu
*Director of the United States Patent and Trademark Office*